United States Patent
Andersson et al.

(10) Patent No.: US 7,538,222 B2
(45) Date of Patent: *May 26, 2009

(54) N-SUBSTITUTED PIPERIDINE DERIVATIVES AS SEROTONIN RECEPTOR AGENTS

(75) Inventors: Carl-Magnus Andersson, Hjärup (SE); Nathalie Schlienger, Frederiksberg (DK); Alma Fejzic, Frederiksberg (DK); Eva Louise Hansen, Højby (DK); Jan Pawlas, Frederiksberg (DK)

(73) Assignee: ACADIA Pharmaceuticals, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/299,566

(22) Filed: Dec. 12, 2005

(65) Prior Publication Data

US 2006/0094758 A1  May 4, 2006

Related U.S. Application Data

(63) Continuation of application No. 10/601,070, filed on Jun. 20, 2003, now Pat. No. 7,253,186.

(60) Provisional application No. 60/391,269, filed on Jun. 24, 2002.

(51) Int. Cl.
C07D 401/06 (2006.01)
C07D 413/06 (2006.01)

(52) U.S. Cl. .................... 546/190; 544/129; 544/283; 546/207; 546/208; 546/209; 546/210; 546/211

(58) Field of Classification Search ............... 546/207, 546/208, 209, 210, 211, 190; 544/129, 283
See application file for complete search history.

(56) References Cited

U.S. PATENT DOCUMENTS

| | | | |
|---|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Iglesias et al. |
| 4,853,394 A | 8/1989 | King et al. |
| 5,025,013 A | 6/1991 | Barreau et al. |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda et al. |
| 5,707,798 A | 1/1998 | Brann |
| 5,795,894 A | 8/1998 | Shue et al. |
| 5,869,488 A | 2/1999 | Shue et al. |
| 5,877,173 A | 3/1999 | Olney et al. |
| 5,912,132 A | 6/1999 | Brann |
| 5,955,281 A | 9/1999 | Brann |
| 6,107,324 A | 8/2000 | Behan et al. |
| 6,140,509 A | 10/2000 | Behan et al. |
| 6,150,393 A | 11/2000 | Behan et al. |
| 6,358,698 B1 | 3/2002 | Weiner et al. |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 2004/0006081 A1 | 1/2004 | Burrows et al. |
| 2004/0006089 A1 | 1/2004 | Thurieau et al. |
| 2004/0106600 A1 | 6/2004 | Andersson et al. |
| 2004/0213816 A1 | 10/2004 | Weiner et al. |
| 2005/0014757 A1 | 1/2005 | Andersson et al. |
| 2005/0148018 A1 | 7/2005 | Weiner et al. |
| 2005/0244862 A1 | 11/2005 | Brann |
| 2005/0256108 A1 | 11/2005 | Schlienger |
| 2006/0094758 A1 | 5/2006 | Andersson et al. |
| 2006/0106063 A1 | 5/2006 | Thygesen et al. |

(Continued)

FOREIGN PATENT DOCUMENTS

CA 984843 3/1976

(Continued)

OTHER PUBLICATIONS

Adam, et al. 1989. Effects of repeated ritanserin on middle-aged poor sleepers. *Psychopharmacology*, 99:219-221.

(Continued)

*Primary Examiner*—Charanjit S Aulakh
(74) *Attorney, Agent, or Firm*—Knobbe Martens Olsen & Bear LLP

(57) ABSTRACT

Disclosed herein are compounds of Formula I,

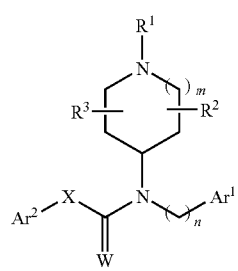

or a pharmaceutically acceptable salt, amide, ester, or prodrug thereof. Also disclosed are methods of inhibiting an activity of a monoamine receptor comprising contacting the monoamine receptor or a system containing the monoamine receptor with an effective amount of one or more of the compounds of Formula I. Disclosed are also methods of inhibiting an activation of a monoamine receptor comprising contacting the monoamine receptor or a system containing the monoamine receptor with an effective amount of one or more of the compounds of Formula I. Furthermore, methods of treating psychotic disease using a compound of Formula I are disclosed.

24 Claims, No Drawings

U.S. PATENT DOCUMENTS

| | | | |
|---|---|---|---|
| 2006/0111399 | A1 | 5/2006 | Thygesen et al. |
| 2006/0194778 | A1 | 8/2006 | Andersson et al. |
| 2006/0194834 | A1 | 8/2006 | Andersson et al. |
| 2006/0199794 | A1 | 9/2006 | Schlienger |
| 2006/0199818 | A1 | 9/2006 | Andersson et al. |
| 2006/0199842 | A1 | 9/2006 | Weiner et al. |
| 2006/0205710 | A1 | 9/2006 | Schlienger et al. |
| 2006/0205722 | A1 | 9/2006 | Andersson et al. |
| 2006/0205780 | A1 | 9/2006 | Thygesen et al. |
| 2006/0205781 | A1 | 9/2006 | Thygesen et al. |

FOREIGN PATENT DOCUMENTS

| | | |
|---|---|---|
| EP | 0 005 318 A1 | 11/1979 |
| EP | 0 061 333 A1 | 9/1982 |
| EP | 0 379 441 A1 | 7/1990 |
| EP | 0 548 015 A1 | 6/1993 |
| EP | 0 260 070 | 8/1993 |
| EP | 0 625 507 A2 | 11/1994 |
| FR | 2 802 206 | 6/2001 |
| HU | 157325 | 3/1998 |
| WO | WO 94/27967 A1 | 12/1994 |
| WO | WO 97/08166 A1 | 3/1997 |
| WO | WO 97/11940 A1 | 4/1997 |
| WO | WO 97/38665 A2 | 10/1997 |
| WO | WO 97/38984 A1 | 10/1997 |
| WO | WO 98/11128 A1 | 3/1998 |
| WO | WO 98/17646 A1 | 4/1998 |
| WO | WO 98/44921 A1 | 10/1998 |
| WO | WO 98/50534 A1 | 11/1998 |
| WO | WO 99/52927 A1 | 10/1999 |
| WO | WO 00/23076 A1 | 4/2000 |
| WO | WO 00/56335 A1 | 9/2000 |
| WO | WO 00/59497 A1 | 10/2000 |
| WO | WO 00/69810 A1 | 11/2000 |
| WO | WO 01/44191 A1 | 6/2001 |
| WO | WO 01/66521 A1 | 9/2001 |
| WO | WO 01/87839 A1 | 11/2001 |
| WO | WO 02/079186 A2 | 10/2002 |
| WO | WO 03/057698 A2 | 7/2003 |
| WO | WO 03/057698 A3 | 7/2003 |
| WO | WO 03/062206 A2 | 7/2003 |
| WO | WO 03/062206 A3 | 7/2003 |
| WO | WO 03/070246 A1 | 8/2003 |
| WO | WO 03/086400 A1 | 10/2003 |
| WO | WO 2004/000808 A2 | 12/2003 |
| WO | WO 2004/000808 A3 | 12/2003 |
| WO | WO 2004/009549 A2 | 1/2004 |
| WO | WO2004/039322 A2 | 5/2004 |
| WO | WO 2004/064738 A2 | 8/2004 |
| WO | WO 2004/064738 A3 | 8/2004 |
| WO | WO 2004/064753 A2 | 8/2004 |
| WO | WO 2004/072034 A1 | 8/2004 |
| WO | WO 2005/063254 A2 | 7/2005 |
| WO | WO 2005/112927 A | 12/2005 |
| WO | WO 2006/036874 A1 | 4/2006 |
| WO | WO 2006/037043 A1 | 4/2006 |

OTHER PUBLICATIONS

Adell, et al. 2005. Strategies for producing faster acting antidepressants. *Drug Discovery Today*, 10(8):578-585.

Akin, et al. 2004. Decreased serotonin 5-HT$_{2A}$ receptor-stimulated phosphoinositide signaling in fibroblasts from melancholic depressed patients. *Neuropsychopharmacology*, 29:2081-2087.

Bakshi, et al. 1994. Clozapine antagonizes phencyclidine-induced deficits in sensorimotor gating of the startle response. *The Journal of Pharmacology and Experimental Therapeutics*, 271(2):787-794.

Bassus, et al. 1974. Psychotropes potentiels. X. Synthèse de butyrophénones à cycle pipéridine-spiro-tétrahydrooxazinone douées d'activité neuroleptique. *Eur. J. Med. Chem.—Chimica Therapeutica*, 9(4):416-423.

Bennett, et al. 1993. Suppression of dyskinesias in advanced Parkinson's disease. II. Increasing dailty clozapine doses suppress dyskinesias and improve parkinsonism symptoms. *Neurology*, 43:1551-1555.

Bhatia, et al. 1996. 5-Lipoxygenase inhibitors: Synthesis and structure-activity relationships of a series of 1-Aryl-2H,4H-tetrahydro-1,2,4,-triazin-3-ones. *J. Med. Chem.*, 39:3938-3950.

Bibbiani, et al. 2001. Serotonin 5-HT1A agonist improves motor complications in rodent and primate parkinsonian models. *Neurology*, 57:1829-1834.

Birkmayer, et al. 1974. Nucleus ruber and L-Dopa psychosis: Biochemical post-mortem findings. *Journal of Neural Transmission*, 35:93-116.

Blakley, et al. 2001. Bidirectional changes in ethanol consumption in rats with site-specific antisense down-regulation of 5-hydroxytryptamine$_{2A}$ receptors in brain. *The Journal of Pharmacology and Experimental Therapeutics*, 299(1):277-289.

Blier, et al. 2001. Putative mechanisms of action of antidepressant drugs in affective and anxiety disorders and pain. *Journal of Psychiatry & Neuroscience*, 26(1):37-43.

Blier, et al. 2005. Potential mechanisms of action of atypical antipsychotic medications in treatment-resistant depression and anxiety. *J. Clin. Psychiatry*, 66(suppl 8):30-40.

Boullin, D. J. 1978. *Serotonin in Mental Abnormalities* (p. 316). New York: Wiley.

Butcher, et al. 1970. L-Dopa induced changes in central monoamine neurons after peripheral decarboxylase inhibition. *Letters to the Editor, J. Pham. Pharmac.*, 22:313-316.

Caroon, et al. 1981. Synthesis and antihypertensive activity of a series of 8-substituted 1-Oxa-3,8-diazaspiro[4.5]decan-2-ones. *J. Med. Chem.*, 24:1320-1328.

Chemical Abstracts, 73:25305. Benke, et al. 1970.

Clark et al. 1983. Antihypertensive 9-substituted 1-Oxa-4,9-diazaspiro[5.5]undecan-3-ones. *J. Med. Chem.*, 26:855-861.

DeClerck, et al. 1987. Increase in slow-wave sleep in humans with the serotonin-S$_2$ antagonist ritanserin. *Current Therapeutic Research*, 41(4):427-432.

Durif, et al. 1997. Low-dose clozapine improves dyskinesias in Parkinson's disease. *Neurology*, 48:658-662.

Eichelbaum, et al. 1996. Influence of pharmacogenetics on drug disposition and response. *Clinical and Experimental Pharmacology and Physiology*, 23:983-985.

Ermakov, et al. 1981. Use of Mass spectrometry in structural and stereochemical studies. *Chemistry of Heterocyclic Compounds*, 1:72-77.

Everett, et al. 1970. L-Dopa: Effect on concentrations of dopamine, norepinephrine, and serotonin in brains of mice. *Science*, 168:849-850.

Fišera, et al. 1994. Synthesis of spiro-substituted 1,3-oxazines by a new sequence leading to spiroheterocycles. *Monatshefte für Chemie*, 125:909-919.

Friedman, et al. 1999. Low-dose clozapine for the treatment of drug-induced psychosis in Parkinson's disease. *N. Engl. J. Med.*, 340(10):757-763.

Friedman, et al. 2000. Atypical antipsychotics in the treatment of drug-induced psychosis in Parkinson's disease. *Movement Disorders*, 15(2):201-211.

Fuller, R. W. 1982. Drugs acting on serotonergic neuronal systems. In N. N. Osborne (Ed.), *Biology of Serotonenergic Transmission*, Chap. 9, pp. 221-247. New York: Wiley.

Gainetdinov, et al. 2001. Genetic animal models: Focus on schizophrenia. *Trends in Neurosciences*, 24(9)527-533.

Gamma, et al. 2000. 3,4-Methylenedioxymethamphetamine (MDMA) modulates cortical and limbic brain activity as measured by [H$_2$$^{15}$O]-PET in healthy humans. *Neuropsychopharmacology*, 23(4):388-395.

Gawley, R. E., & Aubé, J. 1996. *Principles of Asymmetric Synthesis*. New York: Pergamon.

Gershon, M. D., Mawe, G. M., & Branchek, T. A. 1989. 5-Hydroxytryptamine and enteric neurones. In J. R. Fozard (Ed.), *The Peripheral Actions of 5-Hydroxytryptamine* (pp. 247-273). New York: Oxford University Press.

Gillman, P. K. 2005. Monoamine oxidase inhibitors, opioid analgesics and serotonin toxicity. *British Journal of Anaesthesia*, 95(4):434-441.

Gstach, et al. 1990. Rearrangement of 3,3-disubstituted 1-aryl-4,5-dihydro-5-oxo-3*H*-1,2,4-triazolium tetrafluoroborates; Part 1. A versatile synthesis of 1,5-disubstituted 2-aryl-1,2-dihydro-3*H*-1,2,4-triazol-3-one tetrafluoroborates. *Synthesis*, pp. 803-808.

Idzikowski, et al. 1991. A dose response study examining the effects of ritanserin on human slow wave sleep. *Br. J. Clin. Pharmac.*, 31:193-196.

Julius, et al. 1990. The 5HT2 receptor defines a family of structurally distinct but functionally conserved serotonin receptors. *Proc. Natl. Acad. Sci. USA*, 87:928-932.

Kanayama, et al. 2005. New treatment of lumbar disc herniation involving 5-hydroxytryptamine$_{2A}$ receptor inhibitor: A randomized controlled trial. *J. Neurosurg: Spine*, 2:441-446.

Landolt, et al. 1999. Serotonin-2 receptors and human sleep: Effect of a selective antagonist on EEG power spectra. *Neuropsychopharmacology*, 21(3):455-466.

Leysen, et al. 1978. Serotonergic component of neuroleptic receptors. *Nature*, 272:168-171.

Liechti, et al. 2001. Effects of MDMA (ecstasy) on prepulse inhibition and habituation of startle in humans aftre pretreament with Citalopram, Haloperidol, or Ketanserin. *Neuropsychopharmacology*, 24(3):240-252.

Linder, et al. 1997. Pharmacogenetics: A laboratory tool for optimizing therapeutic efficiency. *Clinical Chemistry*, 43(2):254-266.

Mansbach, et al. 1988. Dopaminergic stimulation disrupts sensorimotor gating in the rat. *Psychopharmacology*, 94:507-514.

Marek, et al. 2003. Synergistic action of 5-HT$_{2A}$ antagonists and selective serotonin reuptake inhibitors in neuropsychiatric disorders. *Neuropsychopharmacology*, 28:402-412.

Marek, et al. 2005. The selective 5-HT$_{2A}$ receptor antagonist M100907 enhances antidepressant-like behavioral effects of the SSRI fluoxetine. *Neuropsychopharmacology*, 30:2205-2215.

Mavunkel, et al. 1996. Synthesis and characterization of pseudopeptide bradykinin B2 receptor antagonists containing the 1,3,8-triazaspiro[4.5]decan-4-one ring system. *J. Med. Chem.*, 39:3169-3173.

Mayer, et al. 2003. Ritanserin improves sleep quality in narcolepsy. *Pharmacopsychiatry*, 36:150-155.

Meltzer, et al. 1995. Plasma clozapine levels and the treatment of L-DOPA-induced psychosis in Parkinson's disease. *Neuropsychopharmacology*, 12(1):39-45.

Meng, et al. 1991. Synthetic approaches toward glidobamine, the core structure of the glidobactin antibiotics. *Tetrahedron*, 47(32):6251-6264.

Miyata, et al. 2000. Sarpogrelate, a selective 5-HT$_{2A}$ serotonergic receptor antagonist, inhibits serotonin-induced coronary artery spasm in a porcine model. *Journal of Cardiovascular Pharmacology*, 35(2) 294-301.

Moulignier, A. 1994. Récepteurs centraux de la sérotonine principaux aspects fondamentaux et fonctionnels application thérapeutiques. *Rev. Neurol.*, 150:3-15.

Mullen et al. 2000. (−)-Spiro[1-azabicyclo[2.2.2]octane-3,5′-oxazolidin-2′one], a conformationally restricted analogue of acetylcholine, is a highly selective full agonist at the α7 nicotinic acetylcholine receptor. *J. Med. Chem.*, 43:4045-4050.

Ng, et al. 1970. L-dopa-induced release of cerbral monoamines. *Science*, 170:76-77.

Nigam, et al. 1957a. Studies with acetylenes. Part II. Some reactions of Grignard reagents with propargylic halides. Model linoleic and linolenic acid systems. *J. Chem Soc.*, pp. 3868-3873.

Nigam, et al. 1957b. The conversion of fatty acids into aldehydes. *J. Chem. Soc.*, pp. 3320-3321.

Nordstrom, et al. 1993. High 5-HT$_2$ receptor occupancy in clozapine treated patients demonstrated by PET. *Psychopharmacology*, 110:365-367.

Ogawa, et al. 2005. Effects of R-102444 and its active metabolite R-96544, selective 5-HT$_{2A}$ receptor antagonists, on experimental acute and chronic pancreatitis: Additional evidence for possible involvement of 5-HT$_{2A}$ receptors in the development of experimental pancreatitis. *European Journal of Pharmacology*, 521:156-163.

Pace, et al. 1991. A mutant α subunit of G$_{12}$ induces neoplastic transformation of Rat-1 cells. *Proc. Natl. Acad. Sci. USA*, vol. 88:7031-7035.

Paiva, et al. 1988. Effects of ritanserin on sleep disturbances of dysthymic patients. *Psychopharmacology*, 96:395-399.

Patel, et al. 2004. The highly selective 5-hydroxytryptamine (5-HT)$_{2A}$ receptor antagonist, EMD 281014, significantly increases swimming and decreases Immobility in male congenital learned helpless rats in the forced swim test. *Synapse*, 52:73-75.

Pierce, et al. 1995. 5-hydroxytryptamine-induced synovial plasma extravasation is mediated via 5-hydroxytryptamine2A receptors on sympathetic efferent terminals. *The Journal of Pharmacology and Experimental Therapeutics*, 275(1):502-508.

Pollak, et al. 1999. Clozapine in drug-induced psychosis in Parkinson's disease. *The Lancet*, 353:2041-2042.

Sadzot, et al. 1989. Hallucinogenic drug interactions at human brain 5-HT$_2$ receptors: Implications for treating LSD-induced hallucinogenesis. *Psychopharmacology*, 98:495-499.

Schins, et al. 2003. Increased coronary events in depressed cardiocascular patients: 5-HT$_{2A}$ receptor as missing link? *Psychosomatic Medicine*, 65:729-737.

Sharpley, et al. 1994. Slow wave sleep in humans: Role of 5-HT$_{2A}$ and 5-HT$_{2C}$ receptors. *Neuropharmacology*, 33(3/4):467-471.

Smith, et al. 1995. New spiropiperdines as potent and selective non-peptide tachykinin NK$_2$ receptor antagonists. *J. Med. Chem.*, 38(19):3772-3779.

Stryjer, et al. 2003. Treatment of neuroleptic-induced akathisia with the 5-HT$_{2A}$ antagonist trazodone. *Clinical Neuropharmacology*, 26(3):137-141.

Tsukamoto, et al. 1995. Synthesis and structure-activity studies of a series of 1-oxa-2,8-diazaspiro[4.5]decan-3-ones and related compounds as M$_1$ muscarinic agonists. *Chem. Pharm. Bull.*, 43(9):1523-1529.

Vallar, et al. 1987. Altered G$_S$ and adenylate cyclase activity in human GH-secreting pituitary adenomas. *Nature*, 330:566-568.

Van Laar, et al. 2001. Subchronic effects of the GABA-agonist lorazepam and the 5-HT$_{2A/2C}$ antagonist ritanserin on driving performance, slow wave sleep and daytime sleepiness in healthy volunteers. *Psychopharmacology*, 154:189-197.

Viola, et al. 2002. Ritanserin, a serotonin-2 receptor antagonist, improves ultradian sleep rhythmicity in young poor sleepers. *Clinical Neurophysiology*, 113:429-434.

Notice of Allowability, Notice of Allowance and Fee(s) Due, and Interview Summary dated Dec. 15, 2006, from U.S. Appl. No. 11/154,083, filed Jun. 16, 2005.

Clifton, et al. 1982. Arylethanolamines Derived from Salicyclamide with α- and β-Adrenoceptor Blocking Activities. Preparation of Labetalol, its Enantiomers, and Related Salicyclamides. *J. Med. Chem.*, 25:670-679.

Delecluse, et al. 1998. A case of tardive tremor successfully treated with clozapine. *Movement Disorders*, 13(5):846-847.

Factor, et al. 1992. Clozapine prevents recurrence of psychosis in Parkinson's disease. *Movement Disorders*, 7(2):125-131.

Factor, et al. 2001. Clozapine for the treatment of drug-induced psychosis in Parkinson's disease: Results of the 12 week open label extension in the Psyclops trial. *Movement Disorders*, 16(1):135-139.

Friedman, J. H. 1994. Clozapine treatment of psychosis in patients with tardive dystonia: Report of three cases. *Movement Disorders*, 9(3):321-324.

Harper, et al. 1964. The chemistry and pharmacology of some 4-aminopiperidines and their derivatives. *J. Med. Chem.*, 44:729-732.

Herrick-Davis, et al. 2000. Inverse agonist activity of atypical antipsychotic drugs at human 5-hydroxytryptamine2C receptors. *The Journal of Pharmacology and Experimental Therapeutics*, 295(1):226-232.

Möhrle, et al. 1990. Sodium mercury edetate dehydrogenation of N-aliphatic substituted 1,2,3,6-tetrahydropyridine derivatives. *Arch. Pharm.* (Weinheim), 323:109-115.

Wade, et al. 2000. Application of base cleavable safety catch linkers to solid phase library production. *J. Comb. Chem.*, 2(3):266-275.

Yoshida, et al. 1998. Marked improvement of tardive dystonia after replacing haloperidol with risperidone in a schizophrenic patient. *Clinical Neuropharmacology*, 21(1):68-69.

Notice of Allowance and Fee(s) Due and Notice of Allowability dated May 15, 1997, from U.S. Appl. No. 08/273,669, filed Jul. 12, 1994, now U.S. Pat. No. 5,707,798.

Office Action dated Mar. 27, 1998, from U.S. Appl. No. 08/954,724, filed Oct. 20, 1997, now U.S. Pat. No. 5,912,132.

Notice of Allowance and Fee(s) Due and Notice of Allowability dated Sep. 4, 1998, from U.S. Appl. No. 08/954,724, filed Oct. 20, 1997, now U.S. Pat. No. 5,912,132.

Office Action dated Sep. 14, 1998, from U.S. Application No. 08/965,947, filed Nov. 7, 1997, now U.S. Pat. No. 5,955,281.

Interview Summary dated Nov. 17, 1998, from U.S. Appl. No. 08/965,947, filed Nov. 7, 1997, now U.S. Pat. No. 5,955,281.

Office Action dated Apr. 25, 2002, from U.S. Appl. No. 09/800,096, now U.S. Pat. No. 6,815,458.

Office Action dated Jan. 21, 2003, from U.S. Appl. No. 09/800,096, now U.S. Pat. No. 6,815,458.

Office Action dated Jul. 15, 2003, from U.S. Appl. No. 09/800,096, now U.S. Pat. No. 6,815,458.

Notice of Allowability dated Dec. 8, 2003, from U.S. Appl. No. 09/800,096, filed Mar. 6, 2001, now U.S. Pat. No. 6,815,458.

Notice of Allowance and Fee(s) Due and Notice of Allowability dated Dec. 5, 2003, from U.S. Appl. No. 10/409,782, filed Apr. 7, 2003, now U.S. Pat. No. 6,756,393.

International Preliminary Examination Report dated Mar. 18, 2003, for PCT/US01/07187.

Office Action dated Feb. 28, 2001, from U.S. Appl. No. 09/413,626, filed Oct. 6, 1999, now U.S. Pat. No. 6,358,698.

Notice of Allowance and Fee(s) Due and Notice of Allowability dated Nov. 20, 2001, from U.S. Appl. No. 09/413,626, filed Oct. 6, 1999, now U.S. Pat. No. 6,358,698.

Specification from U.S. Appl. No. 11/417,070, filed May 3, 2006.
Specification from U.S. Appl. No. 11/417,083, filed May 3, 2006.

Notice of Allowance and Fee(s) Due and Notice of Allowability dated Feb. 11, 2005, from U.S. Appl. No. 10/329,719, filed Dec. 23, 2002, now U.S. Pat. No. 6,911,452.

Office Action dated Jun. 26, 2006, from U.S. Appl. No. 11/154,083, filed Jun. 16, 2005.

Office Action dated Oct. 5, 2006, from U.S. Appl. No. 11/418,322, filed May 3, 2006.

Written Opinion dated Sep. 9, 2003, for PCT/US02/41476.

International Preliminary Examination Report dated Jan. 15, 2004, for PCT/US02/41476.

Office Action dated Nov. 4, 2004, from U.S. Appl. No. 10/601,070, filed Jun. 20, 2003.

Notice of Allowance and Fee(s) Due and Notice of Allowability dated Jul. 12, 2005, from U.S. Appl. No. 10/601,070, filed Jun. 20, 2003.

Notice of Allowance and Fee(s) Due and Notice of Allowability dated Mar. 29, 2006, from U.S. Appl. No. 10/601,070, filed Jun. 20, 2003.

Written Opinion for PCT/US03/19797 dated Apr. 5, 2004.
Specification from U.S. Appl. No. 11/416,527, filed May 3, 2006.
Specification from U.S. Appl. No. 11/416,855, filed May 3, 2006.

International Search Report for PCT/US2004/001234 dated Sep. 8, 2004.

International Written Opinion for PCT/US2004/001234 dated Sep. 8, 2004.

International Preliminary Report on Patentability for PCT/US2004/001234 dated Apr. 14, 2005.

Written Opinion of the International Searching Authority for PCT/US2005/034813 dated Jan. 30, 2006.

Written Opinion of the International Searching Authority for PCT/US2005/034376 dated Jan. 30, 2006.

Kalgutkar, et al. *Selective Inhibitors of Monoamine Oxidase (MAO-A and MAO-B) as Probes of its Catalytic*, XP002034298, Medicinal Research Reviews, vol. 15, No. 4, 325-388 (1988).

International Search Report for corresponding PCT Application No. PCT/US03/19797.

International Preliminary Examination Report for corresponding PCT Application No. PCT/US03/19797.

Alvisi, Sulla formazione di derivati pirazolici dalle dicloridrine e dalla tribromidrina della glicerina ordinaria, Gazz. Chem. Ital. 22:59 (1892).

Antilla & Buchwald, Copper-catalyzed coupling of arylboronic acids and amines, Org. Lett. 3:2077-2079 (2001).

Antilla, et al., The copper-catalyzed N-arylation of indoles, J. Am. Chem. Soc. 124:11684-11688 (2002).

Artico, et al., Aromatic hydrazides as specific inhibitors of bovine serum amine oxidase, Europ. J. Med. Chem. Chim. Ther. 27:219-228 (1992).

Barchas, et al., Serotonin and Behavior (1973).

Barnes and Sharp, A review of central 5-HT receptors and their function, Neuropharmacology, 38:1083-1152 (1999).

Barr, D.R., Manning, A.J., Agonist-independent activation of $G_z$ by the 5-hydroxytryptamine$_{1A}$ receptor co-expressed in *Spodoptera frugiperda* cells, Biol. Chem. 272:32979-87 (1997).

Biagi et al., Farmaco Ed. Sci. 43:597-612 (1988).

Bond et al., Physiological effects of inverse agonists in transgenic mice with myocardial overexpression of the $\beta_2$-adrenoceptor, Nature 374:272 (1995).

Brown et al., Catalytic alkylation of aniline, J. Am. Chem. Soc., 46:1836-1838 (1924).

Büchi and Wüest, Synthesis of (±)-nuciferal, J. Org. Chem. 34:1122-1123 (1969).

Buu-Hoi et al., Further studies in the alkylation of phenols and thiophenols, J. Org. Chem. 16:988 (1951).

Cacchi et al., Palladium-catalyzed reaction of aryl iodides with acetic anhydride. A carbon monoxide free synthesis of acetophenones, Org. Lett. 5:289-293 (2003).

Carman R.M. et al., A further synthesis of an analogue of the antifuncal/antiherbivore lipid from avocado, Aust. J. Chem. 51:955 (1998).

Carroll et al., Synthesis and muscarinic receptor activity of ester derivatives of 2-substituted 2-azabicyclo[2.2.1]heptan-5-ol and -6-ol, J. Med. Chem. 35:2184-91 (1992).

Catarzi et al., Synthesis, ionotropic glutamate receptor binding affinity, and structureactivity relationships of a new set of 4,5-dihydro-8-heteroaryl-4-oxo-1,2,4-triazolo[1,5-α]quinoxaline-2-carboxylates analogues of TQX-0173, J. Med. Chem. 44:3157-3165 (2001).

Cerione et al., The mammalian $\beta_2$-adrenergic receptor: reconstitution of functional interactions between pure receptor and pure stimulatory nucleotide binding protein of the adenylate cyclase system, Biochemistry 23:4519-25 (1984).

Brann, Identification of ligands by selective amplification of cells transfected with receptors and marker enzymes, Chem. Abstr. 128:111548 (1998).

Cherkasov et al., Organothiophsphorus reagents in organic synthesis, Tetrahedron 41:2567 (1985).

Dunn et al., Analgetic and antiinflammatory 7-aroylbenzofuran-5-ylacetic acids and 7-aroylbenzothiophene-5-ylacetic acids, J. Med. Chem. 29:2326 (1986).

Emerson, W.S. and Walters, P.J., The reductive alkylation of aniline, J. Am. Chem. Soc. 60:2023 (1938).

Finar, I.L. and Godfrey, K.E., The preparation and properties of some derivatives of 1-phenylpyrazole, J. Chem. Soc. 2293 (1954).

Glennon, Serotonin receptors: clinical implications, Neurosci. Biobehavioral Rev. 14:35 (1990).

Gooβen, L.J. and Ghosh, K., Palladium-catalyzed synthesis of aryl ketones from boronic acids and carboxylic acids or anhydrides, Angew. Chem. Int. Ed. Engl. 40:3458-3460 (2001).

Guthrie et al., The tetrahedral intermediate from the hydration of N-methylformanilide, Can. J. Chem. 71:2109-2122 (1993).

Hartwig, Transition metal catalyzed synthesis of arylamines and aryl ethers from aryl halides and triflates: scope and mechanism, Angew. Chem. Int. Ed. 37:2046-2067 (1998).

Hickinbottom, The preparation of secondary alkylaryl-amines and their purification, J. Chem. Soc. 992 (1930).

Hirst, H.R. and Cohen, J.B., A method for preparing the formyl derivatives of the aromatic amines, J. Chem. Soc. 67:829 (1895).

Jaeger, et al., Two ketones of the stilboestrol group, J. Chem. Soc. 744-747 (1941).

Klapars, et al., A general and efficient copper catalyst for the amidation of aryl halides, J. Am. Chem. Soc. 124:7421-7428 (2002).

Klapars, et al., A general and efficient copper catalyst for the amidation of aryl halides and the N-arylation of nitrogen heterocycles, J. Am. Chem. Soc. 123:7727-7729 (2001).

Kuehne et al., Enantioselective syntheses of vinblastine, leurosidine, vincovaline, and 20'-epi-vincovaline, J. Org. Chem. 56:513 (1991).

Kuehne et al., Total syntheses of Yohimbe alkaloids, with stereoselection for the normal, allo, and 3-epiallo series, based on annelations of 4-methoxy-1,2-dihydropyridones, J. Org. Chem. 56:2701 (1991).

Kwong et al., A general, efficient, and inexpensive catalyst system for the coupling of aryl iodides and thiols, Org. Lett. 4:3517-3520 (2002).

Kwong, et al., Copper-catalyzed coupling of alkylamines and aryl iodides: an efficient system even in an air atmosphere, Org. Lett. 4:581-584 (2002).

Kwong et al., Mild and efficient copper-catalyzed amination of aryl bromides and primary alkylamines, Org. Lett. 5:793-796 (2003).

Landini et al., A convenient synthesis of primary and secondary dialkyl and aryl alkyl sulfides in the presence of phase-transfer catalysts, Synthesis 565-566 (1974).

Li, Highly active, air-stable palladium catalysts for the c-c and c-s bond-forming reactions of vinyl and aryl cholrides: use of commercially available [(t-Bu)$_2$P(OH)]$_2$PdCl$_2$, [(t-Bu)$_2$P(OH)$_2$PdCl$_2$]$_2$, and [[(t-Bu)$_2$PO...H...OPdCl]$_2$ catalysts, J. Org. Chem. 67:3643-3650 (2002).

Lowe et al., Aza-tricyclic substance P antagonists, , J. Med. Chem. 37:2831-40 (1994).

Meltzer, The role of serotonin in antipsychotic drug action, Neuropsychopharmacology, 21:160S-115S (1999).

Micovic et al., A simple method for preparation of secondary aromatic amines, Synthesis 11:1043-1045 (1991).

Moulignier, Recepteurs centraux de al serotonine principaux aspects fondamentauz et fonctionnels applications therapeutiques, Rev. Neurol. 150:3-15 (1994).

Moune et al., Total synthesis of dolatrienoic acid: a subunit of dolastatin 14, J. Org. Chem. 62:3332-3339 (1997).

Muri et al., Synthesis of new benzylic ethers of oximes derived from 1-phenyl-pyrazole compounds, Synth. Commun. 28:1299-1321 (1998).

Nigam et al., The conversion of fatty acids into aldehydes, J. Chem. Soc. 2000 (1957).

Olah et al., Notiz uber die n-formylierung von aminen mit formylfluorid, Chem. Ber. 89:2211 (1956).

Old, et al., Efficient palladium-catalyzed n-arylation of indoles, Org. Lett. 2:1403-1406 (2002).

Read, Researches on hydantoins. Synthesis of the soporific, 4,4-phenylethyl-hydantoin (nirvanol), J. Am. Chem. Soc. 44:1746-1755 (1922).

Ricci, Ed.; Wiley-VCH: Weinheim, Germany (2000).

Rice et al., Raney nickel catalyzed n-alkylation of aniline and benzidine with alcohols, J. Am. Chem. Soc. 77:4052 (1955).

Rubiralta et al., Piperidine—Structure, Preparation, Reactivity and Synthetic Applications of Piperidine and its Derivatives, Studies in Organic Chemistry 43, Elsevier (1991).

Saltzman et al., Cloning of the human serotonin 5-HT2 and 5-HTIC receptor sybtypes, Biochem. Biophys. Res. Comm. 181:1469 (1991).

Saxena, et al., Cardiovascular effects of serotonin agonists and antagonists, J. Cardiovascular Pharmacol. 15: Supp. 7 (1990).

Scheibye et al., Studies on organophosphorus compounds XXI. The dimer of p-methoxyphenylthionophosphine sulfide as thiation reagent. A new route to thiocarboxamides, Bull. Soc. Chim. Belg. 87:229 (1978).

Screttas et al., Hydrolithiation of α-olefins by a regiospecific two-step process. Transformation of alkyl phenyl sulfides to alkyllithium reagents, J. Org. Chem. 43:1064-1071 (1978).

Stefancich et al., Agenti antiinfiammatori non-steroidei: Nota III—sintesi ed attivita analgesica-antiinfiammatoria de 4-(pirrol-1-il)-fenilacetamidi e di 4-(pirrol-1-il)fenetilamine, Farmaco Ed. Sci. 39:752-764 (1984).

Varma et al., Microwave-accelerated solvent-free synthesis of thioketones, thiolactones, thioamides, thionoesters, and thioflavonoids, Org. Lett. 1: 697-700 (1999).

Vogel, Physical properties and chemical constitution. Part XIX. Five-membered and six-membered carbon rings, J. Chem. Soc. 1809 (1948).

Vogl et al., Palladium-catalyzed monoarylation of nitroalkanes, J. Org. Chem. 67:106-111 (2002).

Weiner et al., 5-hydroxytryptamine$_{2A}$ receptor inverse agonists as antipsychotics, J. Pharmacol. Exp. Ther. 299(1):268-276 (2001).

Whitmore et al., Abnormal Grignard reactions. XII. Sterically hindered aliphatic carbonyl compounds. II. Ketones containing the dineopentylcarbinyl group, J. Am. Chem. Soc. 64:1247 (1942).

Whitmore et al., Higher hydrocarbons. IV. Six phenylicosanes and six cyclohexyleicosanes, J. Am. Chem. Soc. 69:235-237 (1947).

Wolf, Uber alkin-amine I. Aryl-propargyl-amine, Liebigs Ann. Chem. 576:35-45 (1952).

Wolfe et al., An improved catalyst system for aromatic carbon-nitrogen bond formation: the possible involvement of bis(phosphine) palladium complexes as key intermediates, J. Am.Chem. Soc., 1996, 118, 7215-7216.

Yamada et al., Tetrahedron Lett. 39:7709-7712 (1998).

Yang et al., Palladium-catalyzed amination of aryl halides and sulfonates, J. Organometallic Chem. 576:125-146 (1999).

Yasuhara et al., An activated phosphate for an efficient amide and peptide coupling reagent, J. Chem. Soc. Perkin Trans. 1 17:2901-2902 (2000).

Yin et al., Pd-catalyzed intermolecular amidation of aryl halides: the discovery that xantphos can be trans-chelating in a palladium complex, J. Am. Chem. Soc. 124:6043-6048 (2002).

Alvisi, N. 1892. Sulla formazione di derivati pirazolici dalle dicloridrine e dalla tribromidrina della glicerina ordinaria, Gazz. Chem. Ital. 22:158-168.

Archibald, et al., 1974 "Benzamidopiperidines. 2. Heterocyclic Compounds Related to Indoramin" J. Medicinal Chemistry, 17(7):736-739.

Archibald, et al., 1974 "Benzamidopiperidines. 3. Heterocyclic Compounds Related to Indoramin" J. Medicinal Chemistry, 17(7):-739-744.

Archibald, et al., 1974 "1,4-Bis-(2-indol-3-ylethyl)piperdines" J. Medicinal Chemistry, 17(7):-745-747.

Bassus, et al. 1974. Psychotropes potentiels. X. Synthèse de butyrophénones à cycle pipéridine-spiro-tétrahydrooxazinone douées d'activité neuroleptique. Eur. J. Med. Chem.—Chimica Therapeutica, 9(4):416-423.

Irikura et al., 1971 "New Anticulcer Agents. 1. Synthesis and Biological Activities of 1-Acyl-2-,-3-, -4-substituted Benzamidopiperdines" J. Medicinal Chemistry 14(4): 357-361.

Finar, et al. 1954. The preparation and properties of some derivatives of 1-phenylpyrazole, J. Chem. Soc., pp. 2293-2298.

Oláh, et al. 1956. Notiz über die N-formylierung von aminen mit formylfluorid. Chem. Ber., 89:2211-2212.

Stefancich, et al. 1984. Agenti antiinfiammatori non-steroidei: Nota III—sintesi ed attività analgesica-antiinfiammatoria di 4-(pirrol-1-il)-fenilacetamidi e di 4-(pirrol-1-il)fenetilamine. Farmaco Ed. Sci., 39(9):752-764.

Tolstikov et al.1991 "Synthesis and Reactivity of N-substituted aminoamides, antiarrhythmic and local anaesthetic activity" Russian Chemical Reviews 60(4):420434.

Wolf, V. V. 1952. Über alkin-amine I. Aryl-propargyl-amine. Liebigs Ann. Chem., 576:35-45.

International Preliminary Report on Patentability dated Mar. 27, 2007, for PCT/US2005/034813.

International Preliminary Report on Patentability dated Mar. 27, 2007, for PCT/US2005/034376.

Office Action dated Apr. 6, 2007, from U.S. Appl. No. 11/418,322, filed May 3, 2006.

Office Action dated May 8, 2007, from U.S. Appl. No. 11/417,866, filed May 3, 2006.

Ermakov, et al. 1981. Use of Mass spectrometry in structural and stereochemical studies. Chemistry of Heterocyclic Compounds, 1:72-77.

Notice of Allowance and Fee(s) Due and Notice of Allowability dated Mar. 5, 2007, from U.S. Appl. No. 10/601,070, filed Jun. 20, 2003.

Notice of Allowance and Fee(s) Due and Notice of Allowability dated Jun. 19, 2007, from U.S. Appl. No. 11/418,322, filed May 3, 2006.

Ryckmans, et al., First Dual NK Antagonists-Serotonin Reuptake Inhibitors: Synthesis and SAR of a New Class of Potential Antidepressants. Bioorganic & Medicinal Chemistry Letters, (2002), 12:261-264.

Thomas, et al. 1997. "Rapid in-plate generationof benzimidazole libraries and amide formation using EEDQ," Tetrahedron Lett. 39(29):5099-5102.

Office Action dated Oct. 10, 2007, from U.S. Appl. No. 10/759,561, filed Jan. 15, 2004.

Office Action dated Oct. 12, 2007 from U.S. Appl. No. 11/417,439, filed May 3, 2006.

Office Action dated Oct. 22, 2007 from U.S. Appl. No. 11/417,782, filed May 3, 2006.

Office Action dated Oct. 26, 2007, from U.S. Appl. No. 11/417,866, filed May 3, 2006.

Office Action dated Jan. 25, 2008, from U.S. Appl. No. 10/802,970, filed Mar. 16, 2004.

Office Action dated Jan. 30, 2008, from U.S. Appl. No. 11/417,790, filed May 3, 2006.

Office Action dated Feb. 22, 2008, from U.S. Appl. No. 11/417,866, filed May 3, 2006.

Office Action dated Mar. 28, 2008, from U.S. Appl. No. 11/417,782, filed May 3, 2006.

Office Action dated Jul. 14, 2006, from U.S. Appl. No. 10/601,070, filed Jun. 20, 2003.

Supplemental Notice of Allowability dated May 23, 2008, from U.S. Appl. No. 11/417,439, filed May 3, 2006.

Office Action dated Jun. 2, 2008, from U.S. Appl. No. 11/687,552, filed Mar. 16, 2007.

International Search Report dated Jul. 17, 2001 for PCT/US01/07187.

Written Opinion dated Nov. 22, 2002 for PCT/US01/07187.

Office Action dated May 21, 2004, from U.S. Appl. No. 10/329,719, filed Dec. 23, 2002, now U.S. Pat. No. 6,911,452.

Office Action dated Jan. 17, 2006, from U.S. Appl. No. 11/154,083, filed Jun. 26, 2005.

Office Action dated Jan. 23, 2007, from U.S. Appl. No. 11/418,322, filed May 3, 2006.

International Search Report dated May 8, 2003 for PCT/US02/41476.

International Search Report dated Jan. 30, 2006, for PCT/US2005/034813.

International Search Report dated Jan. 30, 2006, for PCT/US2005/034376.

N-SUBSTITUTED PIPERIDINE DERIVATIVES AS SEROTONIN RECEPTOR AGENTS

RELATED APPLICATIONS

The present application is a continuation of U.S. application Ser. No. 10/601,070, filed Jun. 20, 2003, now U.S. Pat. No. 7,253,186 by Andersson et al., and entitled "N-SUBSTITUTED PIPERIDINE DERIVATIVES AS SEROTONIN RECEPTOR AGENTS," which in turn claims priority to U.S. Provisional Application Ser. No. 60/391,269, filed Jun. 24, 2002, by Andersson, and entitled "N-(HETEROCYCLYLALKYL)PIPERIDINE DERIVATIVES AS SEROTONIN RECEPTOR AGENTS," the entire disclosure of which including any drawings, is hereby incorporated by reference herein.

FIELD OF THE INVENTION

The present invention relates to azacyclic compounds with pharmacokinetic properties for the treatment of symptoms, diseases and disorders associated with monoamine receptors, including serotonin receptors.

BACKGROUND OF THE INVENTION

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, and controlling body temperature and blood pressure. In the spinal column, serotonin plays an important role in the control systems of the afferent peripheral nociceptors (Moulignier, *Rev. Neurol.* 150:3-15, (1994)). Peripheral functions in the cardiovascular, hematological, and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission,* 1982; Boullin, *Serotonin In Mental Abnormalities* 1:316 (1978); Barchas, et al., *Serotonin and Behavior,* (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., *The Peripheral Actions of 5-Hydroxytryptamine,* 246 (1989); Saxena, et al., *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology,* 21:106S-115S (1999); Barnes & Sharp, *Neuropharmacology,* 38:1083-1152 (1999); Glennon, *Neurosci. Biobehavioral Rev.,* 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of these adverse effects.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects. Antagonism of 5-HT2A is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects.

Traditionally, these receptors have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

The present investigators have recently elucidated an important aspect of 5-HT2A receptor function by applying the Receptor Selection and Amplification Technology (U.S. Pat. No. 5,707,798, 1998; Chem Abstr. 128:111548 (1998) and citations therein), to the study of the 5-HT2 subclass of serotonin receptors. R-SAT is a phenotypic assay of receptor function that involves the heterologous expression of receptors in mammalian fibroblasts. Using this technology we were able to demonstrate that native 5-HT2A receptors possess significant constitutive, or agonist-independent, receptor activity (U.S. Pat. No. 6,358,698; Weiner et. al. *J. Pharmacol. Exp. Ther.* 2001, 299 (1), 268-276, both of which are hereby incorporated by reference herein in their entirety, including any drawings). Furthermore, by directly testing a large number of centrally acting medicinal compounds with known clinical activity in neuropsychiatric disease, we determined that compounds with antipsychotic efficacy all shared a common molecular property. Nearly all of these compounds, which are used by psychiatrists to treat psychosis, were found to be potent 5-HT2A inverse agonists. This unique clinicopharmacologic correlation at a single receptor subtype is compelling evidence that 5-HT2A receptor inverse agonism is a molecular mechanism of antipsychotic efficacy in humans.

Detailed pharmacological characterization of a large number of antipsychotic compounds revealed that they possess broad activity at multiple related receptor subtypes. Most of these compounds display agonist, competitive antagonist, or inverse agonist activity at multiple monoaminergic receptor subtypes, including serotoninergic, dopaminergic, adrenergic, muscarinic and histaminergic receptors. This broad activity is likely responsible for the sedating, hypotensive, and motor side effects of these compounds. It would therefore be of great advantage to develop compounds that are selective inverse agonists of the 5-HT2A receptor, but which have little or no activity on other monamine receptors subtypes, especially dopamine D2 receptors. Such compounds may be useful in the treatment of human disease (e.g., as anti-psychotics), and may avoid the adverse side effects associated with non-selective receptor interactions.

U.S. Pat. No. 4,853,394 discloses N-(Hydroxyethylpiperid-4-yl) esters and amides which with gastic motility enhancing, anti-emetic activity and 5-HT antagonist activity.

EP 0 260 070 discloses the acetic acid ester of 4-(4-(4-chlorophenyl)-4-hydroxy-1-piperidinyl)-1-(4-fluorophenyl)-1-butanone for the alleviation, palliation, mitigation, or inhibition of the manifestations of psychic abnormalities.

SUMMARY OF THE INVENTION

Disclosed herein are compounds of Formula I,

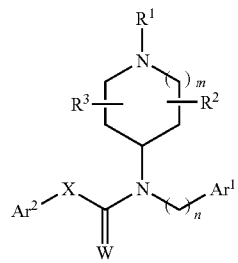

or a pharmaceutically acceptable salt, amide, ester, or prodrug thereof, wherein $R^1$ is selected from the group consisting of optionally substituted heterocyclyl, and optionally substituted (heterocyclyl)$C_{1-6}$-alkyl;

$R^2$ and $R^3$ are independently selected from the group consisting of hydrogen, $C_{1-6}$-alkyl and halogen or such that $R^2$ together with $R^3$ forms a ring;

m is selected from the group consisting of 0, 1, and 2;

n is selected from the group consisting of 1, 2, and 3;

$Ar^1$ is an optionally substituted aryl or heteroaryl;

W is selected from the group consisting of O and S;

X is selected from the group consisting of optionally substituted methylene, optionally substituted ethylene, optionally substituted propylene, optionally substituted vinylene, and $CH_2N(R^N)$, wherein $R^N$ is selected from hydrogen and $C_{1-6}$-alkyl; and $Ar^2$ is an optionally substituted aryl or heteroaryl.

Also disclosed are methods of inhibiting an activity of a monoamine receptor comprising contacting the monoamine receptor or a system containing the monoamine receptor with an effective amount of one or more of the compounds of Formula I. Disclosed are also methods of inhibiting an activation of a monoamine receptor comprising contacting the monoamine receptor or a system containing the monoamine receptor with an effective amount of one or more of the compounds of Formula I. Furthermore, methods of treating psychotic disease using a compound of Formula I are disclosed.

DETAILED DESCRIPTION OF THE INVENTION

For the purpose of the current disclosure, the following definitions shall in their entireties be used to define technical terms, and shall also, in their entireties, be used to define the scope of the composition of matter for which protection is sought in the claims. The term "Constitutive activity" is defined as the basal activity of a receptor which is independent of the presence of an agonist. Constitutive activity of a receptor may be measured using a number of different methods, including cellular (e.g., membrane) preparations (see, e.g., Barr &. Manning, *J. Biol. Chem.* 272:32979-87 (1997)), purified reconstituted receptors with or without the associated G-protein in phospholipid vesicles (Cerione et al., *Biochemistry* 23:4519-25 (1984)), and functional cellular assays (U.S. Pat. No. 6,358,698).

The term "agonist" is defined as a compound that increases the activity of a receptor when it contacts the receptor.

The term "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity.

The term "inverse agonist" is defined as a compound that decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist. The concept of an inverse agonist has been explored by Bond et al. in *Nature* 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, an inverse agonist can additionally manifest its activity in the absence of an agonist by inhibiting the spontaneous conversion of an unliganded receptor to an active conformation.

The term "5-HT2A receptor" is defined as a receptor, having an activity corresponding to the activity of the human serotonin receptor subtype, which was characterized through molecular cloning and pharmacology as detailed in Saltzman et al., *Biochem. Biophys. Res. Comm.* 181:1469-78; and Julius et al., *Proc. Natl. Acad. Sci. USA* 87:928-932.

The term "subject" refers to an animal, preferably a mammal, most preferably a human, who is the object of treatment, observation or experiment.

The term "selective" is defined as a property of a compound whereby an amount of the compound sufficient to effect a desired response from a particular receptor type, subtype, class or subclass causes a substantially smaller or no effect upon the activity other receptor types.

The terms "selectivity" or "selective," in relation to an inverse agonist, are understood as a property of a compound of the invention whereby an amount of compound that effectively inversely agonizes the 5-HT2A receptor, and thereby decreases its activity, causes little or no inverse agonistic or antagonistic activity at other, related or unrelated, receptors. In particular, certain compounds of the invention have been found not to interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. Preferably, the compounds of the invention are also selective with respect to other monoamine-binding receptors, such as the dopaminergic, histaminergic, adrenergic and muscarinic receptors. Compounds that are highly selective for 5-HT2A receptors may have a beneficial effect in the treatment of psychosis, schizophrenia or similar neuropsychiatric disorders, while avoiding adverse effects associated with drugs hitherto suggested for this purpose.

The $EC_{50}$ for an agonist is intended to denote the concentration of a compound needed to achieve 50% of a maximal response seen in R-SAT. For inverse agonists, $EC_{50}$ is intended to denote the concentration of a compound needed to achieve 50% inhibition of an R-SAT response from basal, no compound, levels.

As used herein, the term "coadministration" of pharmacologically active compounds refers to the delivery of two or more separate chemical entities, whether in vitro or in vivo. Coadministration refers to the simultaneous delivery of separate agents; to the simultaneous delivery of a mixture of agents; as well as to the delivery of one agent followed by delivery of a second agent or additional agents. In all cases, agents that are coadministered are intended to work in conjunction with each other.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, preferably benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group may be substituted at the para and/or meta positions. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one $C_{3-8}$-cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, preferably connected via one of the ring-forming carbon atoms. Heteroaryl groups may carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups may be five- and six-membered aromatic heterocyclic systems carrying 0, 1, or 2 substituents, which may be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, which are all preferred, as well as furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, amino-$C_{1-6}$-alkyl.

In the present context, the term "alkyl" and "$C_{1-6}$-alkyl" are intended to mean a linear or branched saturated hydrocarbon chain wherein the longest chain has from one to six carbon atoms, such as methyl, ethyl, n-propyl, isopropyl, n-butyl, isobutyl, sec-butyl, tert-butyl, pentyl, isopentyl, neopentyl, and hexyl. An alkyl chain may be optionally substituted.

The term "heterocyclyl" is intended to mean three-, four-, five-, six-, seven-, and eight-membered rings wherein carbon atoms together with from 1 to 3 heteroatoms constitute said ring. A heterocyclyl may optionally contain one or more unsaturated bonds situated in such a way, however, that an aromatic π-electron system does not arise. The heteroatoms are independently selected from oxygen, sulfur, and nitrogen.

A heterocyclyl may further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings may optionally also be fused to aryl rings, such that the definition includes bicyclic structures. Preferred such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidino, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle may be at the position of a heteroatom or via a carbon atom of the heterocycle, or, for benzo-fused derivatives, via a carbon of the benzenoid ring.

The term "(heterocyclyl)$C_{1-6}$-alkyl" is understood as heterocyclyl groups connected, as substituents, via an alkyl, each as defined herein. The heterocyclyl groups of (heterocyclyl) $C_{1-6}$-alkyl groups may be substituted or unsubstituted. The term "(heterocyclyl)$C_{1-6}$-alkyl" is intended to mean an alkyl chain substituted at least once with a heterocyclyl group, typically at the terminal position of the alkyl chain.

In the present context, the term "$C_{2-8}$-alkenyl" is intended to mean a linear or branched hydrocarbon group having from two to eight carbon atoms and containing one or more double bonds. Some examples of $C_{2-8}$-alkenyl groups include allyl, homo-allyl, vinyl, crotyl, butenyl, pentenyl, hexenyl, heptenyl and octenyl. Some examples of $C_{2-8}$-alkenyl groups with more than one double bond include butadienyl, pentadienyl, hexadienyl, heptadienyl, heptatrienyl and octatrienyl groups as well as branched forms of these. The position of the unsaturation (the double bond) may be at any position along the carbon chain.

In the present context the term "$C_{2-8}$-alkynyl" is intended to mean a linear or branched hydrocarbon group containing from two to eight carbon atoms and containing one or more triple bonds. Some examples of $C_{2-8}$-alkynyl groups include ethynyl, propynyl, butynyl, pentynyl, hexynyl, heptynyl and octynyl groups as well as branched forms of these. The position of unsaturation (the triple bond) may be at any position along the carbon chain. More than one bond may be unsaturated such that the "$C_{2-8}$-alkynyl" is a di-yne or enedi-yne as is known to the person skilled in the art.

In the present context, the term "$C_{3-8}$-cycloalkyl" is intended to cover three-, four-, five-, six-, seven-, and eight-membered rings comprising carbon atoms only. A $C_{3-8}$-cycloalkyl may optionally contain one or more unsaturated bonds situated in such a way, however, that an aromatic π-electron system does not arise.

Some examples of preferred "$C_{3-8}$-cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, cycloheptene.

The terms "(aryl)$C_{1-6}$-alkyl" is intended to mean an aryl group connected, as a substituent, via a $C_{1-6}$-alkyl, each as defined herein. The aryl groups of (aryl)$C_{1-6}$-alkyl may be substituted or unsubstituted. Examples include benzyl, substituted benzyl, 2-phenylethyl, 3-phenylpropyl, and naphthylalkyl.

The terms "(cycloalkyl)$C_{1-6}$-alkyl" is intended to mean a cycloalkyl groups connected, as substituents, via an alkyl, each as defined herein.

When used herein, the term "O—$C_{1-6}$-alkyl" is intended to mean $C_{1-6}$-alkyloxy, or alkoxy, such as methoxy, ethoxy, n-propoxy, isopropoxy, n-butoxy, isobutoxy, sec-butoxy, tert-butoxy, pentyloxy, isopentyloxy, neopentyloxy and hexyloxy The term "halogen" includes fluorine, chlorine, bromine and iodine.

In the present context, i.e. in connection with the terms "$C_{1-6}$-alkyl", "aryl", "heteroaryl", "heterocyclyl", "$C_{3-8}$-cycloalkyl", "heterocyclyl($C_{1-6}$-alkyl)", "(cycloalkyl)alkyl", "O—$C_{1-6}$-alkyl", "$C_{2-8}$-alkenyl", and "$C_{2-8}$-alkynyl", the term "optionally substituted" is intended to mean that the group in question may be substituted one or several times, such as 1 to 5 times, or 1 to 3 times, or 1 to 2 times, with one or more groups selected from $C_{1-6}$-alkyl, $C_{1-6}$-alkoxy, oxo (which may be represented in the tautomeric enol form), carboxyl, amino, hydroxy (which when present in an enol system may be represented in the tautomeric keto form), nitro, alkylsulfonyl, alkylsulfenyl, alkylsulfinyl, $C_{1-6}$-alkoxycarbonyl, $C_{1-6}$-alkylcarbonyl, formyl, amino, mono- and di($C_{1-6}$-alkyl)amino; carbamoyl, mono- and di($C_{1-6}$-alkyl) aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, $C_{1-6}$-alkylhydroxyimino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, heterocyclyl, heteroaryl, and halo. In general, the above substituents may be susceptible to further optional substitution.

The term "salts" is intended to mean pharmaceutically acceptable acid addition salts obtainable by treating the base form of a functional group, such as an amine, with appropriate acids such as inorganic acids, for example hydrohalic acids; typically hydrochloric, hydrobromic, hydrofluoric, or hydroiodic acid; sulfuric acid; nitric acid; phosphoric acid and the like; or organic acids, for example acetic, propionic, hydroacetic, 2-hydroxypropanoic acid, 2-oxopropanoic acid, ethandioic, propanedioic, butanedioic, (Z)-2-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic acid, cyclohexanesulfamic, 2-hydoxybenzoic, 4-amino-2-hydroxybenzoic, and other acids known to the skilled practitioner.

The present invention includes within its scope prodrugs of the compounds of this invention. In general, such prodrugs are inactive derivatives of the compounds of this invention that are readily convertible in vivo into the required compound. Conventional procedures for the selection and preparation of suitable prodrug derivatives are described, for example, in *Design of Prodrugs*, (ed. H. Bundgaard, Elsevier, 1985). Metabolites of these compounds include active species that are produced upon introduction of compounds of this invention into the biological milieu.

Where the compounds according to the invention have at least one chiral center, they may exist as a racemate or as enantiomers. It should be noted that all such isomers and mixtures thereof are included in the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also included in the scope of this invention.

Where the processes for the preparation of the compounds according to the invention give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved using a chiral auxiliary by formation of diastereomeric derivatives such as esters, amides or ketals followed by chromatographic separation and removal of the chiral auxiliary.

The compounds of the present invention are effective upon administration orally. In vivo experiments performed in rodents have indicated that a lower dose of the compounds of the present invention results in equal or improved behavioral responses in animal models of psychosis. These results are indicative of a higher bioavailability of the compounds of the present invention, compared to the compounds disclosed in the prior art. An improved bioavailability is corroborated by the observation that the new compounds presented herein are not significantly more potent when assayed for their effects on serotonin receptors in vitro, and yet represent a substantial improvement when orally administered. The highly improved efficacy observed after oral dosing is probably a result of increased metabolic stability, improved physico-chemical properties, such as solubility or chemical stability, or different pharmacokinetic characteristics, such as distribution, permeability, or the like. Without being bound to a particular theory, it is reasonable to ascribe such differences to the presence of a heterocyclic substituent at the nitrogen of the piperidine ring of these compounds. The presence of such a heterocyclic substituent could affect the behavior of these derivatives in terms of solubility and/or metabolic lability. The presence of heteroatoms in substituents close to the nitrogen would also be suspected to influence the basicity of the nitrogen, which, in turn, might affect properties such as distribution (LogD) or metabolism.

Generally, a high degree of bioavailability of any pharmaceutical is considered highly beneficial. This relates primarily to the ability to be able to administer an efficacious yet safe dose of the drug to all subjects irrespective of their potential predisposition to polymorphism-dependent drug metabolism. Examples of many such polymorphisms are well known in the art. Thus, a drug which undergoes substantial metabolism, either during its first pass through the liver or in the gastrointestinal tract, will display a relatively low, and sometimes dose-dependent, bioavailability measured as the plasma concentration achieved after peroral distribution. Inter-individual differences in drug exposure are generally more severe when a drug is heavily metabolized, and, as a consequence, displays low oral bioavailability. Subjects with polymorphisms resulting in changes in the activity of drug-metabolizing enzymes are likely to become exposed to very different (normally much higher) plasma levels than those displaying a normal metabolic activity. Hence, aspects of the present invention relate to novel compounds which display characteristics suggestive of superior drug properties when compared to those previously known in the art.

In general, compounds of Formula I are active at monoamine receptors, specifically serotonin receptors. Several compounds of the invention share the common property of acting as inverse agonists at the 5-HT2A receptor. Thus, experiments performed on cells transiently expressing the human phenotype of said receptor have shown that the compounds of general Formula I attenuate the signaling of such receptors in the absence of additional ligands acting upon the receptor. The compounds have thus been found to possess intrinsic activity at this receptor and are able to attenuate the basal, non-agonist-stimulated, constitutive signaling responses that the 5-HT2A receptor displays. The observation that the compounds of general Formula I are inverse agonists also indicates that these compounds have the ability to antagonize the activation of 5-HT2A receptors that is mediated by endogenous agonists or exogenous synthetic agonist ligands.

In certain embodiments, the present invention provides compounds that show a relatively high degree of selectivity towards the 5-HT2A subtype of serotonin receptors relative to other subtypes of the serotonin (5-HT) family of receptors as well as to other receptors, most particularly the monoaminergic G-protein coupled receptors, such as dopamine receptors. In other embodiments, the compounds of the present invention act as inverse agonists at the 5-HT2A subtype of serotonin receptors.

The compounds of general Formula I may therefore be useful for treating or alleviating symptoms of disease conditions associated with impaired function, in particular elevated levels of activity, of especially 5-HT2A receptors, whether this impaired function is associated with improper levels of receptor stimulation or phenotypical aberrations.

Others have previously hypothesized that certain neuropsychological diseases might be caused by altered levels of constitutive activity of monoamine receptors. Such constitutive activity might be modified via contacting the relevant receptor with a synthetic inverse agonist. By directly testing a large number of centrally acting medicinal compounds with known clinical activity in neuropsychiatric disease, we determined that compounds with antipsychotic efficacy all shared a common molecular property. Nearly all of these compounds that are used by psychiatrists to treat psychosis were found to be potent 5-HT2A inverse agonists. This correlation is compelling evidence that 5-HT2A receptor inverse agonism is a molecular mechanism of antipsychotic efficacy in humans.

Detailed pharmacological characterization of a large number of antipsychotic compounds in our laboratory revealed that they possess broad activity at multiple related receptor subtypes. Most of these compounds display either agonist, competitive antagonist, or inverse agonist activity at multiple monoaminergic receptor subtypes including serotoninergic, dopaminergic, adrenergic, muscarinic and histaminergic receptors. This broad activity is likely responsible for the sedating, hypotensive, and motor side effects of these compounds. It follows that the compounds disclosed herein will possess efficacy as, for example, novel antipsychotics, but will have fewer or less severe side effects than existing compounds.

Thus, in the first aspect, the present invention relates to a compound of Formula I,

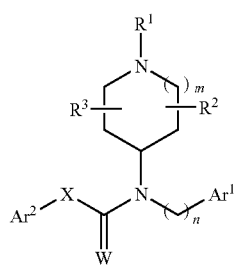

or a pharmaceutically acceptable salt, amide, ester, or prodrug thereof, wherein
  $R^1$ is selected from the group consisting of optionally substituted heterocyclyl, and optionally substituted (heterocyclyl)$C_{1-6}$-alkyl;
  $R^2$ and $R^3$ are independently selected from the group consisting of hydrogen, $C_{1-6}$-alkyl and halogen or such that $R^2$ together with $R^3$ forms a ring;
  m is selected from the group consisting of 0, 1, and 2;
  n is selected from the group consisting of 1, 2, and 3;
  $Ar^1$ is an optionally substituted aryl or heteroaryl;
  W is selected from the group consisting of O and S;
  X is selected from the group consisting of optionally substituted methylene, optionally substituted ethylene, optionally substituted propylene, optionally substituted vinylene, and $CH_2N(R^N)$, wherein $R^N$ is selected from hydrogen and $C_{1-6}$-alkyl; and
  $Ar^2$ is an optionally substituted aryl or heteroaryl.

As discussed, the presence of a heterocyclic substituent at the nitrogen of the piperidine ring of these compounds is considered to improve the bioavailability of the compounds, in comparison to related compounds known to the person skilled in the art.

In some embodiments, the heterocyclyl or (heterocyclyl) $C_{1-6}$-alkyl of $R^1$ may be optionally substituted. The substituent may be selected from halogen, hydroxy, alkyl, alkoxy, and amino. In some embodiments, the substituent may be on the alkyl chain or the ring system. In further embodiments the substituent is on the ring system.

In certain embodiments, the heterocyclyl ring in $R^1$ may be selected from the group consisting of tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidinone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. In some embodiments, the heterocyclyl ring is selected from 1,3-dioxane, 1,3-dioxolane, and tetrahydropyran.

The azacyclic ring may be a 5, 6, or 7-membered ring as reflected in that m may be selected from 0, 1 and 2. In certain embodiments, however, the azacyclic ring is a 6-membered ring, wherein m is 1.

The azacyclic ring, further to being substituted at the nitrogen position, may be substituted with $R^2$ and $R^3$. $R^2$ and $R^3$ may be independently selected from the group consisting of hydrogen, $C_{1-6}$-alkyl, and halogen, or such that $R^2$ together with $R^3$ forms a ring. That is to say that $R^2$ and $R^3$ may be biradicals which combine to form a 3-, 4-, 5-, 6-, or 7-membered ring system with the atoms of the azacyclic ring.

In some embodiments, the azacyclic ring system is selected from

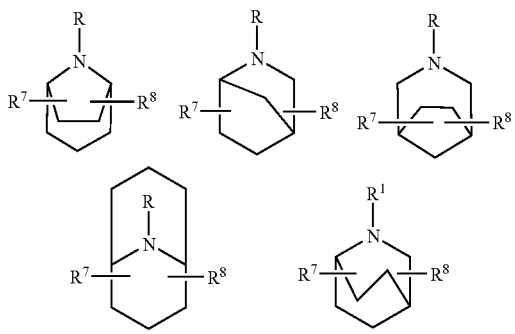

wherein $R^7$ and $R^8$ are independently selected from the group consisting of hydrogen, halogen, hydroxyl, and $C_{1-6}$ alkyl. In certain embodiments $R^7$ and $R^8$ are hydrogen.

In other embodiments, $R^2$ and $R^3$ are hydrogen.

In some embodiments, $R^1$ is an optionally substituted (heterocyclyl)$C_{1-6}$-alkyl. In certain of these embodiments, $R^1$ is an optionally substituted (heterocyclyl)methyl, an optionally substituted (heterocyclyl)ethyl, or an optionally substituted (heterocyclyl)propyl. In other embodiments, $R^1$ is an optionally substituted (heterocyclyl)ethyl.

$Ar^1$ is linked to a central nitrogen atom via a short aliphatic chain 1, 2, or 3 carbon atoms in length. In certain embodiments, n is 1, resulting in a methylene spacer between the central nitrogen atom and $Ar^1$. $Ar^1$ may be an optionally substituted aryl or heteroaryl. In some embodiments, $Ar^1$ is an optionally substituted aryl. In some embodiments, the central nitrogen atom is linked to an optionally substituted benzyl group.

In certain embodiments $Ar^1$ is an optionally substituted aryl, which may be a 4-substituted aryl. The 4-substituent of the 4-substituted aryl may be any substituent known to the person skilled in the art, such as a $C_{1-6}$-alkyl, $C_{1-6}$-alkoxy, carboxyl, amino, hydroxy, thiol, nitro, cyano, guanidino, carbamido and halogen. In some embodiments, the halogen is fluoro, while in other embodiments, the halogen is chloro.

In other embodiments, $Ar^1$ is selected from the group consisting of alkyl-substituted phenyl, alkoxy-substituted phenyl, halogen-substituted phenyl, hydroxy-substituted phenyl and amino-substituted phenyl. In some embodiments, the substituent may be present 0 to 5 times, or 0 to 4 times, or 0 to 3 times, such as 0, 1, 2, or 3 times. In certain embodiments, the substituent is present 1 to 2 times. In some embodiments, $Ar^1$ is a 4-substituted aryl selected from the group consisting of 4-halophenyl and 4-alkylphenyl. In some embodiments, the phenyl group is 4-fluorophenyl.

In other embodiments, $Ar^1$ is an optionally substituted heteroaryl. The heteroaryl may be substituted with substituents known to the person skilled in the art, such as a $C_{1-6}$-alkyl, $C_{1-6}$-alkoxy, carboxyl, amino, hydroxy, thiol, nitro, cyano, guanidino, carbamido and halogen.

Further to being linked to both the azacyclic ring and to $Ar^1$ via a short aliphatic chain, the central nitrogen is linked to $Ar^2$ via a 2 to 4 carbon spacer unit. This spacer unit comprises a carbonyl or thiocarbonyl function wherein W is selected from the group consisting of oxygen and sulfur. In some embodiments W is oxygen.

In certain embodiments, X may be selected from the group consisting of optionally substituted methylene, optionally substituted ethylene, optionally substituted propylene, optionally substituted vinylene, and $CH_2N(R^N)$. Thus X may extend the spacer unit by 1 to 3 atoms between the central nitrogen and $Ar^2$ and render the central nitrogen part of an amide or carbamide. In some embodiments, X is selected from the group consisting of optionally substituted methylene, optionally substituted ethylene, and $CH_2N(R^N)$. In some embodiments, X is an optionally substituted methylene, or $CH_2N(R^N)$, wherein $R^N$ may be hydrogen.

In certain embodiments, $Ar^2$ may be an optionally substituted aryl or heteroaryl. In certain embodiments, $Ar^2$ is an optionally substituted aryl. In some embodiments, $Ar^2$ is a 4-substituted aryl.

In a further embodiment, $Ar^2$ may be selected from the group consisting of alkoxy-substituted phenyl, halogen-substituted phenyl, hydroxy-substituted phenyl, amino-substituted phenyl, and heterocyclyl-substituted phenyl.

In certain embodiments, $Ar^2$ is a 4-substituted aryl wherein the substituent is selected from the group consisting of alkyl, alkoxy, halogen, hydroxy, amino, alkylamino, heterocyclyl, and heteroaryl. In some embodiments, the substituent on $Ar^2$ is selected from chloro, fluoro, hydroxy, methoxy, ethoxy, propoxy, isopropoxy, n-butoxy, sec-butoxy, tert-butoxy, trifluoromethoxy, N-morpholinyl, N-pyrrolidinyl, N-pyrazolyl, N-triazolyl and 2-oxopyrrolidinyl.

In another aspect, the present invention relates to a compound selected from the group consisting of
N-{1-[2-(1,3-Dioxolan-2-yl)ethyl]piperidin-4-yl}-N-(4-fluorobenzyl)-N'-(4-isobutoxybenzyl)carbamide, hydrochloride;
N-{1-[2-(1,3-Dioxan-2-yl)ethyl]piperidin-4-yl}-N-(4-fluorobenzyl)-2-[4-(2-hydroxy-2-methylpropoxy)phenyl]acetamide, tartrate;
N-(4-Fluorobenzyl)-N-(piperidin-4-yl)-2-(4-isobutoxyphenyl)acetamide;
N-{1-[3-(3,5-Dimethylpiperidin-1-yl)propyl]piperidin-4-yl}-N-(4-fluorobenzyl)-2-(4-isobutoxyphenyl)acetamide, dihydrochloride;
1-[3-(4-{(4-Fluorobenzyl)-2-(4-isobutoxyphenyl)acetyl]amino}piperidin-1-yl)propyl]piperidine-4-carboxylic acid methyl ester, dihydrochloride;
N-(4-Fluorobenzyl)-2-(4-isobutoxyphenyl)-N-{1-[2-(1-methylpyrrolidin-2-yl)ethyl]piperidin-4-yl}acetamide, dioxalate;
N-{1-[3-(2,6-Dimethylmorpholin-4-yl)propyl]piperidin-4-yl}-N-(4-fluorobenzyl)-2-(4-isobutoxyphenyl)acetamide, dioxalate;
N-(4-Fluorobenzyl)-N-{1-[3-(3-hydroxypiperidin-1-yl)propyl]piperidin-4-yl}-2-(4-isobutoxyphenyl)acetamide, dioxalate;
N-(4-Fluorobenzyl)-2-(4-isobutoxyphenyl)-N-{1-[3-(2-methylpiperidin-1-yl)propyl]piperidin-4-yl}acetamide, dioxalate;
N-(4-Fluorobenzyl)-2-(4-isobutoxyphenyl)-N-[1-(3-pyrrolidin-1-yl-propyl)piperidin-4-yl]acetamide, dioxalate;
N-{1-[3-(2,5-Dimethylpyrrolidin-1-yl)propyl]piperidin-4-yl}-N-(4-fluorobenzyl)-2-(4-isobutoxyphenyl)acetamide, dioxalate;
N-(4-Fluorobenzyl)-N-{1-[3-(3-hydroxymethylpiperidin-1-yl)propyl]piperidin-4-yl}-2-(4-isobutoxyphenyl)acetamide, dioxalate;
N-(4-Fluorobenzyl)-2-(4-isobutoxyphenyl)-N-{1-[3-(4-(S)-isopropyl-2-oxo-oxazolidin-3-yl)propyl]piperidin-4-yl}acetamide, oxalate;
N-[2-(4-Fluorophenyl)ethyl]-2-(4-isobutoxyphenyl)-N-{1-[3-(4-(S)-isopropyl-2-oxo-oxazolidin-3-yl)propyl]piperidin-4-yl}acetamide, oxalate;
N-[2-(4-Fluorophenyl)ethyl]-N-{1-[3-(4-(S)-isopropyl-2-oxo-oxazolidin-3-yl)propyl]piperidin-4-yl}-2-(4-propoxyphenyl)acetamide, oxalate;
N-(4-Fluorobenzyl)-N-{1-[3-(4-(S)-isopropyl-2-oxo-oxazolidin-3-yl)propyl]piperidin-4-yl}-2-(4-propoxyphenyl)acetamide, oxalate;
N-{1-[2-(1,3-Dioxan-2-yl)ethyl]piperidin-4-yl}-N-(4-fluorobenzyl)-2-(4-isobutoxyphenyl)acetamide, oxalate;
N-{1-[2-(1,3-Dioxan-2-yl)ethyl]piperidin-4-yl}-N-[2-(4-fluorophenyl)ethyl]-2-(4-isobutoxyphenyl)acetamide, oxalate;
N-{1-[2-(1,3-Dioxan-2-yl)ethyl]piperidin-4-yl}-N-[2-(4-fluorophenyl)ethyl]-2-(4-propoxyphenyl)acetamide, oxalate;
N-{1-[2-(1,3-Dioxan-2-yl)ethyl]piperidin-4-yl}-N-(4-fluorobenzyl)-2-(4-propoxyphenyl)acetamide, tartrate;
N-{1-[2-(1,3-Dioxan-2-yl)ethyl]piperidin-4-yl}-N-(4-fluorobenzyl)-N'-(4-isobutoxybenzyl)carbamide, tartrate;
N-{1-[2-(1,3-Dioxan-2-yl)ethyl]piperidin-4-yl}-N-(4-fluorobenzyl)-2-(4-fluorophenyl)acetamide, tartrate;
N-{1-[2-(1,3-Dioxan-2-yl)ethyl]piperidin-4-yl}-N-(4-fluorobenzyl)-2-p-tolylacetamide, tartrate;
2-Benzofuran-5-yl-N-{1-[2-(1,3-dioxan-2-yl)ethyl]piperidin-4-yl}-N-(4-fluorobenzyl)acetamide, tartrate;
2-(2,3-Dihydrobenzofuran-5-yl)-N-{1-[2-(1,3-dioxan-2-yl)ethyl]piperidin-4-yl}-N-(4-fluorobenzyl)acetamide, tartrate;
N-{1-[2-(2,2-Dimethyl-1,3-dioxolan-4-yl)ethyl]piperidin-4-yl}-N-(4-fluorobenzyl)-2-(4-isobutoxyphenyl)acetamide, tartrate;
N-{1-[2-(1,3-Dioxan-4-yl)ethyl]piperidin-4-yl}-N-(4-fluorobenzyl)amine;
N-{1-[2-(1,3-Dioxan-4-yl)ethyl]piperidin-4-yl}-N-(4-fluorobenzyl)-2-(4-isobutoxyphenyl)acetamide, tartrate;
N-{1-[2-(1,3-Dioxan-4-yl)ethyl]piperidin-4-yl}-N-(4-fluorobenzyl)-2-(4-trifluoromethylphenyl)acetamide, tartrate;
2-(4-Cyanophenyl)-N-{1-[2-(1,3-dioxan-4-yl)ethyl]piperidin-4-yl}-N-(4-fluorobenzyl)acetamide, tartrate;
N-(4-Fluorobenzyl)-2-(4-isobutoxyphenyl)-N-{1-[2-(2-oxo-imidazolidin-1-yl)ethyl]piperidin-4-yl}acetamide, hydrochloride;
2-(4-Methoxyphenyl)-N-(4-methylbenzyl)-N-{1-[2-(2-oxo-imidazolidin-1-yl)ethyl]piperidin-4-yl}acetamide, hydrochloride;
N-(4-Fluorobenzyl)-2-(4-isopropoxyphenyl)-N-{1-[2-(2-oxo-imidazolidin-1-yl)ethyl]piperidin-4-yl}acetamide, hydrochloride;

N-(4-Fluorobenzyl)-2-(4-isopropoxyphenyl)-N-{1-[3-(3-methyl-2-oxo-2,3-dihydro-benzoimidazol-1-yl)propyl]piperidin-4-yl}acetamide; hydrochloride;

N-{1-[2-(2,4-Dioxo-1,4-dihydro-2H-quinazolin-3-yl)ethyl]piperidin-4-yl}-2-(4-methoxyphenyl)-N-(4-methylbenzyl)acetamide, hydrochloride;

2-(4-Methoxyphenyl)-N-(4-methylbenzyl)-N-{1-[3-(2-oxo-2,3-dihydrobenzoimidazol-1-yl)propyl]piperidin-4-yl}-acetamide, hydrochloride;

N-(4-Fluorobenzyl)-2-(4-isopropoxyphenyl)-N-{1-[4-(2-oxo-2,3-dihydrobenzoimidazol-1-yl)butyl]piperidin-4-yl}acetamide, hydrochloride;

N-{1-[2-(2,4-Dioxo-1,4-dihydro-2H-quinazolin-3-yl)ethyl]piperidin-4-yl}-N-(4-fluorobenzyl)-2-(4-isopropoxyphenyl)acetamide, hydrochloride;

4-(4-Fluorobenzylamino)-piperidine-1-carboxylic acid benzyl ester;

N-(1-Benzyloxycarbonylpiperidin-4-yl)-N-(4-fluorobenzyl)-N'-(4-isopropoxybenzyl)carbamide;

N-(4-Fluorobenzyl)-N'-(4-isopropoxybenzyl)-N-piperidin-4-yl-carbamide, oxalate;

N-{1-[2-(1,3-Dioxolan-2-yl)ethyl]piperidin-4-yl}-N-(4-fluorobenzyl)-N'-(4-isopropoxy-benzyl)carbamide, oxalate;

N-{1-[2-(1,3-Dioxolan-2-yl)ethyl]piperidin-4-yl]-2-(4-methoxyphenyl)-N-(4-methylbenzyl)acetamide, hydrochloride;

N-{1-[2-(1,3-Dioxolan-2-yl)ethyl]piperidin-4-yl}-N-(4-fluorobenzyl)-2-(4-isobutoxyphenyl)acetamide, hydrochloride;

N-{1-[2-(1,3-Dioxolan-2-yl)ethyl]piperidin-4-yl}-2-(4-isopropoxyphenyl)-N-(4-methylbenzyl)acetamide, hydrochloride;

N-{1-[2-(1,3-Dioxolan-2-yl)ethyl]piperidin-4-yl}-N-(4-fluorobenzyl)-2-(4-propoxyphenyl)acetamide, tartrate;

N-(4-Fluorobenzyl)-N'-(4-isopropoxybenzyl)-N-{1-[2-((S)-4-methyl-1,3-dioxolane-2-yl)ethyl]piperidin-4-yl}carbamide, oxalate;

N-(4-Fluorobenzyl)-N'-(4-isopropoxybenzyl)-N-[1-(3-morpholin-4-yl-propyl)piperidin-4-yl]carbamide, oxalate;

2-(4-Methoxyphenyl)-N-(4-methylbenzyl)-N-[1-(2-morpholin-4-ylethyl)piperidin-4-yl]acetamide, dihydrochloride;

2-(4-Methoxyphenyl)-N-(4-methylbenzyl)-N-[1-(3-morpholin-4-ylpropyl)piperidin-4-yl]acetamide, dihydrochloride;

N-(4-Fluorobenzyl)-2-(4-isobutoxyphenyl)-N-[1-(3-morpholin-4-ylpropyl)piperidin-4-yl]acetamide, dihydrochloride;

N-(4-Fluorobenzyl)-2-(4-isopropoxyphenyl)-N-[1-(3-morpholin-4-yl-propyl)piperidin-4-yl]acetamide, dihydrochloride;

N-(4-Fluorobenzyl)-N'-(4-isopropoxybenzyl)-N-[1-(3-piperidin-1-yl-propyl)piperidin-4-yl]carbamide, oxalate;

N-(4-Fluorobenzyl)-N'-(4-isopropoxybenzyl)-N-[1-(3-((S)-4-isopropyl-2-oxazolidinon-1-yl-propyl)piperidin-4-yl]carbamide, tartrate;

N-(4-Fluorobenzyl)-N'-(4-isopropoxybenzyl)-N-{1-[2-(2,5,5-trimethyl-1,3-dioxan-2-yl)ethyl]}piperidin-4-yl]carbamide, oxalate;

N-{1-[3-(1,3-Dioxolan-2-yl)propyl]piperidin-4-yl}-N-(4-fluorobenzyl)-N'-(4-isopropoxybenzyl)carbamide, oxalate;

N-[1-(2,2-Dimethyl-1,3-dioxan-5-yl)piperidin-4-yl]-N-(4-fluorobenzyl)-N'-(4-isopropoxybenzyl)carbamide, oxalate;

N-(4-Fluorobenzyl)-N'-(4-isopropoxybenzyl)-N-{[2-(1-methyl pyrrolidin-2-yl)ethyl]-piperidin-4-yl}carbamide, oxalate;

N-[1-(2,2-Dimethyl-1,3-dioxan-5-yl)piperidin-4-yl]-N-(4-fluorobenzyl)-2-(4-isobutoxyphenyl)acetamide, oxalate;

N-[1-(1,3-Dioxan-5-yl)-piperidin-4-yl]-N-(4-fluorobenzyl)-2-(4-isobutoxyphenyl)acetamide, tartrate;

N-[1-(2,2-Dimethyl-1,3-dioxan-5-yl)piperidin-4-yl]-N-(4-fluorobenzyl)-2-(4-fluorophenyl)acetamide, tartrate;

N-{1-[2-(1,3-Dioxan-4-yl)ethyl]piperidin-4-yl}-N-(4-fluorobenzyl)-2-(4-fluorophenyl)acetamide, tartrate:

N-{1-[2-(1,3-Dioxan-4-yl)ethyl]piperidin-4-yl}-N-(4-fluorobenzyl)-2-(4-trifluoromethoxyphenyl)acetamide, tartrate:

N-{1-[2-(1,3-Dioxan-4-yl)ethyl]piperidin-4-yl}-N-(4-fluorobenzyl)-2-(4-propoxyphenyl)acetamide, tartrate;

N-(4-Fluorobenzyl)-2-(4-isobutoxyphenyl)-N-[1-(tetrahydropyran-4-yl)piperidin-4-yl]acetamide, tartrate;

N-(4-Fluorobenzyl)-2-(4-isobutoxyphenyl)-N-[1-(tetrahydropyran-4-ylmethyl)piperidin-4-yl]acetamide, tartrate;

N-(4-Fluorobenzyl)-2-(4-isobutoxyphenyl)-N-{1-[2-(tetrahydropyran-4-yl)ethyl]piperidin-4-yl]acetamide, tartrate;

N-(4-Fluorobenzyl)-2-(4-fluorophenyl)-N-[1-(tetrahydropyran-4-yl)piperidin-4-yl]acetamide, tartrate;

N-[1-((S)-3,5-Dihydroxypentyl)piperidine-4-yl]-N-(4-fluorobenzyl)-2-(4-isobutoxyphenyl)acetamide, tartrate;

N-{1-[2-((4S)-1,3-Dioxane-4-yl)ethyl]piperidine-4-yl}-N-(4-fluorobenzyl)-2-(4-isobutoxyphenyl)acetamide, tartrate;

N-{1-[2-(1,3-Dioxan-2-yl)ethyl]piperidin-4-yl}-N-(4-fluorobenzyl)amine;

2-(4-Benzyloxyphenyl)-N-{1-[2-(1,3-dioxan-2-yl)ethyl]piperidin-4-yl}-N-(4-fluorobenzyl)acetamide, tartrate;

N-{1-[2-(1,3-Dioxan-2-yl)ethyl]piperidin-4-yl}-N-(4-fluorobenzyl)-2-(4-hydroxyphenyl)-acetamide, tartrate;

N-{1-[2-(1,3-Dioxan-2-yl)ethyl]piperidin-4-yl}-N-(4-fluorobenzyl)-2-(4-methoxyphenyl)-acetamide, tartrate;

N-{1-[2-(1,3-Dioxan-2-yl)ethyl]piperidin-4-yl}-N-(4-fluorobenzyl)-2-(4-isopropylphenyl)-acetamide, tartrate;

N-{1-[2-(1,3-Dioxan-2-yl)ethyl]piperidin-4-yl}-N-(4-fluorobenzyl)-2-(4-trifluoromethoxy-phenyl)acetamide, tartrate;

N-{1-[2-(1,3-Dioxan-2-yl)ethyl]piperidin-4-yl}-N-(4-fluorobenzyl)-2-(4-ethoxyphenyl)-acetamide, oxalate;

N-{1-[2-(1,3-Dioxan-2-yl)ethyl]piperidin-4-yl}-N-(4-fluorobenzyl)-2-(4-isopropoxyphenyl)-acetamide, oxalate;

N-{1-[2-(1,3-Dioxan-2-yl)ethyl]piperidin-4-yl}-N-(4-fluorobenzyl)-2-phenylacetamide, oxalate;

N-{1-[2-(1,3-Dioxan-2-yl)ethyl]piperidin-4-yl}-N-(4-fluorobenzyl)-2-[4-(2-fluoroethoxy)-phenyl]acetamide, oxalate;

N-{1-[2-(5,5-Dimethyl-1,3dioxan-2-yl)ethyl]piperidin-4-yl}-N-(4-fluorobenzyl)-2-(4-isobutoxyphenyl)acetamide, oxalate;

N-(4-Fluorobenzyl)-2-(4-isobutoxyphenyl)-N-{1-[2-((R)-4-methyl-1,3-dioxan-2-yl)ethyl]-piperidin-4-yl}acetamide, oxalate;

N-(4-Fluorobenzyl)-2-(4-isobutoxyphenyl)-N-{1-[2-((S)-4-methyl-1,3-dioxolan-2-yl)ethyl]-piperidin-4-yl}acetamide, oxalate;

N-{1-[2-(4,6-Dimethyl-1,3-dioxan-2-yl)ethyl]piperidin-4-yl}-N-(4-fluorobenzyl)-2-(4-isobutoxyphenyl)acetamide, oxalate;

N-(4-Fluorobenzyl)-N-{1-[2-((S)-4-methyl-1,3-dioxolan-2-yl)ethyl]piperidin-4-yl}-2-(4-trifluoromethoxyphenyl)acetamide, oxalate;

N-(4-Fluorobenzyl)-2-(4-isopropylphenyl)-N-{1-[2-((S)-4-methyl-1,3-dioxolan-2-yl)ethyl]-piperidin-4-yl}acetamide, oxalate;
N-(4-Fluorobenzyl)-N-{1-[2-((R)-4-methyl-1,3-dioxan-2-yl)ethyl]piperidin-4-yl}-2-(4-trifluoromethoxyphenyl)acetamide, oxalate;
N-(4-Fluorobenzyl)-2-(4-isobutoxyphenyl)-N-{1-[2-(2,5,5-trimethyl-1,3-dioxan-2-yl)ethyl]piperidin-4-yl}acetamide, oxalate;
N-(4-Fluorobenzyl)-2-(4-isobutoxyphenyl)-N-{1-[2-(2-methyl-1,3-dioxolan-2-yl)ethyl]-piperidin-4-yl}acetamide, oxalate;
N-(4-Fluorobenzyl)-2-(4-isobutoxyphenyl)-N-{1-[3-(1,3-dioxolan-2-yl)propyl]piperidin-4-yl}acetamide, tartrate;
N-(4-Fluorobenzyl)-2-(4-isobutoxyphenyl)-N-{1-(3-piperidin-1-yl-propyl)piperidin-4-yl}-acetamide, dihydrochloride;
N-(4-Fluorobenzyl)-2-(4-isobutoxyphenyl)-N-{1-[2-(tetrahydropyran-2-yloxy)ethyl]-piperidin-4-yl}acetamide, oxalate;
N-(4-Fluorobenzyl)-2-(4-isobutoxyphenyl)-N-{1-[3-(2-oxo-piperidin-1-yl)propyl]piperidin-4-yl}acetamide;
N-(4-Fluorobenzyl)-2-(4-isobutoxyphenyl)-N-{1-[3-(2-oxo-pyrrolidin-1-yl)propyl]piperidin-4-yl}acetamide, hydrochloride;
N-(4-Fluorobenzyl)-2-(4-isobutoxyphenyl)-N-{1-[3-((R)-4-isopropyl-2-oxo-oxazolidin-3-yl)propyl]piperidin-4-yl}acetamide, oxalate;
N-(4-Fluorobenzyl)-2-(4-isobutoxyphenyl)-N-{1-[3-(2-oxo-oxazolidin-3-yl)propyl]piperidin-4-yl}acetamide, oxalate;
N-(4-Fluorobenzyl)-2-(4-isobutoxyphenyl)-N-{1-[3-((S)-4-methyl-2-oxo-oxazolidin-3-yl)propyl]piperidin-4-yl}acetamide, tartrate;
N-(4-Fluorobenzyl)-2-(4-isobutoxyphenyl)-N-{1-[3-((S)-4-ethyl-2-oxo-oxazolidin-3-yl)-propyl]piperidin-4-yl}acetamide, oxalate;
N-(4-Fluorobenzyl)-2-(4-isobutoxyphenyl)-N-{1-[2-(1,3-oxothiolan-2-yl)ethyl]piperidin-4-yl}acetamide, L-tartrate;
2-(4-Bromophenyl)-N-{1-[2-(1,3-dioxan-2-yl)ethyl]piperidin-4-yl}-N-(4-fluorobenzyl)-acetamide, L-tartrate;
N-{1-[2-(1,3-Dioxan-2-yl)ethyl)piperidin-4-yl}-N-(4-fluorobenzyl)-2-(4-isobutylamino-phenyl)acetamide, L-tartrate;
N-{1-[2-(1,3-Dioxan-2-yl)ethyl)piperidin-4-yl}-N-(4-fluorobenzyl)-2-(4-propylamino-phenyl)acetamide, L-tartrate;
N-{1-[2-(1,3-Dioxan-2-yl)ethyl)piperidin-4-yl}-N-(4-fluorobenzyl)-2-(4-(1-nitropropyl)-phenyl)acetamide, L-tartrate;
N-{1-[2-(1,3-Dioxan-2-yl)ethyl)piperidin-4-yl}-N-(4-fluorobenzyl)-2-[4-(2-oxopyrrolidin-1-yl)phenyl)acetamide, L-tartrate;
N-{1-[2-(1,3-Dioxan-2-yl)ethyl)piperidin-4-yl}-N-(4-fluorobenzyl)-2-(4-isobutylsulfanyl-phenyl)acetamide, L-tartrate;
N-{1-[2-(1,3-Dioxan-2-yl)ethyl)piperidin-4-yl}-N-(4-fluorobenzyl)-2-(4-iodophenyl)-acetamide, L-tartrate;
2-(4-Acetophenyl)-N-{1-[2-(1,3-dioxan-2-yl)ethyl)piperidin-4-yl}-N-(4-fluorobenzyl)-acetamide, L-tartrate;
2-[4-(1-Hydroxyiminoethyl)phenyl]-N-{1-[2-(1,3-dioxan-2-yl)ethyl)piperidin-4-yl}-N-(4-fluorobenzyl)acetamide, L-tartrate;
N-{1-[2-(1,3-Dioxan-2-yl)ethyl)piperidin-4-yl}-N-(4-fluorobenzyl)-2-(4-morpholin-4-yl-phenyl)acetamide, L-tartrate;
N-{1-[2-(1,3-Dioxan-2-yl)ethyl)piperidin-4-yl}-N-(4-fluorobenzyl)-2-(4-pyrazol-1-yl-phenyl)acetamide, L-tartrate;
N-{1-[2-(1,3-Dioxan-2-yl)-1-methylethyl]piperidin-4-yl}-N-(4-fluorobenzyl)-2-(4-iso-butoxyphenyl)-acetamide, L-tartrate;
N-{1-[2-(1,3-Dioxan-4-yl)ethyl)piperidin-4-yl}-N-(4-fluorobenzyl)-2-(4-pyrazol-1-yl-phenyl)acetamide, L-tartrate;
N-[1-((R)-3,5-Dihydroxypentyl)piperidine-4-yl]-N-(4-fluorobenzyl)-2-(4-isobutoxyphenyl)acetamide, tartrate;
N-{1-[2-((4R)-1,3-Dioxane-4-yl)ethyl]piperidine-4-yl}-N-(4-fluorobenzyl)-2-(4-isobutoxyphenyl)acetamide, tartrate; and
N-{1-[2-(1,3-Dioxan-2-yl)ethyl)piperidin-4-yl}-N-(4-fluorobenzyl)-2-[4-(1,2,4-triazol-4-yl)phenyl]acetamide, L-tartrate.

As stated, the present inventors have found that compounds of Formula I are effective modulators of the 5-HT2A subtype of human serotonin receptors. The invention thus further relates to a method of inhibiting an activity of a monoamine receptor comprising contacting the monoamine receptor or a system containing the monoamine receptor with an effective amount of one or more of the compounds as defined herein. The monoamine receptor may be a serotonin receptor, typically of the 5-HT2A subclass.

The serotonin receptor may alternatively be in the central nervous system or in the peripheral nervous system. Typically, the serotonin receptor may be in blood cells or platelets. In certain embodiments, the serotonin receptor may be mutated or modified.

The activity of a monoamine receptor that is modulated may typically be signaling activity. Moreover, the activity may typically be constitutive. The activity associated with serotonin receptor may typically be activation.

In another aspect, the present invention relates to a method of inhibiting an activation of a monoamine receptor comprising contacting the monoamine receptor or a system containing the monoamine receptor with an effective amount of one or more of the compounds as defined herein. The activation, which may be inhibited by the method of the invention, may typically be an activation resulting from an agonistic agent. The agonistic agent may be exogenous or the agonistic agent may be endogenous. Moreover, the activation may be constitutive.

Another aspect of the present invention relates to the treatment of disease conditions associated with dysfunction of a monoamine receptor and to the use of a compound of Formula I for the preparation of a medicament for the treatment of a disease condition associated with a monoamine receptor. The disease condition may be associated with activation of a monoamine receptor, such as associated with increased activity of monoamine receptor.

In yet another aspect, the present invention relates to a method of treating schizophrenia comprising administering to a subject in need of such treatment a therapeutically effective amount of a compound of Formula I, as defined herein. Alternatively stated, the invention relates, in part, to the use of a compound of Formula I for the preparation of a medicament for the treatment of schizophrenia. A further aspect relates to a method of treating migraine comprising administering to a subject in need of such treatment a therapeutically effective amount of a compound of Formula I. Alternatively stated, the invention relates, in part, to the use of a compound of Formula I for the preparation of a medicament for the treatment of migraine. A further aspect of the invention relates to a method of treating psychosis comprising administering to a subject in need of such treatment a therapeutically effective amount of a compound of Formula I. Alternatively stated, the invention relates, in part, to the use of a compound of Formula I for the preparation of a medicament for the treatment of psychosis. A still further aspect of the invention relates to a method of treating psychotic symptoms, such as hallucinations, consequent of administration of dopamine agonists, such as L-dopa, to individuals in need of treatment, such as people suffering from Parkinson's comprising administering a compound of Formula I. Alternatively stated, the invention relates, at least in part, to the use of a compound of Formula I for the preparation of a medicament for the treatment of psychotic symptoms, such as hallucinations, consequent of administration of dopamine agonists, such as L-dopa, to individuals in need of treatment, such as people suffering from Parkinson's disease.

Another aspect of the present invention relates to a method of treating a disease condition associated with a monoamine receptor comprising administering to a subject in need of such treatment a therapeutically effective amount of one or more of the compound of Formula I, as defined herein. The disease condition may be selected from the group consisting of schizophrenia, schizoaffective disorders; psychosis and related behavioral abnormalities observed with neurodegenerative disorders including Parkinson's, Alzheimer's disease, Lewy Body Dementia, Frontotemporal Dementia, Huntington's disease, and Spinocerebellar Atrophy; drug induced psychosis including side effects observed with selective serotonin reuptake inhibitor (SSRI) treatment of chronic neurodegenerative disorders such as Alzheimer's, Parkinson's and Huntington's disease; Reynaud's Phenomena; migraine; hypertension; thrombosis; vasospasm; ischemia; depression; anxiety; "motor tics"; Tourette's syndrome; dyskinesias, on/off phenomena, tremor, rigidity, bradykinesia, psychomotor slowing, addiction, including alcohol addiction, opioid addiction, and nicotine addiction; sleep disorders; appetite disorders; decreases in libido and ejaculatory problems. Thus, the invention thus relates to the use of a compound of Formula I, as defined herein, for the preparation of a medicament for the for the treatment of diseases and conditions selected from the group consisting of schizophrenia, schizoaffective disorders; psychosis and related behavioural abnormalities observed with neurodegenerative disorders including Parkinson's, Alzheimer's disease, Lewy Body Dementia, Frontotemporal Dementia, Huntington's disease, and Spinocerebellar Atrophy; drug induced psychosis including side effects observed with SSRI treatment of chronic neurodegenerative disorders such as Alzheimer's, Parkinson's and Huntington's disease; Reynaud's Phenomena; migraine; hypertension; thrombosis; vasospasm; ischemia; depression; anxiety; "motor tics"; Tourette's syndrome; dyskinesias, on/off phenomena, tremor, rigidity, bradykinesia, psychomotor slowing, addiction, including alcohol addiction, opioid addiction, and nicotine addiction; sleep disorders; appetite disorders; decreases in libido and ejaculatory problems.

Another aspect of the present invention relates to the treatment of drug induced psychosis and the treatment of side effects observed with SSRI treatment behavioural aspects of chronic neurodegenerative disorders, typically to the treatment of psychotic symptoms, such as hallucinations, consequent of administration of dopamine agonists, such as L-dopa, to individuals in need of treatment, such as people suffering from Parkinson's.

Similarly, aspects of the invention relate to a method for the treatment of diseases and conditions as described herein comprising administering an adjunctive or therapeutic amount of one or more of the compound of Formula I. The invention thus relates to the use of a compound of Formula I for the preparation of a medicament for the treatment of diseases and conditions as described herein wherein the compound of Formula I is the sole active agent in the medicament or is an adjunctive wherein the medicament further comprises an agent known to the person skilled in the art for the treatment of said diseases and conditions.

Other aspects of the invention relate to pharmaceutical compositions comprising an effective amount of a compound of general Formula I. Compounds of the present invention may be administered in any of the foregoing compositions and according to dosage regimens established in the art whenever specific pharmacological modification of the activity of monoamine receptors is required.

Aspects of the present invention also provide pharmaceutical compositions comprising one or more compounds of the invention together with a pharmaceutically acceptable diluent or excipient. Preferably such compositions are in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g., intravenous, intramuscular or subcutaneous), intranasal, sublingual or rectal administration, or for administration by inhalation or insufflation, and may be formulated in an appropriate manner and in accordance with accepted practices such as those disclosed in *Remington's Pharmaceutical Sciences*, (Gennaro, ed., Mack Publishing Co., Easton Pa., 1990, herein incorporated by reference). Alternatively, the compositions may be in sustained-release form suitable for once-weekly or once-monthly administration; for example, an insoluble salt of the active compound, such as the decanoate salt, may be adapted to provide a depot preparation for intramuscular injection. The present invention also contemplates providing suitable topical formulations for administration to, e.g., eye or skin or mucosa.

A further aspect of the invention relates to a method for identifying a genetic polymorphism predisposing a subject to being responsive to one or more of the compounds of Formula I, as defined herein, comprising:

administering to a subject a therapeutically effective amount of the compound;

measuring the response of said subject to said compound, thereby identifying a responsive subject having an ameliorated disease condition associated with a monoamine receptor; and identifying a genetic polymorphism in the responsive subject, wherein the genetic polymorphism predisposes a subject to being responsive to the compound. The ameliorated disease condition is typically associated with the 5-HT class or 5-HT2A subclass of monoaminergic receptors.

A further aspect of the invention relates to a method for identifying a subject suitable for treatment with one or more of the compounds of Formula I, comprising detecting the presence of a polymorphism in a subject wherein the polymorphism predisposes the subject to being responsive to the compound, and wherein the presence of the polymorphism indicates that the subject is suitable for treatment with one or more of the compounds of Formula I.

Methods of Preparation

The compounds in accordance with the present invention may be synthesized by methods described below, or by modification of these methods. Ways of modifying the methodology include, among others, temperature, solvent, reagents etc, and will be obvious to those skilled in the art.

For instance, compounds of the formula C may be synthesized from the corresponding ketone A by reductive amination utilizing any primary amine. The reaction is conveniently carried out by stirring the reactants in an inert solvent such as methanol or ethanol containing acetic acid. As reducing agent $NaBH_4$, $NaCNBH_3$, $BH_3$.pyridine or any related reagent may be used including solid-supported reagents. The reaction is typically carried out at room temperature. The ketone A, as exemplified by the piperidone, may be chosen from a list of compounds corresponding to the Z-group listed in formula (I). The ketones can either be obtained commercially or synthesized by methodology disclosed in Lowe et al. *J. Med. Chem.* 37: 2831-40 (1994); Carroll et al. *J. Med. Chem.* 35:2184-91 (1992); or Rubiralta et al. *Piperidine-Structure, Perparation, Reactivity and Synthetic Applications of Piperidine and its Derivatives.* (*Studies in Organic Chemistry* 43, Elsevier, Amsterdam, 1991). The protecting group P includes groups such as those described in T. W. Greene and P. G. M. Wuts, *Protective Groups in Organic Chemistry*, 3. Ed. John Wiley & Sons, 1999, and they should be chosen in such a way, that they are stable to the reaction conditions applied and readily removed at a convenient stage using methodology known from the art. Typical protecting groups are N-Boc, N-Cbz, N-Bn.

Alternatively, the amine C can be synthesized from the primary amine B by reductive amination with any aldehyde. The reaction is conveniently carried out by stirring the reactants in an inert solvent such as methanol or ethanol containing acetic acid. As reducing agent $NaBH_4$, $NaCNBH_3$, $BH_3$.pyridine or any related reagent may be used including solid-supported reagents. The reaction is typically carried out at room temperature. The primary amine B, as exemplified by the 4-aminopiperidine, may be chosen from a list of compounds corresponding to the Z-groups listed in formula (I). The amines can either be obtained commercially or synthesized from the corresponding ketones. The protecting group P may be chosen as stated above.

Alternatively, the amine C can be synthesized from the primary amine B by alkylation with any alkylating agent (R-$L_1$). The leaving group $L_1$ is suitably a halogen atom, e.g., bromine or iodine, or a sulfonate, e.g. tosylate or mesylate, or another leaving group favoring the reaction. The reaction is conveniently carried out by stirring the reagents under basic conditions in an inert solvent, e.g., diisopropylethylamine in acetonitrile, or $K_2CO_3$ in N,N-dimethylformamide. The reaction is typically carried out at temperatures between room temperature and 80° C. The primary amine B, as exemplified by the 4-aminopiperidine, may be chosen from a list of compounds corresponding to the Z-groups listed in formula (I). The amines can either be obtained commercially or synthesized from the corresponding ketones. The protecting group P may be chosen as stated above.

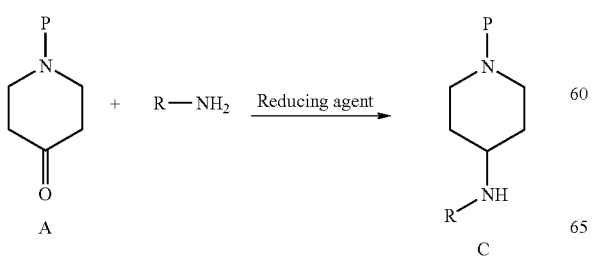

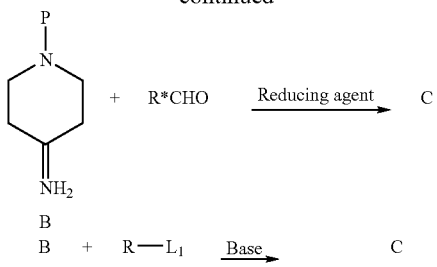

Wherein R and R* are defined in agreement with Formula I, and P represents a suitable protecting group, and $L_1$ represents a suitable leaving group.

The secondary amine C may be acylated using any isocyanate or isothiocyanate ($Q_1$-N=C=W) to give the corresponding ureas or thioureas D. The reaction is typically carried out by stirring the reactants, using an excess of isocyanate or isothiocyanate in an inert solvent, e.g., dichloromethane at a temperature between 0° C. and room temperature and under dry conditions. The amine C may also be acylated using any carboxylic acid halide ($Q_2$COX), e.g., chloride, or carboxylic anhydride (($Q_2$C=O)$_2$O) to give amides of the general structure E. The reaction is typically carried out using an excess of the acylating agent and a suitable base, e.g., triethylamine or diisopropylethylamine in an inert solvent, e.g., dichloromethane, at a temperature between 0° C. and room temperature and under dry conditions. As an alternative to the carboxylic acid halides and carboxylic acid anhydrides, the amine C may be acylated using a carboxylic acid ($Q_2$COOH) and a suitable coupling reagent e.g. PyBroP, DCC or EDCI. The reaction is typically carried out using an excess of the acylating agent and the coupling reagent in an inert solvent, e.g., dichloromethane at a temperature between 0° C. and room temperature and under dry conditions. The compounds of the general structure (E) may be converted into the corresponding thioamides using methodology disclosed in Varma et al., *Org. Lett.* 1: 697-700 (1999); Cherkasov et al. *Tetrahedron* 41:2567 (1985); or Scheibye et al, *Bull. Soc. Chim. Belg.* 87:229 (1978).

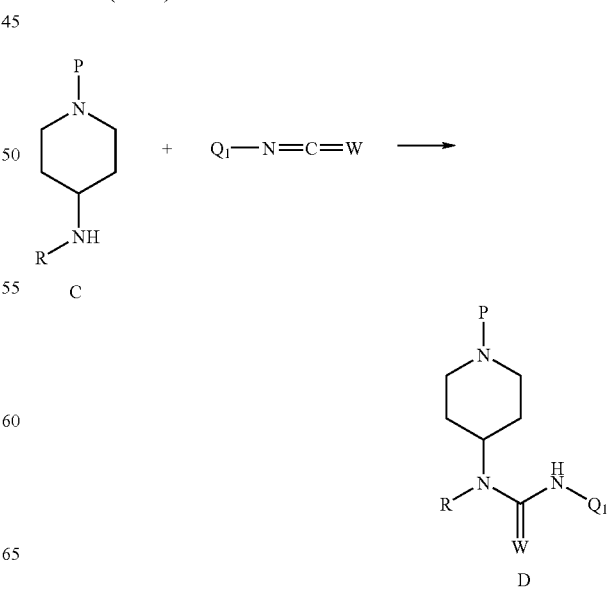

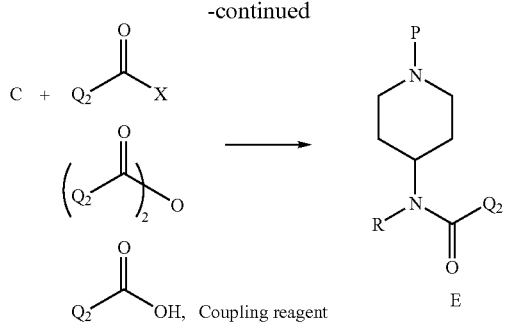

Wherein R, $Q_1$, $Q_2$, and W are defined in agreement with formula (I), P represents a suitable protecting group, and X represents a halide.

The substituent T on the ring nitrogen in compounds F or G can be introduced by a two step procedure. First, the protecting group on the urea D or the amide E is removed using well-known methods. For example, the N-Boc group is removed by treating the protected compound with 4 M HCl in dioxane or trifluoroacetic acid in dichloromethane. Second, the secondary amines obtained from D and E can be alkylated by reductive amination using any aldehyde (T*-CHO) or ketone (T=O). The reaction is conveniently carried out by stirring the reactants in an inert solvent such as methanol or ethanol. As a reducing agent, solid-supported borohydride, $NaBH_4$, $NaCNBH_3$, $BH_3$.pyridine, $H_2$/Pd—C or any related reagent may be used, including solid-supported reagents. The reaction is typically carried out at room temperature.

Alternatively, the compounds F and G can be synthesized from the secondary amine obtained from D or E as described above by alkylation with any alkylating agent (T-$L_1$). The leaving group $L_1$ is suitably a halogen atom, e.g., bromine or iodine, or a sulfonate, e.g., tosylate or mesylate, or another leaving group favoring the reaction. The reaction is conveniently carried out by stirring the reagents under basic conditions in an inert solvent, for example diisopropylethylamine in acetonitrile, or $K_2CO_3$ in N,N-dimethylformamide. The reaction is typically carried out at temperatures between room temperature and 80° C.

Alternatively, the T-group can be introduced in the first step of the synthetic sequence leading to the compounds in accordance with the present invention by N-alkylation of compound H with any alkylating agent (T-$L_1$). The leaving group $L_1$ is suitably a halogen atom, e.g., bromine or iodine, or a sulfonate, e.g., tosylate or mesylate, or another leaving group favoring the reaction. The reaction is conveniently carried out by stirring the reagent under basic conditions in an inert solvent, e.g., diisopropylethylamine in acetonitrile, or $K_2CO_3$ in N,N-dimethylformamide. The reaction is typically carried out at temperatures between room temperature and 80° C. Alternatively the T-group can be introduced in the first step by reductive amination using any aldehyde (T*-CHO) or ketone (T=O) and a suitably protected compound H', exemplified by 4-piperidone ethylene ketal. The reaction is conveniently carried out by stirring the reactants in an inert solvent such as methanol or ethanol. As a reducing agent, solid-supported borohydride, $NaBH_4$, $NaCNBH_3$, $BH_3$.pyridine, $H_2$/Pd—C or any related reagent may be used, including solid-supported reagents. The reaction is typically carried out at room temperature, but less reactive carbonyl compounds may require higher temperatures and/or the preformation of the corresponding imine under water removal before addition of the reducing agent. Removal of the protecting group gives the desired compound J. The secondary amine H and H', as exemplified by 4-piperidone and its protected derivative, may be chosen from a list of compounds corresponding to the Z-groups listed in formula (I). The amines can either be obtained commercially or synthesized from methodology disclosed in Lowe et al., *J. Med. Chem.* 37:2831-40 (1994); and Carroll et al., *J. Med. Chem.* 35:2184-91 (1992).

Alternatively, compounds of the general structure J may be synthesized starting from K using the method disclosed in: Kuehne et al., *J. Org. Chem.* 56:2701 (1991); and Kuehne et al., *J. Org. Chem.* (1991), 56:513.

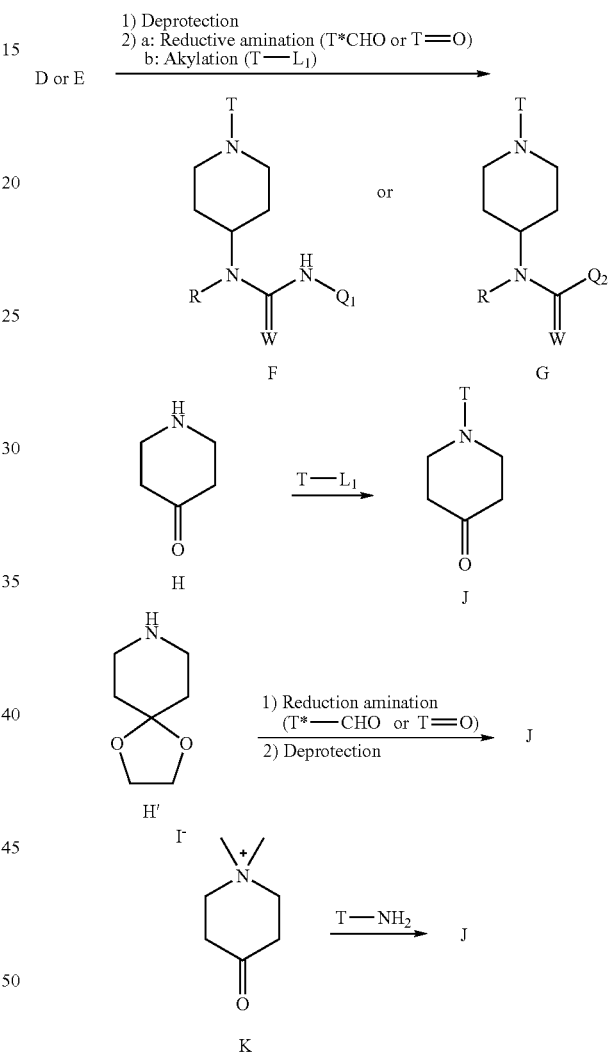

Wherein R, $Q_1$, $Q_2$, W, and T are defined in agreement with formula (I), and $L_1$ is a suitable leaving group.

Heterocyclylalkyl alkylating agents such as T-$L_1$ may be commercially available or are typically obtained by alkylation of a heterocycle with a bifunctional alkyl-linker, as shown below. The leaving groups $L_1$ and $L_2$ are suitably a halogen atom, e.g., chlorine, bromine or iodine, or a sulfonate, e.g., tosylate or mesylate, or another leaving group favoring the reaction. The reaction is conveniently carried out by stirring the reagent under basic conditions in an inert solvent, e.g., diisopropylethylamine in acetonitrile, or $K_2CO_3$ in N,N-dimethylformamide. The reaction is typically carried out at temperatures between room temperature and 80° C.

The alkylating agent hence obtained can be either reacted in situ in the next step with the secondare amine (i.e. deprotected D/E, or H) or isolated from the reaction mixture before its further use. Heterocyclylalkyl alcohols such as T*-CH$_2$OH or T-OH may also be converted into suitable alkylating agents T-L$_1$ by transforming the hydroxyl into a leaving group, e.g. by tosylation, mesylation or halogenation. Alternatively, T*-CH$_2$OH or T-OH may be oxidized to the corresponding aldehydes or ketones T*-CHO or T=O with, for example, pyridinium chlorochromate, CrO$_3$—H$_2$SO$_4$, or via the Swern or Dess-Martin procedures, to be used in a reductive amination step with the secondary amines as described above.

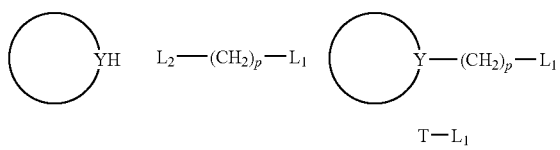

Wherein Y, p and T are defined in agreement with formula (I), and L$_1$ and L$_2$ are suitable leaving groups.

The building blocks incorporating the aromatic groups Ar$_1$ and Ar$_2$ may either be obtained commercially or synthesized from methodology disclosed in the literature. The introduction of substituents on Ar$_1$ and Ar$_2$ may be performed from a suitable precursor at any appropriate stage of the preparation of the compounds.

For instance, compounds containing an alkoxy substituents may be typically prepared by Williamson ether synthesis from the corresponding hydroxyaryl derivatives.

Structures bearing an amine substituent on Ar$_1$ or Ar$_2$ may be obtained from a suitable halo- or pseudohalo precursor (e.g. Br, I—, Cl—, triflate-, nonaflate-, tosylate-substituted aryl derivatives) by metall-catalyzed amination chemistries, such as Pd— or Ni— (Hartwig, *Angew. Chem. Int. Ed.*, 1998, 37, 2046-2067; Yang & Buchwald, *J. Organometallic Chem.*, 1999, 576, 125-146; Hartwig in *Modern Amination Methods;* Ricci, Ed.; Wiley-VCH: Weinheim, Germany, 2000) or Cu-catalyzed (Buchwald et al, *Org. Lett.*, 2002, 4, 581-584; Kwong & Buchwald, *Org. Lett.*, 2003, 5, 793-796). Alternatively, these compounds can be obtained from aniline-based precursors either by alkylation (Hickinbottom, *J. Chem. Soc.* 1930, 992), or by reductive amination (Emerson & Walters, *J. Am. Chem. Soc.*, 1938, 60, 2023; Milovic et al, *Synthesis*, 1991, 11, 1043-1045), or by dehydrative alkylation (Rice & Kohn, *J. Am. Chem. Soc.*, 1955, 77, 4052; Brown & Reid, *J. Am. Chem. Soc.*, 1924, 46, 1838). Additionally, compounds of this type may also be synthesized from corresponding boronic acids by Cu-catalyzed coupling (Antilla & Buchwald, *Org. Lett.*, 2001, 3, 2077-2079).

The structures bearing an amide substituent on Ar$_1$ or Ar$_2$ may be obtained from a suitable halo- or pseudohalo precursor either by Pd catalyzed (Yin & Buchwald, *J. Am. Chem. Soc.*, 2002, 124, 6043-6048) or by Cu catalyzed (Buchwald et al, *J. Am. Chem. Soc.*, 2002, 124, 7421-7428) amidation chemistries. Alternatively, these compounds may also be obtained from the corresponding aniline precursors either by acylation (Wolf, *Liebigs Ann. Chem.*, 1952, 576, 35; Yasukara et al, *J. Chem. Soc. Perkin Trans.* 1, 2000, 17, 2901-2902; Nigam & Weedon, *J. Chem. Soc.*, 1957, 2000) or by formylation (Hirst & Cohen, *J. Chem. Soc.*, 1895, 67, 830; Olah & Kuhn, *Chem. Ber.* 1956, 89, 2211; Guthrie et al, *Can. J. Chem.*, 1993, 71, 2109-2122).

Compounds that carry an alkylsulfanyl substituent on Ar$_1$ or Ar$_2$ be obtained from a suitable halo- or pseudohalo precursor by Pd catalyzed (Li, *J. Org. Chem.*, 2002, 67, 3643-3650), or Cu catalyzed (Kwong & Buchwald, *Org. Lett.*, 2002, 4, 3517-3520) thioetherification chemistry. Alternatively, these compounds may be prepared by alkylation of corresponding benzenethiol precursors (Vogel, *J. Chem. Soc.*, 1948, 1809; Landini & Rocca, *Synthesis*, 1974, 565-566; Bun-Hoi et al, *J. Org. Chem.*, 1951, 16, 988). Alternatively, alkylarylsulfanyls may be obtained by irradiation of benzenethiols and alkenes (Screttas & Micha-Screttas, *J. Org. Chem.*, 1978, 43, 1064-1071).

Compounds of the invention bearing an acyl group on Ar$_1$ or Ar$_2$ may be prepared from corresponding aryl iodides by Pd catalyzed (Cacchi et al, *Org. Lett*, 2003, 5, 289-293) acylation chemistry. Alternatively, they may be obtained from the corresponding benzenes by Friedel-Crafts chemistry (Read, *J. Am. Chem. Soc.*, 1922, 44, 1746-1755), or by addition of aryl-Grignard reagents to nitriles (Whitmore et al, *J. Am. Chem. Soc.*, 1947, 69, 235-237) or to acyl chlorides (Whitmore & Lester, *J. Am. Chem. Soc.*, 1942, 64, 1247), or by either Pd-catalyzed (Gooβen & Ghosh, *Angew. Chem. Int. Ed. Engl.*, 2001, 40, 3458-3460) or Rh-catalyzed acylation of arylboronic acids.

Compounds of the invention that bear an N-containing aromatic heterocycle on Ar$_1$ or Ar$_2$ can be obtained either by metall-catalyzed cross-couplings (Buchwald et al, *Org. Lett.*, 2002, 2, 1403-1406; Buchwald et al, *J. Am. Chem. Soc.*, 2001, 123, 7727-7729; Buchwald et al, *J. Am. Chem. Soc.*, 2002, 124, 11684-11688). Alternatively, they may be accessed from suitable precursors such as aryl hydrazines, aryl amines or aryl nitrites according to literature procedures (e.g. Alvisi, *Gazz. Chem. Ital.*, 1892, 22, 159; Finar, Godfrey, *J. Chem. Soc.*, 1954, 2293; Muri et al, *Synth. Commun.*, 1998, 28, 1299-1321; Artico et al, *Europ. J. Med. Chem. Chim. Ther.*, 1992, 27, 219-228; Biagi et al., *Farmaco Ed. Sci.* 1988, 43, 597-612; Stefancich et al, *Farmaco Ed. Sci.*, 1984, 39, 752-764).

In general, during any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991. The protecting groups may be removed at a convenient subsequent stage using methods known from the art.

EXAMPLES

The examples below are non-limiting and are only illustrative of some of the embodiments of the present invention.

Chemical Synthesis

General procedures. $^1$H NMR spectra were recorded at 400 MHz on a Varian Mercury-VX400 MHz spectrometer and chemical shifts are given in δ-values [ppm] referenced to the residual solvent peak chloroform (CDCl$_3$) at 7.26 and methanol (CD$_3$OD) at 3.31 ppm. Coupling constants, J, are reported in Hertz. Unless otherwise stated, the NMR spectra of the compounds are described for their free amine form. Due to the presence of rotamers, two sets of signals are generally observed and rotamer ratios are reported. Where the corresponding signals for each of the two rotamers could unmistakably be identified, they are reported together [e.g. 4.66-4.58 and 3.76-3.68 (2 m, 1H)]. Acidic ion-exchange solid phase extraction (SPE) cartridges were MEGA BE-SCX from Varian.

Materials and solvents were of the highest grade available from commercial sources and were used without further purification.

HPLC/LCMS Method. The analysis was performed on a combined prep/analytical Waters/Micromass system consisting of a ZMD single quadropole mass spectrometer equipped with electrospray ionization interface. The HPLC system consisted of a Waters 600 gradient pump with on-line degassing, a 2700 sample manager and a 996 PDA detector. Separation was performed on an X-Terra MS C18, 5 µm 4.6×50 mm column. Buffer A: 10 mM ammoniumacetate in water, buffer B: 10 mM ammoniuacetate in acetonitrile/water 95/5. A gradient was run from 30% B to 100% B in 7 min, hold at 100% B for 1 min and re-equilibrated for 5.5 min. The system was operated at 1 ml/min.

Preparation of hydrochloride salts. Typically, the tertiary amines were dissolved in dichloromethane, treated with an excess of 1M HCl in diethylether and precipitated from n-heptane. The solvents were removed in vacuo and after drying, the hydrochloride salts were obtained as colourless solids.

Preparation of oxalate or tartrate salts. Typically, the tertiary amines were dissolved in methanol, treated with 1 eq. of the appropriate acid, the solvent removed and the salt redissolved in dichloromethane and precipitated from n-heptane. The solvents were removed in vacuo affording the salts as colourless solids.

Preparation of Phenylacetyl Chloride Derivatives

The phenylacetic acid derivative (15 mmol) was dissolved in dichloromethane (100 mL), and oxalylchloride (45 mmol) was added slowly. The reaction mixture was stirred for 4 hours and then evaporated to dryness. The product was obtained as a colourless oil and used immediately after preparation in the acylation step.

4-Isobutoxyphenylacetic acid (128NLS28)

Methyl 4-hydroxyphenyl acetate (14.6 g, 0.0885 mol) was dissolved in DMF (200 mL), potassium carbonate (31.0 g, 0.224 mmol) added and the mixture was stirred for 1 h at rt. 1-Bromo-2-methylpropane (19.2 mL, 0.177 mol) was added and the mixture was heated at 80° C. for 3 days under vigorous stirring. The mixture was cooled to rt, filtered, the solvent removed and the residue partitioned between 1.5M NaOH and ethyl acetate. The organic layer was evaporated, the residue dissolved in methanol (100 mL) and water (100 mL), KOH (10 g, 0.178 mol) added and the mixture stirred overnight at rt. The methanol was removed by evaporation, the mixture extracted with dichloromethane. The organic layer was discarded, the aqueous layer acidified with 4M HCl to pH2-3 and extracted twice with dichloromethane. The combined organic layers were dried over $Na_2SO_4$, filtered and evaporated to give the title compound (16.9 g, 92%) as a colourless solid.

4-Propoxyphenylacetic acid (98AF77-66)

Prepared as described for 128NLS28 using propylbromide as the alkylating agent.

4-Isopropoxyphenylacetic acid (130AF24-163)

Prepared as described for 128NLS28 using isopropylbromide as the alkylating agent.

N-{1-[2-(1,3-Dioxolan-2-yl)ethyl]piperidin-4-yl}-N-(4-fluorobenzyl)-N'-(4-isobutoxybenzyl)carbamide, hydrochloride (80MBT86-2C)

4-Piperidone hydrochloride monohydrate (4.0 g, 26.0 mmol) was dissolved in dichloromethane (130 mL). After addition of triethylamine (8.66 g, 85.8 mmol), the mixture was stirred for 10 min and then cooled to 0° C. Trifluoroacetic anhydride (12.0 g, 57.2 mmol) was added dropwise under stirring. After 2 h at room temperature, the reaction was stopped by addition of water (100 mL), and the aqueous phase was extracted with dichloromethane (2×100 mL). The combined organic phases were dried over $Na_2SO_4$, filtered and concentrated to give 1-(trifluoroacetyl)-4-piperidone (5.07 g, 100%).

4-Fluorobenzylamine (3.14 g, 25.9 mmol) was dissolved in methanol (150 mL). 1-(trifluoroacetyl)-4-piperidone (5.07 g, 25.9 mmol) was added, and the pH was adjusted to ~5 with acetic acid. The reaction mixture was stirred for 5 min and $NaBH_3CN$ (2.46 g, 38.9 mmol) was added slowly under stirring. After 20 h at room temperature the reaction was concentrated. 2 M NaOH (100 mL) was added and the aqueous phase was extracted with dichloromethane (2×100 mL). The combined organic phases were dried over $Na_2SO_4$, filtered and concentrated to give N-(4-fluorobenzyl)-1-(trifluoroacetyl)piperidin-4-amine (50ELH85, 2.91 g, 37%).

4-isobutoxyphenylacetic acid (7.6 g, 36.5 mmol) was dissolved in THF (50 mL). Proton Sponge™ (8.2 g, 38 mmol) was added, and the mixture was stirred for 15 min. Diphenylphosphoryl azide (10.6 g, 38 mmol) was added dropwise and the mixture was heated to reflux for 4 h. The mixture was cooled to room temperature and placed in the freezer at −18° C. for 20 h. The resulting white precipitate was vigorously stirred with diethyl ether (250 mL) for 15 min and filtered. The filtrate was evaporated to give crude 4-isobutoxybenzyl isocyanate (1.97 g, 9.6 mmol), which was dissolved in dichloromethane (50 mL) and added to a solution of 50ELH85 (2.91 g, 9.6 mmol) in dichloromethane (50 mL). The reaction mixture was stirred for 20 h and concentrated. The crude product was purified by flash chromatography (0-5% methanol in dichloromethane) to give N-(4-fluorobenzyl)-N-[1-(trifluoroacetyl)piperidin-4-yl]-N'-(4-isobutyloxybenzyl)carbamide (76ELH17, 3.90 g, 91%).

The compound 76ELH17 (3.90 g, 8.7 mmol) was dissolved in methanol (12 ml) and added to a 2 M solution of potassium carbonate in methanol (100 mL) under stirring. After 4 h the methanol was evaporated, and the aqueous phase was extracted with dichloromethane (2×100 mL). The combined organic phases were dried over $Na_2SO_4$, filtered and concentrated to give a semi-pure solid (2.95 g), which was purified by flash chromatography (10% methanol in dichloromethane with 1% triethylamine) to give N-(4-fluorobenzyl)-N-(piperidin-4-yl)-N'-(4-isobutyloxybenzyl)carbamide (76ELH18, 1.40 g, 39%) as a colourless solid. LCMS m/z 414 $[M+H]^+$. $^1$H-NMR ($CDCl_3$): δ 7.21-6.75 (m, 8H), 4.47-4.42 (m, 1H), 4.39 (t, J=5 Hz, 1H), 4.35 (s, 2H), 4.27 (d, J=5 Hz, 2H), 3.68 (d, J=6 Hz, 2H), 3.13-3.06 (m, 2H), 2.74-2.66 (m, 2H), 2.11-1.99 (m, 1H), 1.78-1.71 (m, 3H), 1.58-1.46 (m, 2H), 1.00 (d, J=6 Hz, 6H).

The compound 76ELH18 (200 mg, 0.484 mmol) was dissolved in acetonitrile (20 mL). Potassium carbonate (74 mg, 0.553 mmol) and sodium iodide (80 mg, 0.553 mmol) was added followed by 2-(2-bromoethyl)-1,3-dioxolane (100 mg, 0.553 mmol). The reaction mixture was heated to reflux for 20 h. The mixture was concentrated, water (50 mL) was added, and the aqueous phase was extracted with dichloromethane (2×50 mL). The combined organic phases were dried over Na$_2$SO$_4$, filtered and evaporated. The resulting oil was purified twice by flash chromatography (5% methanol in dichloromethane) to give a colourless oil (50 mg, 20%). R$_f$=0.70 (MeOH/CH$_2$Cl$_2$ 1:9). LCMS m/z 514 [M+H]$^+$. $^1$H-NMR (CDCl$_3$): δ 7.21-6.75 (m, 8H), 4.94 (t, J=4.5 Hz, 1H), 4.73-4.62 (m, 1H), 4.58 (t, J=5.5 Hz, 1H), 4.41 (s, 2H), 4.26 (d, J=5.5 Hz, 2H), 4.00-3.80 (m, 4H), 3.68 (d, J=6.0 Hz, 2H), 3.43-3.35 (m, 2H), 2.94-2.87 (m, 2H), 2.68-2.57 (m, 2H), 2.45-2.32 (m, 2H), 2.20-2.13 (m, 2H), 2.10-2.00 (m, 1H), 1.88-1.81 (m, 2H), 1.00 (d, J=6.0 Hz, 6H). HPLC t$_R$=8.1 min.

The collected compound was converted into its hydrochloride salt, which was obtained as a colourless solid (80MBT86-2C).

N-{1-[2-(1,3-Dioxan-2-yl)ethyl]piperidin-4-yl}-N-(4-fluorobenzyl)-2-[4-(2-hydroxy-2-methylpropoxy)phenyl]acetamide, tartrate (106MBT54-D)

Methyl (4-hydroxyphenyl)acetate (500 mg, 3.0 mmol) was dissolved in DMF (3 mL). K$_2$CO$_3$ (829 mg, 6.0 mmol) was added followed by isobutylene oxide (800 μL, 9.0 mmol). The mixture was heated to 150° C. by microwave irradiation for 30 min and concentrated. The residue was dissolved in a 1:1 mixture of methanol and water (20 mL). NaOH (1 g) was added and the mixture was stirred for 30 min. Methanol was removed by rotary evaporation. The aqueous phase was acidified by 4 M HCl and extracted with dichloromethane (2×50 mL). The combined organic phases were extracted with 2 M NaOH (2×50 mL). The combined aqueous phases were subsequently acidified by 4 M HCl and extracted with dichloromethane (2×50 mL). The combined organic phases were dried over Na$_2$SO$_4$, filtered and evaporated to afford [4-(2-hydroxy-2-methylpropoxy)phenyl]acetic acid (106MBT52-D, 470 mg, 70%) as a colourless solid. $^1$H-NMR (CDCl$_3$): δ 7.19 (m, 2H), 6.88 (m, 2H), 3.78 (s, 2H), 3.57 (s, 2H), 1.34 (s. 6H).

The acid 106MBT52-D (150 mg, 0.67 mmol) was dissolved in dichloromethane (10 mL). N-{1-[2-(1,3-dioxan-2-yl)ethyl]piperidin-4-yl}-N-(4-fluorobenzyl)amine (118AF52-95, 180 mg, 0.56 mmol) was added followed by triethylamine (235 μL, 0.84 mmol). Bromo-tris-pyrrolidino-phosphonium hexafluorophosphate (PyBroP, 392 mg, 0.84 mmol) was added, and the mixture was stirred at room temperature for 2 h. The mixture was concentrated and passed onto a prewashed (methanol) ion exchange column (0.88 mmol/g, 1 g). The column was washed with methanol (8×4 mL) and the remaining product was eluted off the column with 10% NH$_4$OH in methanol (2×4 mL) and evaporated. The resulting oil was dissolved in dichloromethane (20 mL) and washed with saturated aqueous NaHCO$_3$ (5×20 mL). The organic phase was dried over Na$_2$SO$_4$, filtered and evaporated. The resulting oil was purified by flash chromatography (0-5% methanol in dichloromethane) to give a colourless oil (110 mg, 31%). R$_f$=0.64 (MeOH/CH$_2$Cl$_2$ 1:9). LCMS m/z 529 [M+H]$^+$. $^1$H-NMR (CDCl$_3$, rotamers 0.4:0.6): δ 7.25-6.82 (m, 8H), 4.64-4.48 (m, 2.4H), 4.44 (s, 1.2H), 4.10-4.03 (m, 2H), 3.79-3.67 (m, 5.2H), 3.50 (s, 1.2H), 2.90-2.81 (m, 2H), 2.42-3.95 (m, 2H), 2.12-1.98 (m, 2.2H), 1.87-1.79 (m, 0.8H), 1.76-1.48 (m, 5.2H), 1.36-1.27 (m, 7.8H). HPLC t$_R$=6.1 min.

The collected compound was converted into its tartrate salt, which was obtained as a colourless solid (106MBT54-D).

N-(4-Fluorobenyzl)-N-(piperidin-4-yl)-2-(4-isobutoxyphenyl)acetamide (103NLS56)

To a solution of the amine 118AF93-51 (10.37 g, 30.3 mmol) and triethylamine (9.36 mL, 60.6 mmol) in dichloromethane (200 mL) a solution of 4-isobutoxyphenylacetyl chloride 128NLS28 (8.93 g, 39.4 mmol) in dichloromethane (100 mL) is added dropwise at 0° C. The solution is stirred at rt for 3h, then water is added and the mixture washed with sat. aq. NaHCO3. The organic layer was washed with 5% HCl, water and brine, dried over sodium sulfate, filtered and evaporated in vacuo. The residue was purified by silica gel column chromatography eluting with a stepwise gradient of 0-50% ethyl acetate in n-heptane, affording N-(4-fluorobenzyl)-N-[1-(benzyloxycarbonyl)piperidin-4-yl]-2-(4-isobutoxyphenyl)acetamide as a colourless oil.

This compound was dissolved in abs. ethanol (200 mL) and hydrogenated overnight at rt using Pd/C (10%, 1 g) as a catalyst. The mixture was filtered over Celite, the solvent removed and the residue dried in vacuo to give a colourless oil (7.02 g, 58% over both steps). This compound was used without further purification. LCMS m/z 399 [M+H]$^+$. HPLC t$_R$=8.8 min.

N-{1-[3-(3,5-Dimethylpiperidin-1-yl)propyl]piperidin-4-yl}-N-(4-fluorobenzyl)-2-(4-isobutoxyphenyl)acetamide, dihydrochloride (103NLS45-B)

To 3,5-dimethylpiperidine (43 μL, 0.33 mmol) in DMF (1 mL) was added potassium carbonate (132 mg, 1.0 mmol), followed by 1-chloro-3-iodopropane (32 μmol, 0.30 mmol) and the mixture stirred at 50° C. for 2 h. After cooling to rt, a solution of 103NLS56 (100 mg, 0.25 mmol) in DMF (0.5 mL) was added, followed by sodium iodide (45 mg, 0.30 mmol). The mixture was shaken for 20 h at 60° C., filtered, evaporated to dryness and purified by silica gel column chromatography, eluting with a stepwise gradient of 0-10% methanol in dichloromethane. The residue was further purified by passage over a reversed phase C$_{18}$ SPE cartridge, giving the desired compound (35 mg, 25%), which was converted into its dihydrochloride salt.

R$_f$=0.61 (MeOH/CH$_2$Cl$_2$ 1:9). LCMS m/z 552 [M+H]$^+$. HPLC t$_R$=8.7 min.

1-[3-(4-{(4-Fluorobenzyl)-[2-(4-isobutoxyphenyl)acetyl]amino}piperidin-1-yl)propyl]piperidine-4-carboxylic acid methyl ester, dihydrochloride (103NLS45-E)

Prepared following the same method as described for 103NLS45-B, using piperidine-4-carboxylic acid methyl ester (44 μL, 0.33 mmol). Yield: 7 mg, 5%.

LCMS m/z 582 [M+H]$^+$. HPLC t$_R$=7.8 min.

N-(4-Fluorobenzyl)-2-(4-isobutoxyphenyl)-N-{1-[2-(1-methylpyrrolidin-2-yl)ethyl]piperidin-4-yl}acetamide, dioxalate (103NLS63-G)

To a solution of the amine 103NLS56 (15 mg, 0.038 mmol) in DMF (0.3 mL) was added a solution of 2-(2-chloroethyl)-1-methylpyrrolidine hydrochloride (8.4 mg, 0.045 mmol) in DMF (0.1 mL), followed by caesium carbonate (50 mg, 0.15 mmol) and sodium iodide (6.8 mg, 0.045 mmol). The mixture was stirred overnight at 60° C., partitioned between dichloromethane and sat. aq. NaHCO$_3$ solution. The organic layer was dried over sodium sulfate, filtered and evaporated. The residue was purified by preparative reversed phase ($C_{18}$) HPLC and the obtained compound (10.5 mg, 54%) converted into its dioxalate salt.

LCMS m/z 510 [M+H]$^+$. HPLC $t_R$=8.1 min.

N-{1-[3-(2,6-Dimethylmorpholin-4-yl)propyl]piperidin-4-yl}-N-(4-fluorobenzyl)-2-(4-isobutoxyphenyl)acetamide, dioxalate (103NLS69-A)

To a solution of 2,6-dimethylmorpholine (6.1 µL, 49 µmol) in DMF (0.3 mL) 1-chloro-3-iodopropane (4.9 µL, 45 µmol) in DMF (0.05 mL) was added, followed by caesium carbonate (50 mg, 0.15 mmol). The mixture was shaken at 50° C. for 3 h. After cooling to rt, the piperidine derivative 103NLS56 (15 mg, 38 µmol) in DMF (0.1 mL) and sodium iodide (6.8 mg, 45 µmol) were added and stirring maintained overnight at 60° C. The mixture was partitioned between dichloromethane and sat. aq. NaHCO$_3$ solution. The organic layer was dried over sodium sulfate, filtered and evaporated. The residue was purified by preparative reversed phase ($C_{18}$) HPLC and the obtained compound (6.3 mg, 30%) converted into its dioxolate salt.

LCMS m/z 554 [M+H]$^+$. HPLC $t_R$=8.7 min.

N-(4-Fluorobenzyl)-N-{1-[3-(3-hydroxypiperidin-1-yl)propyl]piperidin-4-yl}-2-(4-isobutoxyphenyl)acetamide, dioxalate (103NLS69-B)

Prepared following the same method as described for 103NLS69-A, using 3-hydroxypiperidine hydrochloride (6.8 mg, 49 µmol). Yield: 7.9 mg, 30%. LCMS m/z 540 [M+H]$^+$. HPLC $t_R$=8.1 min.

N-(4-Fluorobenzyl)-2-(4-isobutoxyphenyl)-N-{1-[3-(2-methylpiperidin-1-yl)propyl]piperidin-4-yl}acetamide, dioxalate (103NLS69-C)

Prepared following the same method as described for 103NLS69-A, using 2-methylpiperidine (5.8 µL, 49 µmol). Yield: 5.2 mg, 26%. LCMS m/z 538 [M+H]$^+$. HPLC $t_R$=8.7 min.

N-(4-Fluorobenzyl)-2-(4-isobutoxyphenyl)-N-[1-(3-pyrrolidin-1-yl-propyl)piperidin-4-yl]acetamide, dioxalate (103NLS69-D Prepared following the same method as described for 103NLS69-A, using pyrrolidine (5.0 µL, 49 µmol). Yield: 4.6 mg, 24%. LCMS m/z 510 [M+H]$^+$. HPLC $t_R$=8.4 min.

N-{1-[3-(2,5-Dimethylpyrrolidin-1-yl)propyl]piperidin-4-yl}-N-(4-fluorobenzyl)-2-(4-isobutoxyphenyl)acetamide, dioxalate (103NLS69-E)

Prepared following the same method as described for 103NLS69-A, using 2,5-dimethylpyrrolidine (6.0 µL, 49 µmol). Yield: 3.4 mg, 17%. LCMS m/z 538 [M+H]$^+$. HPLC $t_R$=8.7 min.

N-(4-Fluorobenzyl)-N-{1-[3-(3-hydroxymethylpiperidin-1-yl)propyl]piperidin-4-yl}-2-(4-isobutoxyphenyl)acetamide, dioxalate (103NLS69-F)

Prepared following the same method as described for 103NLS69-A, using 3-hydroxymethylpiperidine (5.5 µL, 49 µmol). Yield: 5.5 mg, 26%. LCMS m/z 554 [M+H]$^+$. HPLC $t_R$=8.0 min.

(4S)-3-(3-chloropropyl)-4-isopropyloxazolidinon-2-one (103NLS94)

Sodium hydride (60% suspension in oil, 288 mg, 7.2 mmol) was added to a solution of (S)-4-isopropyl-2-oxazolidinone (775 mg, 6.0 mmol) in dry tetrahydrofuran (50 mL) under argon atmosphere. The suspension was stirred for 15 min at rt, then 1-bromo-3-chloropropane (1.18 mL, 12.0 mmol) was added dropwise over 30 min. The mixture was refluxed overnight, filtered and the filtrate evaporated in vacuo. Purification of the residue by silica gel column chromatography, eluting with a stepwise gradient of 0-4% methanol in dichloromethane afforded (4S)-3-(3-chloropropyl)-4-isopropyloxazolidinon-2-one (824 mg, 67%) as a colourless oil.

N-(4-Fluorobenzyl)-2-(4-isobutoxyphenyl)-N-{1-[3-(4-(S)-isopropyl-2-oxo-oxazolidin-3-yl)propyl]piperidin-4-yl}acetamide, oxalate (117NLS01)

To a solution of 103NLS56 (207 mg, 0.52 mmol) potassium carbonate (215 mg, 1.56 mmol) was added, followed by the alkylating agent 103NLS94 (127 mg, 0.62 mmol) and sodium iodide (93 mg, 0.62 mmol). The mixture was stirred at 65° C. overnight, the solvent removed and the residue partitioned between ethyl acetate and water. The organic layer was dried over Na$_2$SO$_4$, filtered and evaporated. The residue was purified by silica gel column chromatography, eluting with a stepwise gradient of 0-4% methanol in dichloromethane. Further purification of the compound was performed by passage over an acidic ion exchange SPE cartridge, affording the desired compound (209 mg, 71%) as a colourless oil, which was converted into its oxalate salt.

$R_f$=0.35 (MeOH/CH$_2$Cl$_2$ 5:95). LCMS m/z 568 [M+H]$^+$. $^1$H-NMR (CDCl$_3$, rotamers 0.6:0.4) δ 7.21-6.80 (m, 8H, Ar—H), 4.60-4.53 (m, 0.6H, pip-H), 4.49 and 4.43 (2s, 2H, benzyl-H), 4.19-4.14 (m, 1H, oxa-CH$_2$), 4.06-4.01 (m, 1H, oxa-CH$_2$), 3.77-3.67 (m, 4.2H, pip-H, oxa-NCH, CH$_{2OiBu}$, benzyl-H), 3.53-3.46 (m, 2.2H, benzyl-H, OCONCH$_2$), 2.98-2.85 (m, 3H, pip-H, OCONCH$_2$), 2.39-2.25 (m, 2H, NCH$_2$), 2.10-2.00 (m, 3.2H, CH(CH$_3$)$_2$, pip-H, CH$_{OiBu}$), 1.85-1.50 (m, 6H, pip-H, NCH$_2$CH$_2$), 1.29 (m, 0.8H, pip-H), 1.01-0.99 (m, 6H, CH$_{3OiBu}$), 0.89-0.83 (m, 6H, CH(CH$_3$)$_2$). HPLC $t_R$=8.9 min.

N-[2-(4-Fluorophenyl)ethyl]-2-(4-isobutoxyphenyl)-N-{1-[3-(4-(S)-isopropyl-2-oxo-oxazolidin-3-yl)propyl]piperidin-4-yl}acetamide, oxalate (117NLS03-A)

Prepared following the same method as described for 117NLS01 using N-[2-(4-fluorophenyl)ethyl]-2-(4-isobutoxyphenyl)-N-(piperidin-4-yl)acetamide (111 mg, 0.27 mmol, prepared by the procedure described for 103NLS56). Yield: 90 mg, 57%.

$R_f$=0.30 (MeOH/CH$_2$Cl$_2$ 5:95). LCMS m/z 582 [M+H]$^+$. $^1$H-NMR (CDCl$_3$, rotamers 0.6:0.4) δ 7.18-6.80 (m, 8H, Ar—H), 4.40-4.35 (m, 0.4H, pip-H), 4.20-4.15 (m, 1H, oxa-CH$_2$), 4.05-4.01 (m, 1H, oxa-CH$_2$), 3.75-3.46 (m, 6.6H, pip-H, oxa-NCH, CH$_{2OiBu}$, benzyl-H, OCONCH$_2$), 3.36 (m, 2H, ArCH$_2$CH$_2$N), 3.02-2.84 (m, 3H, pip-H, OCONCH$_2$), 2.81-2.75 (m, 2H, ArCH$_2$), 2.37-2.25 (m, 2H, NCH$_2$), 2.09-1.98 (m, 2.8H, CH(CH$_3$)$_2$, pip-H, CH$_{OiBu}$), 1.85-1.62 (m, 6H, pip-H, NCH$_2$CH$_2$), 1.31 (m, 1.2H, pip-H), 1.00-0.97 (m, 6H, CH$_{3OiBu}$), 0.89-0.84 (m, 6H, CH(CH$_3$)$_2$). HPLC $t_R$=9.1 min.

N-[2-(4-Fluorophenyl)ethyl]-N-{1-[3-(4-(S)-isopropyl-2-oxo-oxazolidin-3-yl)propyl]piperidin-4-yl}-2-(4-propoxyphenyl)acetamide, oxalate (117NLS03-B)

Prepared following the same method as described for 117NLS01 using N-[2-(4-fluorophenyl)ethyl]-N-(piperidin-4-yl)-2-(4-propoxyphenyl)acetamide (108 mg, 0.27 mmol, prepared by the procedure described for 103NLS56). Yield: 76 mg, 50%.

$R_f$=0.33 (MeOH/CH$_2$Cl$_2$ 5:95). LCMS m/z 568 [M+H]$^+$. $^1$H-NMR (CDCl$_3$, rotamers 0.6:0.4) δ 7.17-6.81 (m, 8H, Ar—H), 4.40-4.35 (m, 0.4H, pip-H), 4.20-4.15 (m, 1H, oxa-CH$_2$), 4.05-4.01 (m, 1H, oxa-CH$_2$), 3.90-3.85 (m, 2H, OCH$_{2OPr}$), 3.72-3.48 (m, 4.6H, pip-H, oxa-NCH, benzyl-H, OCONCH$_2$), 3.36-3.30 (m, 2H, ArCH$_2$CH$_2$N), 2.99-2.86 (m, 3H, pip-H, OCONCH$_2$), 2.80-2.74 (m, 2H, ArCH$_2$), 2.38-2.26 (m, 2H, NCH$_2$), 2.11-2.03 (m, 1.8H, CH(CH$_3$)$_2$, pip-H), 1.87-1.64 (m, 8H, pip-H, CH$_{2OPr}$, NCH$_2$CH$_2$), 1.31 (m, 1.2H, pip-H), 1.03-0.98 (m, 3H, CH$_{3OPr}$), 0.88-0.83 (m, 6H, CH(CH$_3$)$_2$). HPLC $t_R$=8.5 min.

N-(4-Fluorobenzyl)-N-{1-[3-(4-(S)-isopropyl-2-oxo-oxazolidin-3-yl)propyl]piperidin-4-yl}-2-(4-propoxyphenyl)acetamide, oxalate (117NLS03-C)

Prepared following the same method as described for 117NLS01 using N-(4-fluorobenzyl)-N-(piperidin-4-yl)-2-(4-propoxyphenyl)acetamide (104 mg, 0.27 mmol, prepared by the procedure described for 103NLS56). Yield: 120 mg, 80%.

$R_f$=0.36 (MeOH/CH$_2$Cl$_2$ 5:95). LCMS m/z 554 [M+H]$^+$. $^1$H-NMR (CDCl$_3$, rotamers 0.6:0.4) δ 7.19-6.78 (m, 8H, Ar—H), 4.57-4.48 (m, 0.6H, pip-H), 4.48 and 4.42 (2s, 2H, benzyl-H), 4.18-4.12 (m, 1H, oxa-CH$_2$), 4.04-4.00 (m, 1H, oxa-CH$_2$), 3.91-3.85 (m, 2H, OCH$_{2OPr}$), 3.75-3.66 (m, 2.2H, pip-H, oxa-NCH, benzyl-H), 3.49-3.43 (m, 2.2H, benzyl-H, OCONCH$_2$), 2.98-2.80 (m, 3H, pip-H, OCONCH$_2$), 2.33-2.25 (m, 2H, NCH$_2$), 2.05-1.50 (m, 10.2H, CH(CH$_3$)$_2$, NCH$_2$CH$_2$, pip-H, CH$_{2OPr}$), 1.27 (m, 0.8H, pip-H), 1.18-0.98 (m, 3H, CH$_{3OPr}$), 0.87-0.81 (m, 6H, CH(CH$_3$)$_2$). HPLC $t_R$=8.3 min.

N-{1-[2-(1,3-Dioxan-2-yl)ethyl]piperidin-4-yl}-N-(4-fluorobenzyl)-2-(4-isobutoxyphenyl)acetamide, oxalate (103NLS63-F)

Prepared following the same method as described for 117NLS01 using and 103NLS56 (262 mg, 0.657 mmol) and 2-(2-bromoethyl)-1,3-dioxane as the alkylating agent. No sodium iodide was required. Yield: 152 mg, 45%.

$R_f$=0.35 (MeOH/CH$_2$Cl$_2$ 1:9). LCMS m/z 513 [M+H]$^+$. $^1$H-NMR (CDCl$_3$, rotamers 0.6:0.4) δ 7.26-6.80 (m, 8H, Ar—H), 4.63-4.39 (m, 3.6H, pip-H, dioxane-H, benzyl-H), 4.09-4.01 (m, 2H, dioxane-H), 3.78-3.64 (m, 5.2H, pip-H, dioxane-H, CH$_{2OiBu}$, benzyl-H), 3.50 (s, 1.2H, benzyl-H), 2.92-2.79 (m, 2H, pip-H), 2.43-2.34 (m, 2H, NCH$_2$), 2.10-1.96 (m, 3.2H, dioxane-H, pip-H, CH$_{OiBu}$), 1.88-1.48 (m, 6H, pip-H, NCH$_2$CH$_2$), 1.35-1.24 (m, 1.8H, dioxane-H, pip-H), 1.01 (m, 6H, CH$_{3OiBu}$). HPLC $t_R$=8.8 min.

N-{1-[2-(1,3-Dioxan-2-yl)ethyl]piperidin-4-yl}-N-[2-(4-fluorophenyl)ethyl]-2-(4-isobutoxyphenyl)acetamide, oxalate (117NLS03-D)

Prepared following the same method as described for 117NLS03-A using 2-(2-bromoethyl)-1,3-dioxane as the alkylating agent. No sodium iodide was required. Yield: 99 mg, 70%.

$R_f$=0.35 (MeOH/CH$_2$Cl$_2$ 5:95). LCMS m/z 527 [M+H]$^+$. $^1$H-NMR (CDCl$_3$, rotamers 0.7:0.3) δ7.18-6.80 (m, 8H, Ar—H), 4.58-4.54 (m, 1H, dioxane-H), 4.48-4.41 (m, 0.3H, pip-H), 4.10-4.06 (m, 2H, dioxane-H), 3.77-3.66 (m, 5.4H, dioxane-H, benzyl-H, CH$_{2OiBu}$), 3.64-3.52 (m, 1.3H, benzyl-H, pip-H), 3.37-3.32 (m, 2H, CH$_2$NCO), 2.99 and 2.89 (2m, 2H, pip-H), 2.82-2.76 (m, 2H, ArCH$_2$), 2.49-2.39 (m, 2H, NCH$_2$), 2.12-2.00 (m, 2.6H, dioxane-H, pip-H, CH$_{OiBu}$), 1.88-1.67 (m, 6H, pip-H, CH$_{2OiBu}$, NCH$_2$CH$_2$), 1.35-1.31 (m, 2.4H, dioxane-H, pip-H), 1.00 (t, 6H, J=6.6, CH$_{3OiBu}$). HPLC $t_R$=8.8 min.

N-{1-[2-(1,3-Dioxan-2-yl)ethyl]piperidin-4-yl}-N-[2-(4-fluorophenyl)ethyl]-2-(4-propoxyphenyl)acetamide, oxalate (117NLS03-E)

Prepared following the same method as described for 117NLS03-B using 2-(2-bromoethyl)-1,3-dioxane as the alkylating agent. No sodium iodide was required. Yield: 90 mg, 65%.

$R_f$=0.23 (MeOH/CH$_2$Cl$_2$ 5:95). LCMS m/z 513 [M+H]$^+$. $^1$H-NMR (CDCl$_3$, rotamers 0.7:0.3) δ 7.21-6.81 (m, 8H, Ar—H), 4.58-4.54 (m, 1H, dioxane-H), 4.48-4.42 (m 0.3H, pip-H), 4.10-4.06 (m, 2H, dioxane-H), 3.91-3.86 (m, 2H, CH$_{2OPr}$), 3.77-3.69 (m, 3.4H, dioxane-H, benzyl-H), 3.63-3.56 (m, 1.3H, benzyl-H, pip-H), 3.38-3.31 (m, 2H, CH$_2$NCO), 2.99 and 2.89 (2m, 2H, pip-H), 2.82-2.76 (m, 2H, ArCH$_2$), 2.49-2.39 (m, 2H, NCH$_2$), 2.12-2.00 (m, 1.6H, dioxane-H, pip-H), 1.87-1.65 (m, 8H, pip-H, CH$_{2OPr}$, NCH$_2$CH$_2$), 1.35-1.31 (m, 2.4H, dioxane-H, pip-H), 1.05-1.00 (m, 3H, CH$_{3OPr}$). HPLC $t_R$=8.0 min.

N-{1-[2-(1,3-Dioxan-2-yl)ethyl]piperidin-4-yl}-N-(4-fluorobenzyl)-2-(4-propoxyphenyl)acetamide, tartrate (117NLS03-F)

Prepared following the same method as described for 117NLS03-C using 2-(2-bromoethyl)-1,3-dioxane as the alkylating agent. No sodium iodide was required. Yield: 107 mg, 79%.

$R_f$=0.41 (MeOH/CH$_2$Cl$_2$ 5:95). LCMS m/z 499 [M+H]$^+$. $^1$H-NMR (CDCl$_3$, rotamers 0.6:0.4) δ 7.20-6.80 (m, 8H, Ar—H), 4.62-4.56 (m, 0.6H, pip-H), 4.54-4.51 (m, 1H, dioxane-H), 4.49 and 4.43 (2s, 2H, benzyl-H), 4.08-4.04 (m, 2H, dioxane-H), 3.92-3.87 (m, 2H, OCH$_{2OPr}$), 3.76-3.68 (m, 3.2H, pip-H, dioxane-H, benzyl-H), 3.50 (s, 1.2H, benzyl-H), 2.90-2.83 (m, 2H, pip-H), 2.43-2.36 (m, 2H, NCH$_2$), 2.10-1.98 (m, 2.2H, dioxane-H, pip-H,), 1.86-1.51 (m, 8H, pip-H, CH$_{2OPr}$, NCH$_2$CH$_2$), 1.32-1.27 (m, 1.8H, dioxane-H, pip-H), 1.05-0.99 (m, 3H, CH$_3$). HPLC $t_R$=7.6 min.

N-{1-[2-(1,3-Dioxan-2-yl)ethyl]piperidin-4-yl}-N-(4-fluorobenzyl)-N'-(4-isobutoxybenzyl)carbamide, tartrate (117NLS25)

Prepared following the same method as described for 117NLS01 using 2-(2-bromoethyl)-1,3-dioxane (24 µL, 0.18 mmol) as the alkylating agent and N-(4-fluorobenzyl)-N'-(4-isobutoxybenzyl)-N-(piperidin-4-yl)carbamide (76ELH18, 50 mg, 0.12 mmol). No sodium iodide was required. Yield: 38 mg, 60%.

$R_f$=0.32 (MeOH/CH$_2$Cl$_2$ 1:9). LCMS m/z 528 [M+H]$^+$. $^1$H-NMR (CDCl$_3$) δ 7.18-6.74 (m, 8H, Ar—H), 4.53 (t, 1H, J=5.1, dioxane-H), 4.46 (t, 1H, J=5.3, NH), 4.33-4.25 (m, 5H, pip-H, benzyl-H), 4.08-4.04 (m, 2H, dioxane-H), 3.75-3.68 (m, 2H, dioxane-H), 3.66 (d, 2H, J=6.6, CH$_{2OiBu}$), 2.93-2.88 (m, 2H, pip-H), 2.43-2.39 (m, 2H, NCH$_2$), 2.09-1.98 (m, 4H, CH$_{OiBu}$, dioxane-H, pip-H), 1.77-1.56 (m, 6H, pip-H, NCH$_2$CH$_2$), 1.32-1.28 (m, 1H, dioxane-H), 0.99 (d, 6H, J=6.6, CH$_{3OiBu}$). HPLC t$_R$=8.7 min.

N-{1-[2-(1,3-Dioxan-2-yl)ethyl]piperidin-4-yl}-N-(4-fluorobenzyl)-2-(4-fluorophenyl)acetamide, tartrate (117NLS87-A)

To a solution of 118AF52-95 (300 mg, 0.93 mmol) and triethylamine (0.52 mL, 3.72 mmol) in dry THF (10 mL) at 0° C. a solution of 4-fluorophenylacetyl chloride (0.19 mL, 1.39 mmol) in THF (5 mL) was added dropwise and stirring was continued at rt for 3 h. The reaction mixture was filtered and the filtrate evaporated to dryness. The residue was partitioned between ethyl acetate and 1M NaOH, the organic layer washed with brine, dried over Na$_2$SO$_4$, filtered and evaporated. Purification by silica gel column chromatography, eluting with a stepwise gradient of 0-8% methanol in dichloromethane, followed by purification of the compound by passage over an acidic ion exchange SPE cartridge, afforded the desired compound (131 mg, 31%), which was converted to its tartrate form as described above.

R$_f$=0.39 (MeOH/CH$_2$Cl$_2$ 1:9). LCMS m/z 459 [M+H]$^+$. $^1$H-NMR (CDCl$_3$, rotamers 0.6:0.4) δ 7.25-6.88 (m, 8H, Ar—H), 4.58-4.52 (m, 0.6H, pip-H), 4.50 (t, 1H, J=5.1, dioxane-H), 4.48 and 4.44 (2s, 2H, benzyl-H), 4.06-4.02 (m, 2H, dioxane-H), 3.78 and 3.50 (2s, 2H, benzyl-H), 3.72-3.64 (m, 2.4H, pip-H, dioxane-H), 2.84 (m, 2H, pip-H), 2.40-2.35 (m, 2H, NCH$_2$), 2.07-1.99 (m, 2.2H, dioxane-H, pip-H), 1.85-1.50 (m, 6H, pip-H, NCH$_2$CH$_2$), 1.30-1.25 (m, 1.8H, dioxane-H, pip-H). HPLC t$_R$=6.9 min.

N-{1-[2-(1,3-Dioxan-2-yl)ethyl]piperidin-4-yl}-N-(4-fluorobenzyl)-2-p-tolylacetamide, tartrate (117NLS87-B)

Prepared following the same method as described for 117NLS87-A using 4-methylphenylacetyl chloride and 118AF52-95 (300 mg, 0.93 mmol). Yield: 119 mg, 28%.

R$_f$=0.43 (MeOH/CH$_2$Cl$_2$ 1:9). LCMS m/z 455 [M+H]$^+$. $^1$H-NMR (CDCl$_3$, rotamers 0.5:0.5) δ 7.17-6.87 (m, 8H, Ar—H), 4.60-4.53 (m, 0.5H, pip-H), 4.50 (t, 1H, J=5.1, dioxane-H), 4.48 and 4.41 (2s, 2H, benzyl-H), 4.05-4.01 (m, 2H, dioxane-H), 3.77-3.66 (m, 3.5H, pip-H, benzyl-H, dioxane-H), 3.50 (s, 1H, benzyl-H), 2.87-2.80 (m, 2H, pip-H), 2.40-2.34 (m, 2H, NCH$_2$), 2.30 and 2.28 (2s, 3H, CH$_3$), 2.07-1.95 (m, 2H, dioxane-H, pip-H), 1.83-1.50 (m, 6H, pip-H, NCH$_2$CH$_2$), 1.29-1.25 (m, 2H, dioxane-H, pip-H). HPLC t$_R$=7.7 min.

2-Benzofuran-5-yl-N-{1-[2-(1,3-dioxan-2-yl)ethyl]piperidin-4-yl}-N-(4-fluorobenzyl)acetamide, tartrate (128NLS22-A)

Benzofuran-5-yl-acetic acid was prepared adapting a procedure by Dunn et al. (*J. Med. Chem.*, 1986, 29, 2326) and converted into the corresponding acetyl chloride by treatment with oxalylchloride. The title compound was prepared from 118AF52-95 (58 mg, 0.18 mmol) following the same method as described for 117NLS87-A. Yield: 27 mg, 43%.

R$_f$=0.52 (MeOH/CH$_2$Cl$_2$ 1:9). LCMS m/z 481 [M+H]$^+$. $^1$H-NMR (CDCl$_3$, rotamers 0.6:0.4) δ 7.64-6.68 (m, 9H, Ar—H), 4.62-4.54 (m, 0.6H, pip-H) 4.53-4.44 (m, 3H, dioxane-H, benzyl-H), 4.07-4.03 (m, 2H, dioxane-H), 3.82-3.61 (m, 3.2H, pip-H, benzyl-H, dioxane-H), 3.45 (s, 1.2H, benzyl-H), 2.91-2.80 (m, 2H, pip-H), 2.44-2.35 (m, 2H, NCH$_2$), 2.08-1.98 (m, 2.2H, dioxane-H, pip-H), 1.85-1.56 (m, 6H, pip-H, NCH$_2$CH$_2$), 1.32-1.27 (m, 1.8H, dioxane-H, pip-H). HPLC t$_R$=6.6 min.

2-(2,3-Dihydrobenzofuran-5-yl)-N-{1-[2-(1,3-dioxan-2-yl)ethyl]piperidin-4-yl}-N-(4-fluorobenzyl) acetamide, tartrate (128NLS22-B)

The compound (2,3-Dihydrobenzofuran-5-yl)acetic acid was prepared adapting a procedure by Dunn et al. (*J. Med. Chem.*, 1986, 29, 2326) and converted into the corresponding acetyl chloride by treatment with oxalylchloride. The title compound was prepared from 118AF52-95 (58 mg, 0.18 mmol) following the same method as described for 117NLS87-A. Yield: 27 mg, 31%.

R$_f$=0.50 (MeOH/CH$_2$Cl$_2$ 1:9). LCMS m/z 483 [M+H]$^+$. $^1$H-NMR (CDCl$_3$, rotamers 0.6:0.4) δ 7.10-6.60 (m, 7H, Ar—H), 4.55-4.40 (m, 5.6H, pip-H, dioxane-H. benzyl-H, ArOCH$_2$), 4.01-3.97 (m, 2H, dioxane-H), 3.72-3.62 (m, 3.2H, pip-H, benzyl-H, dioxane-H), 3.41 (s, 1.2H, benzyl-H), 3.14-3.06 (m, 2H, OCH$_2$CH$_2$), 2.80 (m, 2H, pip-H), 2.35-2.30 (m, 2H, NCH$_2$), 1.99-1.93 (m, 2.2H, dioxane-H, pip-H), 1.80-1.44 (m, 6H, pip-H, NCH$_2$CH$_2$), 1.27-1.22 (m, 1.8H, dioxane-H, pip-H). HPLC t$_R$=6.9 min.

N-{1-[2-(2,2-Dimethyl-1,3-dioxolan-4-yl)ethyl]piperidin-4-yl}-N-(4-fluorobenzyl)-2-(4-isobutoxyphenyl)acetamide, tartrate (117NLS37)

1-(2',2'-Dimethyl-1',3'-dioxolan-4'-yl)ethanol was prepared according to literature procedures (Carman R. M et al., *Aust. J. Chem.*, 1998, 51, 955) and oxidized to the aldehyde by treatment with pyridinium chlorochromate. The crude aldehyde (80 mg, 0.55 mmol) was added to a solution of 103NLS56 (184 mg, 0.46 mmol) in methanol (5 mL). Acetic acid (0.05 mL) was added, followed by sodium cyanoborohydride (58 mg, 0.92 mmol) and the mixture stirred overnight at rt. The solvent was removed and the residue partitioned between dichloromethane and 1M NaOH. The organic layer was washed with sat. NH$_4$Cl, dried over Na$_2$SO$_4$, filtered and evaporated. Purification by silica gel column chromatography eluting with 0-5% methanol in dichloromethane afforded the desired compound (50 mg, 21%), which was converted into its tartrate salt.

R$_f$=0.39 (MeOH/CH$_2$Cl$_2$ 1:9). LCMS m/z 527 [M+H]$^+$. $^1$H-NMR (CDCl$_3$, rotamers 0.6:0.4) δ 7.22-6.79 (m, 8H, Ar—H), 4.62-4.54 (m, 0.6H, pip-H), 4.49 and 4.42 (2s, 2H, benzyl-H), 4.06-3.98 (m, 1H, dioxolane-H), 3.75-3.66 (m,4.4H, pip-H, CH$_{2OiBu}$, benzyl-H), 3.48 (m, 2H, dioxolane-H), 2.89-2.83 (m, 2H, pip-H), 2.45-2.25 (m, 2H, NCH$_2$), 2.07-1.99 (m, 2.2H, pip-H, CH$_{OiBu}$), 1.85-1.51 (m, 6H, pip-H, NCH$_2$CH$_2$), 1.36-1.28 (m, 6.8H, C(CH$_3$)$_2$, pip-H), 1.02-0.99 (m, 6H, CH$_{3OiBu}$). HPLC t$_R$=9.3 min.

4-[2-(Tosyloxy)ethyl]-1,3-dioxane (128NLS46-B)

A suspension of 1,3,5-pentanetriol (1.01 g, 8.33 mmol), paraformaldehyde (0.46 g) and methanesulfonic acid (0.33 mL) in DMF (3 mL) is heated for 10 min at 130° C. under microwave irradiation. The mixture was partitioned between ethyl acetate and water, the organic layer dried over Na$_2$SO$_4$, filtered and evaporated. The residue was dissolved in methanol (3 mL), conc. HCl (0.09 mL) added, and the mixture heated at 80° C. for 10 min under microwave irradiation. Ethyl acetate and 2M NaOH were added, the aqueous layer extracted twice with ethyl acetate and the combined organic layers washed with brine, dried over Na$_2$SO$_4$, filtered and evaporated. The crude product was treated with p-tosylchloride and DMAP following literature procedures (Moune et al., *J. Org. Chem.*, 1997, 62, 3332). The title compound (1.18 g, 49% overall crude yield) was obtained as a yellowish oil, which was used without purification.

N-{1-[2-(1,3-Dioxan-4-yl)ethyl]piperidin-4-yl}-N-(4-fluorobenzyl)amine (128NLS52)

To a suspension of 4-piperidone monohydrate hydrochloride (1.26 g, 8.23 mmol) in acetonitrile (100 mL), potassium carbonate (3.4 g, 24.6 mmol) was added, followed by the tosylate 128NLS46-B (3.54 g, 12.36 mmol) and sodium iodide (1.85 g, 12.35 mmol) and stirring was continued overnight at 60° C. The mixture was filtered, the filtrate evaporated in vacuo and the residue partitioned between 1M NaOH and ethyl acetate. The organic layer was separated, the aqueous layer extracted twice with ethyl acetate and the combined organic layers dried over sodium sulphate, filtered and evaporated to dryness. Purification of the residue by silica gel column chromatography, eluting with a stepwise gradient of 0-4% methanol in dichloromethane, afforded 1-[2-(1,3-dioxan-4-yl)ethyl]piperidin-4-one (128NLS50, 1.73 g, 98%).

To a solution of 128NLS50 (1.73 g, 8.13 mmol) in methanol (100 mL) was added dropwise 4-fluorobenzylamine (0.93 mL, 8.13 mmol) and acetic acid. Sodium cyanoborohydride (2.15 g, 40 mmol) was added slowly to the mixture at 0° C. and stirring was continued at rt overnight. The reaction mixture was concentrated in vacuo and the residue partitioned between dichloromethane and 1M NaOH, the aqueous layer extracted twice with dichloromethane and the combined organic layers dried over $Na_2SO_4$, filtered and evaporated to dryness. Purification of the residue by a short silica gel column chromatography eluting with 0-30% methanol in dichloromethane gave the title compound (1.51 g, 58%) as a colourless solid.

N-{1-[2-(1,3-Dioxan-4-yl)ethyl]piperidin-4-yl}-N-(4-fluorobenzyl)-2-(4-isobutoxyphenyl)acetamide, tartrate (128NLS62).

Prepared following the same method as described for 117NLS87-A using 4-isobutoxyphenylacetyl chloride and 128NLS52 (480 mg, 1.49 mmol). Yield: 458 mg, 60%.

$R_f$=0.36 (MeOH/$CH_2Cl_2$ 1:9). LCMS m/z 513 [M+H]$^+$. $^1$H-NMR (CDCl$_3$, rotamers 0.6:0.4) δ 7.21-6.80 (m, 8H, Ar—H), 5.01 (d, 1H, J=6.1, dioxane-H), 4.66-4.56 (m, 1.6H, pip-H, dioxane-H) 4.51 and 4.44 (2s, 2H, benzyl-H), 4.09-4.05 (m, 1H, dioxane-H), 3.77 and 3.51 (2s, 2H, benzyl-H), 3.70-3.57 (m, 4.4H, pip-H, dioxane-H, $CH_{2OiBu}$), 2.91-2.83 (m, 2H, pip-H), 2.45-2.34 (m, 2H, $NCH_2$), 2.10-2.00 (m, 2.2H, pip-H, $CH_{OiBu}$), 1.85-1.26 (m, 8.8H, pip-H, dioxane-H, $NCH_2CH_2$), 1.03-1.00 (m, 6H, $CH_{3OiBu}$). HPLC $t_R$=8.8 min.

N-{1-[2-(1,3-Dioxan-4-yl)ethyl]piperidin-4-yl}-N-(4-fluorobenzyl)-2-(4-trifluoromethylphenyl)acetamide, tartrate (128NLS54-A)

Prepared following the same method as described for 117NLS87-A using 4-trifluorophenylacetyl chloride and 128NLS52 (116 mg, 0.32 mmol). Yield: 52 mg, 32%.

$R_f$=0.42 (MeOH/$CH_2Cl_2$ 1:9). LCMS m/z 509 [M+H]$^+$. $^1$H-NMR (CDCl$_3$, rotamers 0.6:0.4) δ 7.60-6.90 (m, 8H, Ar—H), 4.99 (d, 1H, J=6.1, dioxane-H), 4.65-4.54 (m, 1.6H, pip-H, dioxane-H), 4.52 and 4.47 (2s, 2H, benzyl-H), 4.07-4.04 (m, 1H, dioxane-H), 3.88 (s, 0.8H, benzyl-H), 3.69-3.56 (m, 3.6H, benzyl-H, pip-H, dioxane-H), 2.89 (m, 2H, pip-H), 2.49-2.31 (m, 2H, $NCH_2$), 2.07-1.99 (m, 1.2H, pip-H), 1.89-1.36 (m, 8.8H, pip-H, dioxane-H, $NCH_2CH_2$). HPLC $t_R$=7.3 min.

2-(4-Cyanophenyl)-N-{1-[2-(1,3-dioxan-4-yl)ethyl]piperidin-4-yl}-N-(4-fluorobenzyl)acetamide, tartrate (128NLS54-C)

4-Cyanophenylacetic acid was synthesized according a method by Jaeger et al. (*J. Chem. Soc.*, 1941, 744-747) and converted to the corresponding acetyl chloride by treatment with oxalylchloride. The title compound was prepared following the same method as described for 117NLS87-A using 4-cyanophenylacetyl chloride and 128NLS52 (116 mg, 0.32 mmol). Yield: 60 mg, 40%.

$R_f$=0.40 (MeOH/$CH_2Cl_2$ 1:9). LCMS m/z 466 [M+H]$^+$. $^1$H-NMR (CDCl$_3$, rotamers 0.7:0.3) δ 7.62-6.89 (m, 8H, Ar—H), 4.97 (d, 1H, J=6.1, dioxane-H), 4.63 (m, 1H, dioxane-H), 4.59-4.47 (m, 2.7H, pip-H, benzyl-H), 4.06-4.02 (m, 1H, dioxane-H), 3.86 (s, 0.6H, benzyl-H), 3.69-3.55 (m, 3.7H, benzyl-H, pip-H, dioxane-H), 2.91-2.86 (m, 2H, pip-H), 2.47-2.30 (m, 2H, $NCH_2$), 2.05-1.39 (m, 10H, pip-H, dioxane-H, $NCH_2CH_2$). HPLC $t_R$=4.3 min.

N-(4-Fluorobenzyl)-2-(4-isobutoxyphenyl)-N-{1-[2-(2-oxo-imidazolidin-1-yl)ethyl]piperidin-4-yl}acetamide, hydrochloride (69NLS97)

Prepared following the same method as described for 117NLS01 using 103NLS56 (240 mg, 0.60 mmol) and 1-(2-tosyloxyethyl)-2-imidazolidinone as the alkylating agent. Yield: 95 mg, 31%.

LCMS m/z 511 [M+H]$^+$. $^1$H-NMR (CD$_3$OD, rotamers 0.6:0.4) δ 7.24-6.81 (m, 8H, Ar—H), 4.56 and 4.52 (2s, 2H, benzyl-H), 4.41-4.37 and 3.93-3.88 (m, 1H, pip-H), 3.84 and 3.56 (2s, 2H, benzyl-H), 3.73-3.69 (m, 2H, $CH_{2OiBu}$), 3.46-3.20 (m, 6H, imid-$CH_2$, $NCH_2CH_2$), 2.99-2.85 (m, 2H, pip-H), 2.44 (m, 2H, $NCH_2$), 2.10-1.96 (m, 3.2H, pip-H, $CH_{OiBu}$), 1.67-1.62 (m, 3H, pip-H), 1.30 (m, 0.8H, pip-H), 1.03-0.99 (m, 6H, J=6.6, $CH_{3OiBu}$). HPLC $t_R$=9.5 min.

Choosing the appropriate secondary amines (prepared in analogy to the method described for 103NLS56), following compounds were prepared using a similar procedure:

2-(4-Methoxyphenyl)-N-(4-methylbenzyl)-N-{1-[2-(2-oxo-imidazolidin-1-yl)ethyl]piperidin-4-yl}acetamide, hydrochloride (63ELH39-B)

LCMS m/z 465 [M+H]$^+$. $^1$H-NMR (CDCl$_3$, rotamers 0.6:0.4) δ 7.30-6.80 (m, 8H), 4.60-4.53 (m, 0.6H), 4.50 and 4.43 (2s, 2H), 3.78 (m, 4.2H), 3.51 (s, 1.2H), 3.46-3.24 (m, 6H), 2.92-2.79 (m, 2H), 2.46-2.40 (m, 2H), 2.35 and 2.29 (2s, 3H), 2.11-2.05 (m, 1.2H), 1.92-1.86 (m, 0.8H), 1.65-1.50 (m, 3.2H, partly covered by HDO signal), 1.31 (m, 0.8H).

N-(4-Fluorobenzyl)-2-(4-isopropoxyphenyl)-N-{1-[2-(2-oxo-imidazolidin-1-yl)ethyl]piperidin-4-yl}acetamide, hydrochloride (63ELH87)

N-(4-Fluorobenzyl)-2-(4-isopropoxyphenyl)-N-{1-[3-(3-methyl-2-oxo-2,3-dihydro-benzoimidazol-1-yl)propyl]piperidin-4-yl}acetamide; hydrochloride (103NLS39)

Prepared following the same method as described for 117NLS01 using N-(4-fluorobenzyl)-N-(piperidin-4-yl)-2-

(4-isoproxyphenyl)acetamide (229 mg, 0.59 mmol) and 1-(3-chloropropyl)-3-methyl-1,3-dihydrobenzimidazol-2-one as the alkylating agent.

Yield: 205 mg, 61%. $R_f$=0.29 (MeOH/CH$_2$Cl$_2$ 5:95). LCMS m/z 573 [M+H]$^+$. $^1$H-NMR (CDCl$_3$, rotamers 0.5:0.5) δ 7.18-6.78 (m, 12H, Ar—H), 4.59-4.43 (m, 3.5H, pip-H, OCH, benzyl-H), 3.88 (t, 2H, J=6.8, NCONCH$_2$), 3.74 (m, 1.5H, pip-H, benzyl-H), 3.49 (s, 1H, benzyl-H), 3.38 and 3.37 (2s, 3H, NCH$_3$), 2.93-2.79 (m, 2H, pip-H), 2.36-2.29 (m, 2H, NCH$_2$), 2.02-1.95 (m, 1H, pip-H), 1.90-1.46. (m, 6H, pip-H, NCH$_2$CH$_2$), 1.31-1.25 (m, 7H, pip-H, CH(CH$_3$)$_2$). HPLC $t_R$=8.0 min.

Choosing the appropriate secondary amines (prepared in analogy to the method described for 103NLS56) and alkylating agents, following compounds were prepared using a similar procedure:

N-{1-[2-(2,4-Dioxo-1,4-dihydro-2H-quinazolin-3-yl)ethyl]piperidin-4-yl}-2-(4-methoxyphenyl)-N-(4-methylbenzyl)acetamide, hydrochloride (63ELH29A).

2-(4-Methoxyphenyl)-N-(4-methylbenzyl)-N-{1-[3-(2-oxo-2,3-dihydrobenzoimidazol-1-yl)propyl]piperidin-4-yl}-acetamide, hydrochloride (50ELH89).

N-(4-Fluorobenzyl)-2-(4-isopropoxyphenyl)-N-{1-[4-(2-oxo-2,3-dihydrobenzoimidazol-1-yl)butyl]piperidin-4-yl}acetamide, hydrochloride (63ELH91).

N-{1-[2-(2,4-Dioxo-1,4-dihydro-2H-quinazolin-3-yl)ethyl]piperidin-4-yl}-N-(4-fluorobenzyl)-2-(4-isopropoxyphenyl)acetamide, hydrochloride (63ELH89).

4-(4-Fluorobenzylamino)-piperidine-1-carboxylic acid benzyl ester (118AF93-51)

A solution of 4-fluorobenzylamine (5.48 g, 43.8 mmol) in a mixture of methanol and acetic acid (5:1, 60 mL) was added dropwise to a solution of benzyl 4-oxo-1-piperidine carboxylate (10.2 g, 43.8 mmol) in methanol (150 mL) at rt. To this mixture sodium cyanoborohydride (5.50 g, 87.5 mmol) was slowly added. After 20 hours stirring at rt the reaction mixture was neutralized and the solvent was removed by evaporation under reduced pressure. The residue was partitioned between dichloromethane and water. The organic layer was dried over sodium sulphate, filtered and evaporated to dryness. Purification of the residue by silica gel column chromatography, eluting with 7% methanol in dichloromethane, afforded the desired compound (9.0 g, 60%).

$R_f$=0.56 (MeOH/CH$_2$Cl$_2$ 5:95). LCMS m/z 343 [M+H]$^+$. HPLC $t_R$=6.2 min.

N-(1-Benzyloxycarbonylpiperidin-4-yl)-N-(4-fluorobenzyl)-N'-(4-isopropoxybenzyl)carbamide (118AF97-120)

1,8-Bis(dimethylamino)-naphtalene (3.19 g, 14.9 mmol) was added to a solution of 4-(isopropoxy)phenyl acetic acid (2.89 g, 14.9 mmol) in dry tetrahydrofuran (18 mL) at rt under argon atmosphere. After 25 minutes stirring at rt diphenylphosphoryl azide (4.10 g, 14.9 mmol) was added dropwise and the mixture refluxed for 6 hours. It was allowed to cool to rt and then stored at −20° C. overnight to precipitate out the ammonium phosphate salt. A mixture of diethyl ether and ethyl acetate (1:1 v/v, 25 mL) was added to the cold reaction mixture. The precipitate was filtered from the reaction mixture and washed with diethyl ether: ethyl acetate (1:1 v/v 20 mL). The filtrate was evaporated to dryness giving 1-isocyanatomethyl-4-isopropoxybenzene as an oil (3.2 g), which was used in the next step without further purification.

Sodium carbonate (3.5 g, 25.3 mmol) was added to the solution of 4-(4-fluorobenzyl amino)-piperidine-1-carboxylic acid benzyl ester 118AF93-51 (5.7 g, 16.7 mmol) in dry tetrahydrofuran (20 mL). To this suspension a solution of 1-isocyanatomethyl-4-isopropoxybenzene (3.2 g, 16.7 mmol) in dry tetrahydrofuran (10 mL) was added under argon atmosphere. The reaction mixture was stirred overnight at rt. Afterwards the mixture was partitioned between dichloromethane and water. The organic layer was dried over sodium sulphate, filtered and evaporated to dryness. Purification of the residue by silica gel column chromatography, eluting with 8% methanol in dichloromethane afforded the desired compound (2.0 g, 22%).

$R_f$=0.36 (MeOH/CH$_2$Cl$_2$, 5:95). LCMS m/z 534 [M+H]$^+$. HPLC $t_R$=10.2 min.

N-(4-Fluorobenzyl)-N'-(4-isopropoxybenzyl)-N-piperidin-4-yl-carbamide, oxalate (118AF99-121)

The desired compound was obtained by hydrogenation of 118AF97-120 (2.0 g, 3.75 mmol) in absolute ethanol (100 mL) using palladium on carbon as a catalyst. The product was purified by column chromatography on silica gel eluting with stepwise gradient of 5-10% methanol in dichloromethane. Yield: 1.16 g, 77%.

$R_f$=0.10 (MeOH/CH$_2$Cl$_2$ 10:90). LCMS m/z 400 [M+H]$^+$. $^1$H NMR (CDCl$_3$) δ 7.19 (m, 2H, Ar—H), 7.01-6.69 (m, 4H, Ar—H), 6.76 (m, 2H, Ar—H), 4.51-4.40 (m, 3H, pip-H, OCH(CH$_3$), NH), 4.35 (s, 2H, benzyl-H), 4.28 (s, 1H, benzyl-H), 4.27 (s, 1H, benzyl-H), 3.14-3.07 (m, 2H, pip-H), 2.74-2.68 (m, 2H, pip-H), 2.10 (broad s, 1H, NH), 1.78-1.70 (m, 2H, pip-H), 1.58-1.48 (m, 2H, pip-H), 1.31 (d, 6H, J=6.0, OCH(CH$_3$)). HPLC $t_R$=5.9 min.

N-{1-[2-(1,3-Dioxolan-2-yl)ethyl]piperidin-4-yl}-N-(4-fluorobenzyl)-N'-(4-isopropoxy-benzyl)carbamide, oxalate (130AF10-147)

Potassium carbonate (0.21 g, 1.50 mmol) was added to a solution of 118AF99-121 (0.3 g, 0.75 mmol) in dry N,N-dimethylformamide (2 mL). The suspension was shaken for 30 minutes at 58° C. A solution of 2-(2-bromoethyl)-1,3-dioxolane (0.163 g, 0.90 mmol) in dry N,N-dimethylformamide (0.4 mL) was added dropwise to the warm suspension and the heating was continued overnight. The mixture was allowed to cool to rt, then filtered and partitioned between water and dichloromethane. The organic layer was washed with a aqueous solution of 4% magnesium sulphate and evaporated to dryness. Purification of the residue by silica gel column chromatography, eluting with 4% methanol in dichloromethane, afforded the desired compound (197 mg, 53%). The product was converted to its oxalate form as described above.

$R_f$=0.39 (MeOH/CH$_2$Cl$_2$ 4:94). LCMS m/z 500 [M+H]$^+$. $^1$H NMR (CDCl$_3$) δ 7.17 (m, 2H, Ar—H), 7.00-6.95 (m, 4H, Ar—H), 6.76 (m, 2H, Ar—H), 4.88 (t, 1H, J=4.8, dioxolane-H), 4.51-4.44 (m, 2H, NH, CH(CH$_3$)$_2$), 4.36-4.26 (m, 5H, benzyl-H, pip-H), 3.95-3.80 (m, 4H, dioxolane-H), 2.98-2.91 (m, 2H, pip-H), 2.48-2.43 (m, 2H, NCH$_2$), 2.10-2.01 (m, 2H, pip-H), 1.85-1.79 (m, 2H, NCH$_2$CH$_2$), 1.76-1.58 (m, 4H, pip-H), 1.30 (d, 6H, J=6.0, CH(CH$_3$)$_2$). HPLC $t_R$=6.9 min.

Choosing the appropriate secondary amines (prepared in analogy to the method described for 103NLS56), following compounds were prepared using the same procedure:

N-{1-[2-(1,3-Dioxolan-2-yl)ethyl]piperidin-4-yl}-2-(4-methoxyphenyl)-N-(4-methylbenzyl)acetamide, hydrochloride (63ELH29B).

N-{1-[2-(1,3-Dioxolan-2-yl)ethyl]piperidin-4-yl}-N-(4-fluorobenzyl)-2-(4-isobutoxyphenyl)acetamide, hydrochloride (74AKU06-2).

N-{1-[2-(1,3-Dioxolan-2-yl)ethyl]piperidin-4-yl}-2-(4-isopropoxyphenyl)-N-(4-methylbenzyl)acetamide, hydrochloride (76ELH07).

N-{1-[2-(1,3-Dioxolan-2-yl)ethyl]piperidin-4-yl}-N-(4-fluorobenzyl)-2-(4-propoxyphenyl)acetamide, tartrate (38PH50).

N-(4-Fluorobenzyl)-N'-(4-isopropoxybenzyl)-N-{1-[2-((S)-4-methyl-1,3-dioxolane-2-yl)ethyl]piperidin-4-yl}carbamide, oxalate (130AF12-148)

4 M HCl (0.5 mL) and water (0.5 mL) were added to a solution of 130AF10-147 (50 mg, 0.10 mmol) in 1.4-dioxane (1 mL). The mixture was stirred in a sealed flask for 10 minutes under microwave irradiation at 120° C. Afterwards the mixture was partitioned between dichloromethane and water. The organic layer was dried over sodium sulphate, filtered and evaporated to dryness. The residue was dissolved in 1.4-dioxane (1 mL) and a solution of (S)-(+)-propylene glycol (39 mg, 0.51 mmol) in 1.4-dioxane (0.5 mL) was added. After addition of HCl (4M in dioxane, 0.5 mL) the mixture was stirred in a sealed flask for 20 minutes under microwave irradiation at 120° C. The mixture was partitioned between saturated sodium bicarbonate solution and dichloromethane. The organic layer was evaporated to dryness. Purification of the residue by silica gel column chromatography, eluting with a stepwise gradient of 4-8% methanol in dichloromethane afforded the desired compound (2.1 mg, 4%). The product was converted to its oxalate form as described above.

$R_f$=0.36 (MeOH/CH$_2$Cl$_2$ 4:94). LCMS m/z 514 [M+H]$^+$. HPLC $t_R$=7.2 min.

N-(4-Fluorobenzyl)-N'-(4-isopropoxybenzyl)-N-[1-(3-morpholin-4-yl-propyl)piperidin-4-yl]carbamide, oxalate (130AF09-145)

A solution of 1-chloro-3-bromopropane in dry tetrahydrofuran (2 mL) was added to a cold suspension of morpholine (200 mg, 2.29 mmol) and sodium carbonate (0.63 g, 4.56 mmol) in dry tetrahydrofuran (8 mL) at 0° C. The mixture was stirred at 45° C. overnight. The mixture was allowed to cool to rt, filtered and evaporated to dryness. Purification of the residue by silica gel column chromatography, eluting with a mixture of ethyl acetate and n-heptane (70:30), afforded 3-chloro-1-morpholin-4-yl-propane (156 mg, 42%).

A solution of 3-chloro-1-morpholin-4-yl-propane (7.6 mg, 0.046 mmol) in dry N,N-dimethylformamide (0.10 mL) was added to a solution of 118AF99-121 (15 mg, 0.037 mmol) and caesium carbonate (40 mg, 0.123 mmol) in a mixture of dry N,N-dimethylformamide and acetonitrile (1:2, 0.30 mL). After addition of sodium iodide (7.0 mg, 0.047 mmol) the mixture was shaken overnight at 60° C. The mixture was allowed to cool to rt. Acetonitrile was removed by evaporation under reduced pressure and the residue was partitioned between dichloromethane (2 mL) and water (1 mL). The organic layer was evaporated to dryness. Purification of the residue by preparative reversed phase HPLC (C$_{18}$) afforded the desired compound (6.1 mg, 32%).

LCMS m/z 527 [M+H]$^+$. HPLC $t_R$=6.2 min.

Choosing the appropriate secondary amines (prepared in analogy to the method described for 103NLS56), following compounds were prepared using a simkilar procedure:

2-(4-Methoxyphenyl)-N-(4-methylbenzyl)-N-[1-(2-morpholin-4-ylethyl)piperidin-4-yl]acetamide, dihydrochloride (63ELH40-2).

2-(4-Methoxyphenyl)-N-(4-methylbenzyl)-N-[1-(3-morpholin-4-ylpropyl)piperidin-4-yl]acetamide, dihydrochloride (63ELH41-2).

N-(4-Fluorobenzyl)-2-(4-isobutoxyphenyl)-N-[1-(3-morpholin-4-ylpropyl)piperidin-4-yl]acetamide, dihydrochloride (74AKU07-2).

N-(4-Fluorobenzyl)-2-(4-isopropoxyphenyl)-N-[1-(3-morpholin-4-yl-propyl)piperidin-4-yl]acetamide, dihydrochloride (76ELH14-A).

N-(4-Fluorobenzyl)-N'-(4-isopropoxybenzyl)-N-[1-(3-piperidin-1-yl-propyl)piperidin-4-yl]carbamide, oxalate (130AF09-146)

The desired compound was synthesized from piperidine, 1-chloro-3-bromopropane and 118AF99-121 (15 mg, 0.037 mmol) using the same method as for preparation of 130AF09-145. Yield: 5.8 mg, 30%.

LCMS m/z 525 [M+H]$^+$. HPLC $t_R$=6.8 min.

N-(4-Fluorobenzyl)-N'-(4-isopropoxybenzyl)-N-[1-(3-((S)-4-isopropyl-2-oxazolidinon-1-yl-propyl)piperidin-4-yl]carbamide, tartrate (130AF14-152)

The desired compound was synthesized from (4S)-3-(3-chloropropyl)-4-isopropyloxazolidinon-2-one 103NLS94 (7.4 mg, 0.045 mmol) and 118AF99-121 (15 mg, 0.037 mmol) using the same method as for preparation of 130AF09-145. Yield: 3.3 mg, 16%.

LCMS m/z 569 [M+H]$^+$. HPLC $t_R$=8.2 min.

N-(4-Fluorobenzyl)-N'-(4-isopropoxybenzyl)-N-{1-[2-(2,5,5-trimethyl-1,3-dioxan-2-yl)ethyl]}piperidin-4-yl]carbamide, oxalate (130AF07-143)

The desired compound was synthesized from 2-bromo-1-(2,5,5-trimethyl-1,3-dioxan-2-yl)-ethane (10.7 mg, 0.045 mmol) and 118AF99-121 (15 mg, 0.037 mmol) using the same method as for preparation of 130AF09-145. Yield: 8.3 mg, 15%.

LCMS m/z 556 [M+H]+. HPLC tR=9.6 min.

N-{1-[3-(1,3-Dioxolan-2-yl)propyl]piperidin-4-yl}-N-(4-fluorobenzyl)-N'-(4-isopropoxybenzyl)carbamide, oxalate (130AF07-131)

The desired compound was synthesized from 3-chloro-1-(1,3-dioxolan-2-yl)-propane (6.79 mg, 0.045 mmol) and 118AF99-121 (15 mg, 0.037 mmol) using the same method as for preparation of 130AF09-145. Yield: 5.6 mg, 11%.

LCMS m/z 514 [M+H]+. HPLC tR=8.3 min.

N-[1-(2,2-Dimethyl-1,3-dioxan-5-yl)piperidin-4-yl]-N-(4-fluorobenzyl)-N'-(4-isopropoxybenzyl)carbamide, oxalate (130AF05-129)

A solution of 2,2-dimethyl-1,3-dioxan-5-one (9.75 mg, 0.075 mmol) in methanol (0.10 mL) was added to a solution of 118AF99-121 (15 mg, 0.037 mmol) in methanol (0.10 mL). The reaction mixture was stirred at rt after addition of acetic acid (60 μL of 1 M solution in methanol). After 2 h stirring a solution of sodium cyanoborohydride (5 mg, 0.079 mmol) in methanol (0.10 mL) was added and stirring was continued overnight at rt. The solvent was removed by evaporation under reduced pressure and the residue partitioned between 2 M aq. sodium hydroxide and dichloromethane. The layers were separated by filtration over PTFE filter. The organic layer was evaporated to dryness. Purification of the residue by preparative reversed phase HPLC ($C_{18}$) afforded the desired compound (2.3 mg, 12%).

LCMS m/z 514 [M+H]+. HPLC tR=9.0 min.

N-(4-Fluorobenzyl)-N'-(4-isopropoxybenzyl)-N-{[2-(1-methyl pyrrolidin-2-yl)ethyl]-piperidin-4-yl}carbamide, oxalate (130AF07-135)

The desired compound was synthesized from 2-(2-chloroethyl)-1-methylpyrrolidine hydrochloride (7.7 mg, 0.041 mmol) and 118AF99-121 (15 mg, 0.037 mmol) using the same method as for the preparation of 130AF09-145. Yield: 4.4 mg, 23%.

LCMS m/z 511 [M+H]+. HPLC tR=7.0 min.

N-[1-(2,2-Dimethyl-1,3-dioxan-5-yl)piperidin-4-yl]-N-(4-fluorobenzyl)-2-(4-isobutoxyphenyl)acetamide, oxalate (130AF22-105)

A solution of 2,2-dimethyl-1,3-dioxan-5-one (81 mg, 0.62 mmol) in methanol (10 mL) was added dropwise to a solution of 103NLS56 (179 mg, 0.45 mmol) in methanol (10 mL). The reaction mixture was stirred at rt after addition of acetic acid (200 µL). After 2 hours sodium cyanoborohydride (56 mg, 0.90 mmol) was slowly added and stirring was continued overnight at rt. The mixture was neutralized with few drops of 2 M aq sodium hydroxide. The solvent was removed by evaporation under reduced pressure and the residue partitioned between water and dichloromethane. The organic layer was dried over sodium sulphate, filtered and evaporated to dryness. Purification of the residue by silica gel column chromatography, eluting with 6% methanol in dichloromethane, afforded the desired compound (98 mg, 43%).

$R_f$=0.32 (MeOH/$CH_2Cl_2$, 6:94). LCMS m/z 513 [M+H]+. $^1$H NMR ($CDCl_3$, rotamers 0.4:0.6) δ 7.26-6.79 (m, 8H, Ar—H), 4.63-4.54 (m, 0.6H, pip-H), 4.50 & 4.43 (2s, 2H, benzyl-H), 3.91 & 3.88 (2d, 1H, J=5.6, dioxane-H), 3.79-3.67 (m, 6.2 H, dioxane-H, benzyl-H, pip-H, $CH_{2OiBu}$), 3.51 (s, 1.2H, benzyl-H), 2.98-2.88 (m, 2H, pip-H), 2.64-2.52 (m, 1H, dioxane-H), 2.38-2.28 (m, 1.2H, pip-H), 2.17-2.00 (m, 1.8H, $CH(CH_3)_2$, pip-H), 1.72-1.47 (m, 3.2H, pip-H), 1.43 (m, 0.8H, pip-H), 1.38-1.22 (m, 6H, dioxane-$CH_3$), 1.01 (m, 6H, $CH(CH_3)_2$). HPLC $t_R$=10.0 min.

N-[1-(1,3-Dioxan-5-yl)-piperidin-4-yl)-N-(4-fluorobenzyl)-2-(4-isobutoxyphenyl)acetamide, tartrate (130AF26-164)

3 M aq HCl (1 mL) and water (1 mL) were added to a solution of 130AF22-105 (98.2 mg, 0.19 mmol) in 1.4-dioxane (2 mL) and the mixture stirred in a sealed flask under microwave irradiation for 10 minutes at 120° C. The mixture was partitioned between water and dichloromethane and the organic layer dried over sodium sulphate, filtered and evaporated to dryness. The residue was dissolved in 1.4-dioxane (2 mL). To this solution a solution of formaldehyde (37% water solution, 101 mg, 1.16 mmol) in 1.4-dioxane (0.5 mL) was added. The reaction mixture was stirred in a sealed flask for 30 minutes under microwave irradiation at 120° C. Molecular sieves (4Å) were added to the reaction mixture at rt and removed after 24 hours. The mixture was heated for an additional 20 minutes at 120° C. under microwave irradiation and partitioned between dichloromethane and sodium bicarbonate. The organic layer was dried over sodium sulphate, filtered and evaporated to dryness. Purification of the residue by silica gel column chromatography, eluting with 6% methanol in dichloromethane, afforded the desired compound (17 mg, 18%). The product was converted to its tartrate form as described above.

$R_f$=0.30 (MeOH/$CH_2Cl_2$, 6:94). LCMS m/z 485 [M+H]+. $^1$H NMR ($CDCl_3$, rotamers 0.4:0.6) δ 7.21-6.80 (m, 8H, Ar—H), 4.88 (m, 1H, dioxane-H), 4.61-4.56 (m, 1.6H, dioxane-H, pip-H), 4.50 & 4.43 (2s, 2H, benzyl-H), 4.12-4.06 (m, 2H, dioxane-H) 3.85-3.60 (m, 5.2 H, dioxane-H, benzyl-H, pip-H, $CH_{2OiBu}$), 3.51 (s, 1.2H, benzyl-H), 2.94-2.86 (m, 2H, pip-H), 2.59-2.48 (m, 1H, dioxane-H), 2.37-2.28 (m, 1.2H, pip-H), 2.17-2.01 (m, 1.8H, $CH(CH_3)_2$, pip-H), 1.68-1.46 (m, 3.2H, pip-H), 1.46-1.30 (m, 0.8H, pip-H), 1.02 (m, 6H, $CH(CH_3)_2$). HPLC $t_R$=9.5 min.

N-[1-(2,2-Dimethyl-1,3-dioxan-5-yl)piperidin-4-yl]-N-(4-fluorobenzyl)-2-(4-fluorophenyl)acetamide, tartrate (130AF35-168)

The desired compound was synthesized from 2,2-dimethyl-1,3-dioxan-5-one (59 mg, 0.45 mmol) and N-(4-fluorobenzyl)-2-(4-fluorophenyl)-N-piperidin-4-yl-acetamide (83 mg, 0.24 mmol) using the same method as for preparation of 130AF22-105. The starting material N-(4-fluorobenzyl)-2-(4-fluorophenyl)-N-piperidin-4-yl-acetamide was prepared in the same way as 103NLS56.

$R_f$=0.26 (MeOH/$CH_2Cl_2$, 5:95). LCMS m/z 459 [M+H]+. $^1$H NMR ($CDCl_3$, rotamers 0.4:0.6) δ 7.28-6.91 (m, 8H, Ar—H), 4.63-4.52 (m, 0.6H, pip-H), 4.51 & 4.46 (2s, 2H, benzyl-H), 3.92-3.88 (m, 2H, dioxane-H), 3.82-3.69 (m, 3.2 H, dioxane-H, benzyl-H, pip-H), 3.54 (s, 1.2H, benzyl-H), 2.99-2.90 (m, 2H, pip-H), 2.62-2.51 (m, 1H, dioxane-H), 2.39-2.28 (m, 1.2H, pip-H), 2.18-2.10 (m, 0.8H, pip-H), 1.72-1.50 (m, 3.2H, pip-H), 1.42-1.31 (m, 6.8H, pip-H, dioxane-$CH_3$). HPLC $t_R$=7.9 min.

N-{1-[2-(1,3-Dioxan-4-yl)ethyl]piperidin-4-yl}-N-(4-fluorobenzyl)-2-(4-fluorophenyl)acetamide, tartrate (130AF41-171)

The starting material N-(4-fluorobenzyl)-2-(4-fluorophenyl)-N-piperidin-4-yl-acetamide was prepared in the same way as 103NLS56.

Potassium carbonate (64 mg, 0.46 mmol) was added to a solution of N-(4-fluorobenzyl)-2-(4-fluorophenyl)-N-piperidin-4-yl-acetamide (79.4 mg, 0.23 mmol) in dry N,N-dimethylformamide (3 mL). To this suspension a solution of 4-[2-(tosyloxy)ethyl]-1,3-dioxane 128NLS46B (99 mg, 0.35 mmol) in dry N,N-dimethylformamide (1 mL) was added dropwise at rt. The reaction mixture was stirred overnight at 60° C. and it was partitioned between dichloromethane and water. The organic layer was dried over sodium sulphate, filtered and evaporated to dryness. Purification of the residue by silica gel column chromatography, eluting with stepwise gradient of 2-5% methanol in dichloromethane, afforded the desired product (71 mg, 67%). The product was converted to its tartrate form as described above.

$R_f$=0.41 (MeOH/$CH_2Cl_2$, 6:96). LCMS m/z 459 [M+H]+. $^1$H NMR ($CDCl_3$, rotamers 0.4:0.6) δ 7.28-6.90 (m, 8H, Ar—H), 4.99 (m, 1H, dioxane-H), 4.77-4.64 (m, 1.6H, pip-H, dioxane-H), 4.52 (s, 2H, benzyl-H), 3.80-3.56 (m, 4.4H, dioxane-H, benzyl-H, pip-H), 3.21-3.08 (m, 1.2H, pip-H), 2.96-2.88 (m, 0.8H, pip-H), 2.75-2.56 (m, 1.2H, $NCH_2$), 2.52-2.24 (m, 2H, pip-H, $NCH_2$), 2.04-1.30 (m, 9.8H, pip-H, $NCH_2CH_2$, dioxane-H). HPLC $t_R$=6.4 min.

N-{1-[2-(1,3-Dioxan-4-yl)ethyl]piperidin-4-yl}-N-(4-fluorobenzyl)-2-(4-trifluoromethoxyphenyl)acetamide, tartrate (130AF80-186)

Triethylamine (125 µL, 0.89 mmol) was added to a solution of N-{1-[2-(1,3-dioxan-4-yl)ethyl]piperidin-4-yl}-N-(4-fluorobenzyl)amine 128NLS52 (96 mg, 0.30 mmol) in dry dichloromethane (5 mL) at rt. The solution was cooled to −10° C. and a solution of (4-trifluoromethoxyphenyl)acetyl chloride (71 mg, 0.30 mmol) in dry dichloromethane (1 mL) was added dropwise. The reaction mixture was stirred overnight at rt. The solvent was removed by evaporation under reduced pressure. The residue was suspended in tetrahydrofuran and filtered. The filtrate was evaporated to dryness and the residue was purified by silica gel column chromatography, eluting with 4% methanol in dichloromethane, to give the desired compound (46 mg, 30%). The compound was converted to its tartrate form as described above.

$R_f$=0.33 (MeOH/CH$_2$Cl$_2$, 6:94). LCMS m/z 459 [M+H]$^+$. $^1$H NMR (CDCl$_3$, rotamers 0.4:0.6) δ 7.34-6.91 (m, 8H, Ar—H), 5.01 (d, 1H, J=6.0, dioxane-H), 4.66-4.54 (m, 1.6H, pip-H, dioxane-H), 4.52 & 4.49 (2s, 2H, benzyl-H), 4.09-4.05 (m, 1H, dioxane-H), 3.83 (s, 0.8H, benzyl-H), 3.72-3.56 (m, 3.6 H, dioxane-H, benzyl-H, pip-H), 2.94-2.86 (m, 2H, pip-H), 2.50-2.32 (m, 2H, NCH$_2$), 2.11-2.00 (m, 1.2H, pip-H), 1.90-1.52 (m, 8.8H, pip-H, NCH$_2$CH$_2$, dioxane-H). HPLC $t_R$=7.6 min.

N-{1-[2-(1,3-Dioxan-4-yl)ethyl]piperidin-4-yl}-N-(4-fluorobenzyl)-2-(4-propoxyphenyl)acetamide, tartrate (130AF71-184)

Triethylamine (163 µL, 1.17 mmol) was added to a solution of N-{1-[2-(1,3-dioxan-4-yl)ethyl]piperidin-4-yl}-N-(4-fluorobenzyl)amine 128NLS52 (126 mg, 0.39 mmol) in dry dichloromethane (5 mL) at rt. The solution was cooled to −15° C. and a solution of (4-propoxyphenyl)acetyl chloride (92 mg, 0.43 mmol) in dry dichloromethane (2 mL) was added dropwise. The reaction mixture was stirred for 2 hours at rt. The solvent was removed by evaporation under reduced pressure. The residue was suspended in tetrahydrofuran and filtered. The filtrate was evaporated to dryness and the residue was purified by silica gel column chromatography, eluting with a stepwise gradient of 0-4% methanol in dichloromethane, to give the desired compound (66 mg, 34%). The product was converted to its tartrate form as described above.

$R_f$=0.16 (MeOH/CH$_2$Cl$_2$, 4:96). LCMS m/z 499 [M+H]$^+$. $^1$H NMR (CDCl$_3$, rotamers 0.4:0.6) δ 7.21-6.78 (m, 8H, Ar—H), 5.00 (m, 1H, dioxane-H), 4.66-4.54 (m, 1.6H, pip-H, dioxane-H), 4.50 & 4.44 (2s, 2H, benzyl-H), 4.10-4.03 (m, 1H, dioxane-H), 3.92-3.87 (m, 2H, OCH$_{2OPr}$), 3.78-3.50 (m, 4.4 H, dioxane-H, benzyl-H, pip-H), 2.92-2.82 (m, 2H, pip-H), 2.50-2.29 (m, 2H, NCH$_2$), 2.09-1.98 (m, 1.2H, pip-H), 1.88-1.27 (m, 10.8H, pip-H, NCH$_2$CH$_2$, dioxane-H, CH$_{2OPr}$), 1.05-099 (m, 3H, CH$_3$OPr). HPLC $t_R$=7.6 min.

N-(4-Fluorobenzyl)-2-(4-isobutoxyphenyl)-N-[1-(tetrahydropyran-4-yl)piperidin-4-yl]acetamide, tartrate (130AF33-166)

A solution of tetrahydro-4H-pyran-4-one (43 mg, 0.42 mmol) in methanol (1 mL) was added to a solution of 103NLS56 (57 mg, 0.14 mmol) in methanol (2 mL). After addition of acetic acid (100 µL) the reaction mixture was stirred for 15 minutes in a sealed flask under microwave irradiation at 100° C. Afterwards sodium cyanoborohydride (26 mg, 0.42 mmol) was added to the mixture and stirring was continued for additional 60 min under microwave irradiation at 80° C. The mixture was passed over an acidic ion-exchange SPE cartridge. Further purification of the product by silica gel column chromatography, eluting with a stepwise gradient of 2-5% methanol in dichloromethane, afforded the desired compound (19.2 mg, 28%). The compound was converted to its tartrate form as described above.

$R_f$=0.18 (MeOH/CH$_2$Cl$_2$, 5:95). LCMS m/z 483 [M+H]$^+$. $^1$H NMR (CDCl$_3$, rotamers 0.4:0.6) δ 7.21-6.80 (m, 8H, Ar—H), 4.64-4.56 (m, 0.6H, pip-H), 4.51& 4.45 (2s, 2H, benzyl-H), 4.02-3.96 (m, 2H, THP—H), 3.77-3.68 (m, 3.2H, benzyl-H, CH$_{2OiBu}$, pip-H), 3.51 (s, 1.2H, benzyl-H), 3.30 (t, 2H, J=12.0, THP—H), 2.98-2.88 (m, 2H, pip-H), 2.46-2.34 (m, 1H, THP—H), 2.28-2.19 (m, 1.2H, pip-H), 2.10-1.99 (m, 1.8H, CH$_{OiBu}$, pip-H), 1.73-1.47 (m, 7.2H, pip-H, THP—H), 1.39-1.33 (m, 0.8H, pip-H), 1.01 (m, 6H, CH$_{3OiBu}$). HPLC $t_R$=8.0 min.

N-(4-Fluorobenzyl)-2-(4-isobutoxyphenyl)-N-[1-(tetrahydropyran-4-ylmethyl)piperidin-4-yl]acetamide, tartrate (130AF82-187)

The title compound was synthesized from N-(4-fluorobenzyl)-2-(4-isobutoxyphenyl)-N-piperidin-4-yl-acetamide103NLS56 (110 mg, 0.27 mmol) and tetrahydro-2H-pyran-4-yl carbaldehyde (63 mg, 0.55 mmol) using the same method as for preparation of 130AF33-166. Yield: 18 mg, 13%.

$R_f$=0.30 (MeOH/CH$_2$Cl$_2$, 5:95). LCMS m/z 497 [M+H]$^+$. HPLC $t_R$=8.4 min.

N-(4-Fluorobenzyl)-2-(4-isobutoxyphenyl)-N-{1-[2-(tetrahydropyran-4-yl)ethyl]piperidin-4-yl]acetamide, tartrate (130AF83-188)

The title compound was synthesized from N-(4-fluorobenzyl)-2-(4-isobutoxyphenyl)-N-piperidin-4-yl-acetamide103NLS56 (110 mg, 0.27 mmol) and tetrahydro-2H-pyran-4-yl acetalaldehyde (70.5 mg, 0.55 mmol) using the same method as for preparation of 130AF33-166. Yield: 40 mg, 29%.

$R_f$=0.30 (MeOH/CH$_2$Cl$_2$, 5:95). LCMS m/z 511 [M+H]$^+$. $^1$H NMR (CDCl$_3$, rotamers 0.4:0.6) δ 7.21-6.80 (m, 8H, Ar—H), 4.65-4.55 (m, 0.6H, pip-H), 4.51& 4.44 (2s, 2H, benzyl-H), 3.95-3.89 (m, 2H, THP—H), 3.78-3.66 (m, 3.2H, benzyl-H, CH$_{2OiBu}$, Pip-H), 3.51 (s, 1.2H, benzyl-H), 3.34 (t, 2H, J=12.0, THP—H), 2.92-2.82 (m, 2H, pip-H), 2.34-2.26 (m, 2H, NCH$_2$CH$_2$), 2.11-1.96 (m, 2.2H, pip-H, CH$_{OiBu}$), 1.84-1.20 (m, 11.8H, pip-H, THP—H, CH$_2$CH$_2$N), 1.02 (m, 6H, CH$_{3OiBu}$). HPLC $t_R$=8.2 min.

N-(4-Fluorobenzyl)-2-(4-fluorophenyl)-N-[1-(tetrahydropyran-4-yl)piperidin-4-yl]acetamide, tartrate (130AF37-169)

The desired compound was synthesized from tetrahydro-4H-pyran-4-one and N-(4-fluorobenzyl)-2-(4-fluorophenyl)-N-piperidin-4-yl-acetamide using the same method as for preparation of 130AF33-166. The starting material N-(4-fluorobenzyl)-2-(4-fluorophenyl)-N-piperidin-4-yl-acetamide was prepared in the same way as 103NLS56.

$R_f$=0.29 (MeOH7CH$_2$Cl$_2$, 5:95). LCMS m/z 429 [M+H]$^+$. $^1$H NMR (CDCl$_3$, rotamers 0.4:0.6) δ 7.29-6.91 (m, 8H, Ar—H), 4.64-4.55 (m, 0.6H, pip-H), 4.52 & 4.48 (2s, 2H, benzyl-H), 4.02-3.95 (m, 2H, THP—H), 3.80 (s, 0.8H, benzyl-H), 3.75-3.64 (m, 0.4H, benzyl-H), 3.54 (s, 1.2H, benzyl-H), 3.34 (t, 2H, J=12.0, THP—H), 2.99-2.90 (m, 2H, pip-H), 2.48-2.36 (m, 1H, THP—H), 2.26-2.20 (m, 1.2H, pip-H), 2.08-2.00 (m, 0.8H, pip-H), 1.76-1.47 (m, 7.2H, pip-H, THP—H), 1.41-1.34 (m, 0.8H, pip-H). HPLC $t_R$=5.6 min.

N-[1-((S)-3,5-Dihydroxypentyl)piperidine-4-yl]-N-(4-fluorobenzyl)-2-(4-isobutoxyphenyl)acetamide, tartrate (130AF65-182)

The compound (R)-5-[(4-methylbenzenesulfonyl)oxy]pentane-1,3-diol was synthesized according to Moune et al (*J. Org. Chem.*, 1997, 62, 3332-3339). Potassium carbonate (83 mg, 0.60 mmol) was added to a solution of 103NLS56 (94 mg, 0.24 mmol) in dry N,N-dimethylformamide (3 mL). To this suspension a solution of (R)-5-[(4-methyl-benzenesulfonyl)oxy]pentane-1,3-diol (82 mg, 0.28 mmol) in dry N,N-dimethylformamide (1 mL) was added, followed by addition of sodium iodide (43 mg, 0.29 mmol). The reaction mixture was stirred overnight at 60° C. It was allowed to cool to rt, filtered and evaporated to dryness. The residue was partitioned between dichloromethane and 2M aq sodium hydroxide. The organic layer was dried over sodium sulphate, filtered and evaporated to dryness. Purification of the residue by silica gel column chromatography, eluting with a stepwise gradient of 6-10% methanol in dichloromethane, afforded the desired compound (35 mg, 29%), which was converted to its tartrate form as described above.

$R_f$=0.48 (MeOH/CH$_2$Cl$_2$, 10:90). LCMS m/z 501 [M+H]$^+$. HPLC $t_R$=7.4 min.

N-{1-[2-((4S)-1,3-Dioxane-4-yl)ethyl]piperidine-4-yl}-N-(4-fluorobenzyl)-2-(4-isobutoxyphenyl)acetamide, tartrate (130AF67-183)

Paraformaldehyde (9 mg, 0.28 mmol) and hydrochloric acid (4M in 1.4-dioxane, 0.5 mL) were added to a solution of tartaric acid salt of 130AF65-182 (37 mg, 0.056 mmol) in 1.4-dioxane. The reaction mixture was stirred for 2 hours in a sealed flask under microwave irradiation at 120° C. and partitioned between dichloromethane and sodium bicarbonate. The organic layer was washed with brine, dried over sodium sulphate, filtered and evaporated to dryness. Purification of the residue by acidic ion-exchange SPE cartridge afforded the desired compound (9.0 mg, 31%), which was converted to its tartrate form as described above. The enantiomeric excess (ee) was determined to be 94% using chiral HPLC analysis (Chiralpak AD column, 4.6×250 mm; heptane/I—PrOH 50:50, 0.3% DEA; 0.5 mL/min; $t_R$ 20.5 min).

$R_f$=0.41 (MeOH/CH$_2$Cl$_2$, 8:92). LCMS m/z 513 [M+H]$^+$. $^1$H NMR (CDCl$_3$, rotamers 0.4:0.6) δ 7.21-6.80 (m, 8H, Ar—H), 5.00 (m, 1H, dioxane-H), 4.68-4.54 (m, 1.6H, pip-H, dioxane-H), 4.51 & 4.45 (2s, 2H, benzyl-H), 4.06 (m, 1H, dioxane-H), 3.77-3.48 (m, 6.4H, dioxane-H, benzyl-H, CH$_{2OiBu}$, pip-H), 2.98-2.79 (m, 2H, pip-H), 2.50-2.58 (m, 2H, NCH$_2$), 2.14-1.99 (m, 2.2H, CH$_{OiBu}$, pip-H), 1.90-1.25 (m, 8.8H, pip-H, NCH$_2$CH$_2$, dioxane-H), 1.02 (m, 6H, CH$_{3OiBu}$). HPLC $t_R$=8.7 min.

N-{1-[2-(1,3-Dioxan-2-yl)ethyl]piperidin-4-yl}-N-(4-fluorobenzyl) amine (118AF52-95)

Sodium carbonate (17.4 g, 125.9 mmol) was added to a solution of 4-piperidone monohydrate hydrochloride (6.45 g, 42.0 mmol) in acetonitrile (200 mL). After 30 minutes stirring at rt a solution of 2-(2-bromoethyl)-1,3-dioxane (8.45 g, 43.3 mmol) in acetonitrile (50 mL) was added dropwise to the reaction mixture and stirring was continued overnight at rt and at reflux for an additional 2 hours. The solvent was removed by evaporation under reduced pressure and the residue was partitioned between water and dichloromethane. The organic layer was dried over sodium sulphate, filtered and evaporated to dryness. Purification of the residue by silica gel column chromatography, eluting with 7% methanol in dichloromethane, afforded 1-[2-(1,3-dioxan-2-yl)ethyl]piperidin-4-one (6.19 g, 69%).

A solution of 1-[2-(1,3-dioxan-2-yl)ethyl]piperidin-4-one (6.19 g, 29 mmol) in methanol (80 mL) was added dropwise to a solution of 4-fluorobenzylamine (3.9 mL, 34 mmol) in methanol (100 mL) under argon atmosphere at rt. After 30 minutes stirring at rt the reaction mixture was acidified (pH=5) with acetic acid and cooled to 0° C. Sodium cyanoborohydride (2.15 g, 40 mmol) was added slowly to the cold mixture and stirring was continued at rt overnight. The reaction mixture was basified with 2M NaOH and concentrated in vacuo. The residue was partitioned between ethyl acetate and water. The organic layer was dried over sodium sulphate, filtered and evaporated to dryness. The residue was dissolved in abs. ethanol (57 mL). A solution of maleic acid (3.31 g, 28.5 mmol) in abs. ethanol (60 mL) was added to this solution resulting in precipitate formation. The precipitate was collected by filtration and converted to the free base by a basic extraction. Yield: 8.5 g, 91%.

$R_f$=0.29 (MeOH/CH$_2$Cl$_2$, 7:93). LCMS m/z 323 [M+H]$^+$. $^1$H NMR (CDCl$_3$) δ 7.25 (m, 2H, Ar—H), 6.95 (m, 2H, Ar—H), 4.54 (t, 1H, J=5.6, dioxane-H), 4.07-4.02 (m, 2H, dioxane-H), 3.73-3.67 (m, 4H, dioxane-H, benzyl-H), 2.85-2.79 (m, 2H, pip-H), 2.49-2.37 (m, 3H, NCH$_2$, pip-H), 2.05-1.72 (m, 7H, pip-H, NCH$_2$CH$_2$, dioxane-H), 1.44-1.25 (m, 4H, dioxane-H, pip-H, NH). HPLC $t_R$=1.4 min.

2-(4-Benzyloxyphenyl)-N-{1-[2-(1,3-dioxan-2-yl)ethyl]piperidin-4-yl}-N-(4-fluorobenzyl)acetamide, tartrate (118AF66-102)

A solution of triethylamine (0.89 mL, 6.38 mmol) and 118AF52-95 (0.80 g, 2.48 mmol) in dry THF (10 mL) was cooled to 0° C. A solution of 4-benzyloxyphenylacetyl chloride (0.72 g, 2.76 mmol) was added dropwise to the cold reaction mixture and stirring was continued at rt for 2 h. The reaction mixture was filtered and the filtrate evaporated to dryness. Purification of the residue by silica gel column chromatography, eluting with a stepwise gradient of 0-6% methanol in dichloromethane afforded the desired compound (0.53 g, 39%), which was converted to its tartrate form as described above.

$R_f$=0.27 (MeOH/CH$_2$Cl$_2$, 7:93). LCMS m/z 547 [M+H]$^+$. $^1$NMR (CDCl$_3$, rotamers 0.4:0.6) δ 7.46-6.86 (m, 13H, Ar—H), 5.08-5.02 (m, 2H, PhCH$_2$O), 4.64-4.42 (m, 3.6H, pip-H, benzyl-H, dioxane-H), 4.11-4.02 (m, 2H, dioxane-H), 3.79-3.67 (m, 3.2H, dioxane-H, benzyl-H, pip-H), 3.50 (s, 1.2H, benzyl-H), 2.94-2.80 (m, 2H, pip-H), 2.46-2.34 (m, 2H, NCH$_2$), 2.12-1.98 (m, 2.2H, dioxane-H, pip-H), 1.87-1.50 (m, 6H, pip-H, NCH$_2$CH$_2$), 1.36-1.24 (m, 1.8H, pip-H, dioxane-H). HPLC $t_R$=8.9 min.

N-{1-[2-(1,3-Dioxan-2-yl)ethyl]piperidin-4-yl}-N-(4-fluorobenzyl)-2-(4-hydroxyphenyl)-acetamide, tartrate (118AF67-103)

The desired compound was afforded by hydrogenation of 118AF66-102 (0.50 g, 0.92 mmol) in absolute ethanol (200 mL) using palladium on carbon as a catalyst. The product was purified by column chromatography on silica gel eluting with a stepwise gradient of 3-6% methanol in dichloromethane.

The desired compound (0.22 g, 53%) was converted to its tartrate form as described above.

R$_f$=0.30 (MeOH/CH$_2$Cl$_2$, 6:94). LCMS m/z 457 [M+H]$^+$. $^1$NMR (CDCl$_3$, rotamers 0.4:0.6) δ 7.13-6.86 (m, 6H, Ar—H), 6.72-6.64 (m, 2H, Ar—H), 4.66-4.57 (m, 0.6H, pip-H), 4.54 (m, 1H, dioxane-H), 4.48 & 4.37 (2s, 2H, benzyl-H), 4.08-4.01 (m, 2H, dioxane-H), 3.80-3.66 (m, 3.2H, dioxane-H, benzyl-H, pip-H), 3.47 (m, 1.2H, benzyl-H), 2.94-2.82 (m, 2H, pip-H), 2.47-2.39 (m, 2H, NCH$_2$), 2.10-1.97 (m, 2.2H, dioxane-H, pip-H), 1.88-1.53 (m, 6H, pip-H, NCH$_2$CH$_2$), 1.34-1.25 (m, 1.8H, pip-H, dioxane-H). HPLC t$_R$=3.0 min.

I. N-{1-[2-(1,3-Dioxan-2-yl)ethyl]piperidin-4-yl}-N-(4-fluorobenzyl)-2-(4-methoxyphenyl)-acetamide, tartrate (118AF60-961)

A solution of triethylamine (0.57 mL, 4.09 mmol) and 118AF52-95 (328 mg, 1.02 mmol) in dry THF (5 mL) was cooled to 0° C. A solution of 4-methoxyphenylacetyl chloride (376 mg, 2.04 mmol) was added dropwise to the cold reaction mixture and stirring was continued for 20 h at rt. The reaction mixture was partitioned between 2M NaOH and water. The organic layer was dried over sodium sulphate, filtered and evaporated to dryness. The residue was purified by silica gel column chromatography, eluting with a stepwise gradient of 0-6% methanol in dichloromethane. Final purification of the product by acidic ion-exchange SPE cartridge afforded the desired compound (153 mg, 33%), which was converted to its tartrate form as described above.

R$_f$=0.40 (MeOH/CH$_2$Cl$_2$, 4:96). LCMS m/z 471 [M+H]$^+$. $^1$NMR (CDCl$_3$, rotamers 0.4:0.6) δ 7.24-6.79 (m, 8H, Ar—H), 4.63-4.54 (m, 0.6H, pip-H), 4.52 (t, 1H, J=5.2, dioxane-H), 4.49 & 4.44 (2s, 2H, benzyl-H), 4.09-4.01 (m, 2H, dioxane-H), 3.79-3.68 (m, 6.2H, dioxane-H, benzyl-H, pip-H, OCH$_3$), 3.50 (m, 1.2H, benzyl-H), 2.91-2.80 (m, 2H, pip-H), 2.43-2.36 (m, 2H, NCH$_2$), 2.10-1.98 (m, 2.2H, dioxane-H, pip-H), 1.86-1.51 (m, 6H, pip-H, NCH$_2$CH$_2$), 1.34-1.26 (m, 1.8H, pip-H, dioxane-H). HPLC t$_R$=7.0 min.

N-{1-[2-(1,3-Dioxan-2-yl)ethyl]piperidin-4-yl}-N-(4-fluorobenzyl)-2-(4-isopropylphenyl)-acetamide, tartrate (118AF63-100)

The desired compound was synthesized from 118AF52-95 (400 mg, 1.24 mmol) and 4-isopropylphenylacetyl chloride (340 mg, 1.73 mmol) using the same method as for preparation of 118AF66-102. Further purification by acidic ion-exchange SPE cartridge was performed. Yield: 273 mg, 46%.

R$_f$=0.34 (MeOH/CH$_2$Cl$_2$, 7:93). LCMS m/z 483 [M+H]$^+$. $^1$NMR (CDCl$_3$, rotamers 0.4:0.6) δ 7.22-6.89 (m, 8H, Ar—H), 4.64-4.43 (m, 3.6H, pip-H, dioxane-H, benzyl-H), 4.09-4.02 (m, 2H, dioxane-H), 3.79 (s, 0.8H, benzyl-H), 3.76-3.66 (m, 2.4H, dioxane-H, pip-H), 3.54 (m, 1.2H, benzyl-H), 2.92-2.79 (m, 3H, pip-H, CH(CH$_3$)$_2$), 2.41-2.35 (m, 2H, NCH$_2$), 2.12-1.98 (m, 2.2H, dioxane-H, pip-H), 1.85-1.49 (m, 6H, pip-H, NCH$_2$CH$_2$), 1.34-1.19 (m, 7.8H, pip-H, dioxane-H, CH(CH$_3$)$_2$). HPLC t$_R$=8.6 min.

N-{1-[2-(1,3-Dioxan-2-yl)ethyl]piperidin-4-yl}-N-(4-fluorobenzyl)-2-(4-trifluoromethoxy-phenyl)acetamide, tartrate (118AF58-98)

The desired compound was synthesized from 118AF52-95 (328 mg, 1.02 mmol) and 4-trifluoromethoxyphenylacetyl chloride (345 mg, 1.44 mmol) using the same method as for preparation of 118AF66-102. Yield: 267 mg, 49%.

R$_f$=0.31 (MeOH/CH$_2$Cl$_2$, 4:96). LCMS m/z 525 [M+H]$^+$. $^1$NMR (CDCl$_3$, rotamers 0.4:0.6) δ 7.30-6.90 (m, 8H, Ar—H), 4.63-4.48 (m, 3.6H, pip-H, dioxane-H, benzyl-H), 4.05 (m, 2H, dioxane-H), 3.82 (s, 0.8H, benzyl-H), 3.76-3.62 (m, 2.4H, dioxane-H, pip-H), 3.55 (m, 1.2H, benzyl-H), 2.92-2.84 (m, 2H, pip-H), 2.43-2.36 (m, 2H, NCH$_2$), 2.10-1.96 (m, 2.2H, dioxane-H, pip-H), 1.88-1.79 (m, 0.8H, pip-H), 1.76-1.52 (m, 5.2H, pip-H, NCH$_2$CH$_2$), 1.38-1.26 (m, 1.8H, pip-H, dioxane-H). HPLC t$_R$=8.4 min.

II. N-{1-[2-(1,3-Dioxan-2-yl)ethyl]piperidin-4-yl}-N-(4-fluorobenzyl)-2-(4-ethoxyphenyl)-acetamide, oxalate (118AF68-104)

The desired compound was synthesized from 118AF52-95 (400 mg, 1.24 mmol) and 4-ethoxyphenylacetyl chloride (300 mg, 1.51 mmol) using the same method as for preparation of 118AF66-102. Further purification by acidic ion-exchange SPE cartridge was performed. Yield: 0.15 g, 25%.

R$_f$=0.26 (MeOH/CH$_2$Cl$_2$, 6:94). LCMS m/z 485 [M+H]$^+$. $^1$NMR (CDCl$_3$, rotamers 0.4:0.6) δ 7.20-6.79 (m, 8H, Ar—H), 4.64-4.54 (m, 0.6H, pip-H), 4.52 (t, 1H, J=5.2, dioxane-H), 4.49 & 4.43 (2s, 2H, benzyl-H), 4.07-3.97 (m, 4H, dioxane-H, OCH$_2$), 3.76-3.66 (m, 3.2H, dioxane-H, pip-H, benzyl-H), 3.49 (s, 1.2H, benzyl-H), 2.91-2.80 (m, 2H, pip-H), 2.42-2.32 (m, 2H, NCH$_2$), 2.10-1.97 (m, 2.2H, dioxane-H, pip-H), 1.86-1.48 (m, 6H, pip-H, NCH$_2$CH$_2$), 1.42-1.36 (m, 3H, CH$_3$), 1.34-1.24 (m, 1.8H, pip-H, dioxane-H). HPLC t$_R$=7.6 min.

III. N-{1-[2-(1,3-Dioxan-2-yl)ethyl]piperidin-4-yl}-N-(4-fluorobenzyl)-2-(4-isopropoxyphenyl)-acetamide, oxalate (118AF73-107)

The desired compound was synthesized from 118AF52-95 (400 mg, 1.24 mmol) and 4-isopropoxyphenylacetyl chloride (340 mg, 1.60 mmol) using the same method as for preparation of 118AF66-102. Further purification by acidic ion-exchange SPE cartridge was performed. Yield: 91 mg, 15%.

R$_f$=0.58 (MeOH/CH$_2$Cl$_2$, 8:92). LCMS m/z 499 [M+H]$^+$. $^1$NMR (CDCl$_3$, rotamers 0.4:0.6) δ 7.19-6.78 (m, 8H, Ar—H), 4.64-4.42 (m, 4.6H, pip-H, dioxane-H, benzyl-H, CH$_{OiPr}$), 4.07 (m, 2H, dioxane-H), 3.76-3.68 (m, 3.2H, dioxane-H, pip-H, benzyl-H), 3.49 (s, 1.2H, benzyl-H), 2.91-2.80 (m, 2H, pip-H), 2.42-2.35 (m, 2H, NCH$_2$), 2.10-1.99 (m, 2.2H, dioxane-H, pip-H), 1.85-1.51 (m, 6H, pip-H, NCH$_2$CH$_2$), 1.31 (m, 7.8H, OCH(CH$_3$)$_2$, pip-H, dioxane-H). HPLC t$_R$=8.1 min.

IV. N-{1-[2-(1,3-Dioxan-2-yl)ethyl]piperidin-4-yl}-N-(4-fluorobenzyl)-2-phenylacetamide, oxalate (118AF77-109)

The desired compound was synthesized from 118AF52-95 (300 mg, 0.93 mmol) and phenylacetyl chloride (197 mg, 1.27 mmol) using the same method as for preparation of 118AF66-102. Further purification by acidic ion-exchange SPE cartridge was performed. Yield: 68 mg, 17%.

R$_f$=0.28 (MeOH/CH$_2$Cl$_2$, 5:95). LCMS m/z 441 [M+H]$^+$. $^1$NMR (CDCl$_3$, rotamers 0.4:0.6) δ 7.33-6.89 (m, 9H, Ar—H), 4.65-4.44 (m, 3.6H, pip-H, dioxane-H, benzyl-H), 4.09-4.03 (m, 2H, dioxane-H), 3.84 (s, 0.8H, benzyl-H), 3.76-3.67 (m, 2.4H, dioxane-H, pip-H), 3.57 (s, 1.2H, benzyl-H), 2.92-2.79 (m, 2H, pip-H), 2.44-2.34 (m, 2H, NCH$_2$), 2.10-1.98 (m, 2.2H, dioxane-H, pip-H), 1.86-1.51 (m, 6H, pip-H, NCH$_2$CH$_2$), 1.34-1.23 (m, 1.8H, pip-H, dioxane-H). HPLC t$_R$=6.1 min.

N-{1-[2-(1,3-Dioxan-2-yl)ethyl]piperidin-4-yl}-N-(4-fluorobenzyl)-2-[4-(2-fluoroethoxy)-phenyl]acetamide, oxalate (118AF85-113)

The desired compound was synthesized from 118AF52-95 (360 mg, 1.11 mmol) and 4-(2-fluoroethoxy)phenylacetyl chloride (282 mg, 1.30 mmol) using the same method as for preparation of 118AF66-102. Further purification by acidic ion-exchange SPE cartridge was performed. Yield: 84 mg, 15%.

$R_f$=0.36 (MeOH/CH$_2$Cl$_2$, 5:95). LCMS m/z 503 [M+H]$^+$. $^1$NMR (CDCl$_3$, rotamers 0.4:0.6) δ 7.27-6.84 (m, 8H, Ar—H), 4.80 (m, 1H, OCH$_2$CH$_2$F), 4.68 (m, 1H, OCH$_2$CH$_2$F), 4.65-4.45 (m, 3.6H, pip-H, dioxane-H, benzyl-H), 4.22 (m, 1H, OCH$_2$CH$_2$F), 4.16 (m, 1H, OCH$_2$CH$_2$F), 4.10-4.03 (m, 2H, dioxane-H), 3.79-3.68 (m, 3.2H, dioxane-H, pip-H, benzyl-H), 3.51 (s, 1.2H, benzyl-H), 2.92-2.82 (m, 2H, pip-H), 2.44-2.36 (m, 2H, NCH$_2$), 2.12-1.99 (m, 2.2H, dioxane-H, pip-H), 1.88-1.51 (m, 6H, pip-H, NCH$_2$CH$_2$), 1.35-1.26 (m, 1.8H, pip-H, dioxane-H). HPLC $t_R$=7.0 min.

N-{1-[2-(5,5-Dimethyl-1,3dioxan-2-yl)ethyl]piperidin-4-yl}-N-(4-fluorobenzyl)-2-(4-isobutoxyphenyl)acetamide, oxalate (118AF27-83)

The desired compound was synthesized from N-{1-[2-(1,3-dioxan-2-yl)ethyl]piperidin-4-yl}-N-(4-fluorobenzyl)-2-(4-isobutoxyphenyl)acetamide 103NLS63F (22 mg, 0.042 mmol) and 2,2-dimethyl-1,3-propandiol (33 mg, 0.38 mmol) using the same method as for preparation of 130AF12-148. Purification of the product by reversed phase HPLC (C$_{18}$) afforded the title compound (2.8 mg, 12%). LCMS m/z 541 [M+H]$^+$. HPLC $t_R$=9.9 min.

N-(4-Fluorobenzyl)-2-(4-isobutoxyphenyl)-N-{1-[2-((R)-4-methyl-1,3-dioxan-2-yl)ethyl]-piperidin-4-yl}acetamide, oxalate (118AF29-84)

The desired compound was synthesized from N-{1-[2-(1,3-dioxan-2-yl)ethyl]piperidin-4-yl}-N-(4-fluorobenzyl)-2-(4-isobutoxyphenyl)acetamide 103NLS63F (38 mg, 0.074 mmol) and (R)-(−)-1,3-butanediol (33 mg, 0.38 mmol) using the same method as for preparation of 130AF12-148. Purification of the product by reversed phase HPLC (C$_{18}$) afforded the title compound (11.6 mg, 28%). LCMS m/z 527 [M+H]$^+$. HPLC $t_R$=8.7 min.

N-(4-Fluorobenzyl)-2-(4-isobutoxyphenyl)-N-{1-[2-((S)-4-methyl-1,3-dioxolan-2-yl)ethyl]-piperidin-4-yl]acetamide, oxalate (118AF31-85)

The desired compound was synthesized from N-{1-[2-(1,3-dioxan-2-yl)ethyl]piperidin-4-yl}-N-(4-fluorobenzyl)-2-(4-isobutoxyphenyl)acetamide 103NLS63F (40 mg, 0.078 mmol) and (S)-(+)-propylene glycol (30 mg, 0.39 mmol) using the same method as for preparation of 130AF12-148. Purification of the product by reversed phase HPLC (C$_{18}$) afforded the title compound (21 mg, 53%). LCMS m/z 513 [M+H]$^+$. HPLC $t_R$=9.9 min.

N-{1-[2-(4,6-Dimethyl-1,3-dioxan-2-yl)ethyl]piperidin-4-yl}-N-(4-fluorobenzyl)-2-(4-isobutoxyphenyl)acetamide, oxalate (118AF37-88)

The desired compound was synthesized from N-{1-[2-(1,3-dioxan-2-yl)ethyl]piperidin-4-yl}-N-(4-fluorobenzyl)-2-(4-isobutoxyphenyl)acetamide 103NLS63F (40 mg, 0.078 mmol) and 2,4-pentandiol (41 mg, 0.39 mmol) using the same method as for preparation of 130AF12-148. Purification of the product by reversed phase HPLC (C$_{18}$) afforded the title compound (9 mg, 21%). LCMS m/z 541 [M+H]$^+$. HPLC $t_R$=10.5 min.

N-(4-Fluorobenzyl)-N-{1-[2-((S)-4-methyl-1,3-dioxolan-2-yl)ethyl]piperidin-4-yl}-2-(4-trifluoromethoxyphenyl)acetamide, oxalate (118AF87-114)

The desired compound was synthesized from N-{1-[2-(1,3-dioxan-2-yl)ethyl]piperidin-4-yl}-N-(4-fluorobenzyl)-2-(4-trifluoromethoxyphenyl)acetamide 118AF58-98 (70 mg, 0.13 mmol) and (S)-(+)-propylene glycol (53 mg, 0.69 mmol) using the same method as for preparation of 130AF12-148. Purification of the product by silica gel column chromatography, eluting with a stepwise gradient of 0-4% methanol in dichloromethane, afforded the title compound (31 mg, 46%).

$R_f$=0.17 (MeOH/CH$_2$Cl$_2$ 4:96). LCMS m/z 525 [M+H]$^+$. $^1$NMR (CDCl$_3$, rotamers 0.4:0.6) δ 7.34-6.91 (m, 8H, Ar—H), 5.03 & 4.92 (2t, 1H, J=4.8, dioxolane-H), 4.66-4.56 (m, 0.6H, pip-H), 4.52 & 4.49 (2s, 2H, benzyl-H), 4.22-4.07 (m, 1.4H, dioxolane-H), 3.95-3.89 (m, 0.6H, dioxolane-H), 3.84 (s, 0.8H, benzyl-H), 3.74-3.64 (m, 0.4H, pip-H), 3.57 (s, 1.2H, benzyl-H), 3.40-3.33 (m, 1H, dioxolane-H), 2.78-2.86 (m, 2H, pip-H), 2.49-2.38 (m, 2H, NCH$_2$), 2.10-2.01 (m, 1.2H, pip-H), 1.70-1.53 (m, 6H, pip-H, NCH$_2$CH$_2$), 1.40-1.22 (m, 3.8H, pip-H, CH$_3$). HPLC $t_R$=8.7 min.

N-(4-Fluorobenzyl)-2-(4-isopropylphenyl)-N-{1-[2-((S)-4-methyl-1,3-dioxolan-2-yl)ethyl]-piperidin-4-yl}acetamide, oxalate (118AF91-117)

The desired compound was synthesized from N-{1-[2-(1,3-dioxan-2-yl)ethyl]piperidin-4-yl}-N-(4-fluorobenzyl)-2-(4-isopropylphenyl)acetamide 118AF63-100 (150 mg, 0.31 mmol) and (S)-(+)-propylene glycol (95 mg, 1.24 mmol) using the same method as for preparation of 130AF12-148. Purification by silica gel column chromatography, eluting with a stepwise gradient of 0-4% methanol in dichloromethane, afforded the title compound (51.2 mg, 34%).

$R_f$=0.19 (MeOH/CH$_2$Cl$_2$, 4:96). LCMS m/z 483 [M+H]$^+$. $^1$NMR (CDCl$_3$, rotamers 0.4:0.6) δ 7.24-6.90 (m, 8H, Ar—H), 5.03 & 4.92 (2t, 1H, J=4.8, dioxolane-H), 4.67-4.55 (m, 0.6H, pip-H), 4.51 & 4.47 (2s, 2H, benzyl-H), 4.21-4.07 (m, 1.4H, dioxolane-H), 3.94-3.89 (m, 0.6H, dioxolane-H), 4.81-3.50 (m, 1.2H, benzyl-H, pip-H), 3.55 (s, 1.2H, benzyl-H), 3.40-3.33 (m, 1H, dioxolane-H), 2.94-2.83 (m, 3H, pip-H, CH(CH$_3$)$_2$), 2.47-2.38 (m, 2H, NCH$_2$), 2.09-2.01 (m, 1.2, pip-H), 1.86-1.52 (m, 6H, pip-H, NCH$_2$CH$_2$), 1.31-1.19 (m, 9.8H, pip-H, CH$_3$, CH(CH$_3$)$_2$). HPLC $t_R$=8.6 min.

N-(4-Fluorobenzyl)-N-{1-[2-((R)-4-methyl-1,3-dioxan-2-yl)ethyl]piperidin-4-yl}-2-(4-trifluoromethoxyphenyl)acetamide, oxalate (118AF75-108)

The desired compound was synthesized from N-{1-[2-(1,3-dioxan-2-yl)ethyl]piperidin-4-yl}-N-(4-fluorobenzyl)-2-(4-trifluoromethoxyphenyl)acetamide 118AF58-98 (70 mg, 0.13 mmol) and (R)-(−)-1,3-butanediol (60 mg, 0.66 mmol) using the same method as for preparation of 130AF12-148. Purification of the product by silica gel column chromatography, eluting with a stepwise gradient of 0-4% methanol in dichloromethane, afforded the title compound (28 mg, 40%).

$R_f$=0.24 (MeOH/CH$_2$Cl$_2$, 5:95). LCMS m/z 539 [M+H]$^+$. $^1$H NMR (CDCl$_3$, rotamers 0.4:0.6) δ 7.33-6.91 (m, 8H, Ar—H), 4.64-4.48 (m, 3.6H, benzyl-H, dioxane-H, pip-H), 4.04 (m, 1H, dioxane-H), 3.83 (s, 0.8H, benzyl-H), 3.75-3.63 (m, 2.4H, dioxane-H, pip-H), 3.56 (s, 1.2H, benzyl-H), 2.92-2.83 (m, 2H, pip-H), 2.44-2.38 (m, 2H, NCH$_2$), 2.09-2.01 (m, 1.2 pip-H), 1.89-1.53 (m, 7H, dioxane-H, pip-H, NCH$_2$CH$_2$), 1.44-1.31 (m, 1.8H, dioxane-H, pip-H), 1.19 (m, 3H, CH$_3$). HPLC $t_R$=9.0 min.

N-(4-Fluorobenzyl)-2-(4-isobutoxyphenyl)-N-{1-[2-(2,5,5-trimethyl-1,3-dioxan-2-yl)ethyl]piperidin-4-yl]acetamide, oxalate (118AF33-86)

The desired compound was synthesized from N-(4-fluorobenzyl)-2-(4-isobutoxyphenyl)-N-piperidin-4-yl-acetamide103NLS56 (145 mg, 0.36 mmol) and 2-(2-bromoethyl)-2,5,5-trimethyl-1,3-dioxane (104.5 mg, 0.44 mmol) using the same method as for synthesis of 130AF65-182. Purification of the product by silica gel column chromatography, eluting with 5% methanol in dichloromethane, afforded the title compound (119 mg, 58%).

$R_f$=0.15 (MeOH/CH$_2$Cl$_2$, 5:95). LCMS m/z 555 [M+H]$^+$. $^1$H NMR (CDCl$_3$, rotamers 0.4:0.6) δ 7.20-6.79 (m, 8H, Ar—H), 4.66-4.56 (m, 0.6H, pip-H), 4.49 & 4.43 (2s, 2H, benzyl-H), 3.76-3.68 (m, 3.2H, pip-H, benzyl-H, CH$_{2OiBu}$), 3.52-3.47 (m, 4H, dioxane-H), 3.41 (m, 1.2H, benzyl-H), 2.93-2.84 (m, 2H, pip-H), 2.48-2.40 (m, 2H, NCH$_2$), 2.11-2.00 (m, 2.2H, CH$_{OiBu}$, pip-H), 1.87-1.80 (m, 2.8H, pip-H, NCH$_2$CH$_2$), 1.72-1.50 (m, 3.2H, pip-H), 1.33 (s, 3.8H, CH$_3$, pip-H), 1.02-0.87 (m, 12H, CH$_3$). HPLC $t_R$=9.8 min.

N-(4-Fluorobenzyl)-2-(4-isobutoxyphenyl)-N-{1-[2-(2-methyl-1,3-dioxolan-2-yl)ethyl]-piperidin-4-yl}acetamide, oxalate (118AF35-87)

The desired compound was synthesized from N-(4-fluorobenzyl)-2-(4-isobutoxyphenyl)-N-piperidin-4-yl-acetamide 103NLS56 (311 mg, 0.78 mmol) and 2-(2-bromoethyl)-2-methyl-1,3-dioxolane (188 mg, 0.96 mmol) using the same method as for synthesis of 130AF65-182. Purification by silica gel column chromatography, eluting with 5% methanol in dichloromethane, afforded the title compound (61 mg, 15%).

$R_f$=0.20 (MeOH/CH$_2$Cl$_2$, 5:95). LCMS m/z 513 [M+H]$^+$. $^1$H NMR (CDCl$_3$, rotamers 0.4:0.6) δ 7.17-6.76 (m, 8H, Ar—H), 4.64-4.52 (m, 0.6H, pip-H), 4.47 & 4.41 (2s, 2H, benzyl-H), 3.93-3.82 (m, 4H, dioxolane-H), 3.76-3.63 (m, 3.2H, benzyl-H, CH$_{2OiBu}$, pip-H), 3.47 (s, 1.2H, benzyl-H), 2.94-2.83 (m, 2H, pip-H), 2.43-2.32 (m, 2H, NCH$_2$), 2.12-1.97 (m, 2.2H, CH$_{OiBu}$, pip-H), 1.84-1.72 (m, 2.8H, pip-H, NCH$_2$CH$_2$), 1.70-1.50 (m, 3.2H, pip-H), 1.27 (s, 3.8H, CH$_3$, pip-H), 0.98 (m, 6H, CH$_{3OiBu}$). HPLC $t_R$=8.8 min.

N-(4-Fluorobenzyl)-2-(4-isobutoxyphenyl)-N-{1-[3-(1,3-dioxolan-2-yl)propyl]piperidin-4-yl}acetamide, tartrate (118AF79-39)

The desired compound was synthesized from N-(4-fluorobenzyl)-2-(4-isobutoxyphenyl)-N-piperidin-4-yl-acetamide 103NLS56 (156 mg, 0.39 mmol) and 2-(3-chloropropyl)-1,3-dioxolane (62 μL, 0.47 mmol) using the same method as for synthesis of 130AF65-182. Purification by silica gel column chromatography, eluting with a stepwise gradient of 0-4% methanol in dichloromethane, afforded the title compound (49 mg, 25%).

$R_f$=0.45 (MeOH/CH$_2$Cl$_2$, 7:93). LCMS m/z 513 [M+H]$^+$. $^1$H NMR (CDCl$_3$, rotamers 0.4:0.6) δ 7.21-6.79 (m, 8H, Ar—H), 4.84 (t, 1H, J=4.4, dioxolane-H), 4.66-4.56 (m, 0.6H, pip-H), 4.50 & 4.44 (2s, 2H, benzyl-H), 3.95-3.90 (m, 2H, dioxolane-H), 3.84-3.67 (m, 5.2H, benzyl-H, CH$_{2OiBu}$, pip-H, dioxolane-H), 3.50 (s, 1.2H, benzyl-H), 2.94-2.84 (m, 2H, pip-H), 2.34-2.27 (m, 2H, NCH$_2$), 2.10-1.98 (m, 2.2H, CH$_{OiBu}$, pip-H), 1.84-1.78 (m, 0.8H, pip-H), 1.71-1.50 (m, 7.2H, pip-H, NCH$_2$CH$_2$), 1.34-1.25 (m, 0.8H, pip-H), 1.01 (m, 6H, CH$_{3OiBu}$). HPLC $t_R$=8.0 min.

N-(4-Fluorobenzyl)-2-(4-isobutoxyphenyl)-N-{1-(3-piperidin-1-yl-propyl)piperidin-4-yl}-acetamide, dihydrochloride (98AF36-43)

The desired compound was synthesized from N-(4-fluorobenzyl)-2-(4-isobutoxyphenyl)-N-piperidin-4-yl-acetamide103NLS56 (189 mg, 0.47 mmol), 1-piperidine (61 μL, 0.61 mmol) and 1-chloro-3-iodopropane (61 μL, 0.57 mmol) using the same method as for synthesis of 130AF09-145. Purification of the product by silica gel column chromatography, eluting with 10% methanol in dichloromethane, afforded the title compound (75.6 mg, 31%).

$R_f$=0.13 (MeOH/CH$_2$Cl$_2$, 1:4). LCMS m/z 524 [M+H]$^+$. $^1$H NMR (CDCl$_3$, rotamers 0.4:0.6) δ 7.21-6.81 (m, 8H, Ar—H), 4.66-4.54 (m, 0.6H, pip-H), 4.51 & 4.45 (2s, 2H, benzyl-H), 3.78-3.68 (m, 3.2H, benzyl-H, CH$_{2OiBu}$, pip-H), 3.52 (s, 1.2H, benzyl-H), 2.93-2.83 (m, 2H, pip-H), 2.40-2.23 (m, 8H, NCH$_2$), 2.15-1.26 (m, 15H, pip-H, CH(CH$_3$)$_2$, CH$_2$), 1.02 (m, 6H, CH(CH$_3$)$_2$). HPLC $t_R$=8.0 min.

N-(4-Fluorobenzyl)-2-(4-isobutoxyphenyl)-N-{1-[2-(tetrahydropyran-2-yloxy)ethyl]-piperidin-4-yl}acetamide, oxalate (98AF41-44)

The desired compound was synthesized from N-(4-fluorobenzyl)-2-(4-isobutoxyphenyl)-N-piperidin-4-yl-acetamide 103NLS56 (185 mg, 0.46 mmol) and 2-(2-chloroethoxy)-tetrahydro-2H-pyran (75 μL, 0.51 mmol) using the same method as for synthesis of 130AF09-145. Purification of the product by silica gel column chromatography, eluting with 4.5% methanol in dichloromethane, afforded the title compound (96 mg, 40%).

$R_f$=0.18 (MeOH/CH$_2$Cl$_2$, 4:96). LCMS m/z 527 [M+H]$^+$. $^1$H NMR (CDCl$_3$, rotamers 0.4:0.6) δ 7.21-6.78 (m, 8H, Ar—H), 4.67-4.56 (m, 0.6H, pip-H), 4.54 (m, 1H, THP), 4.49 & 4.44 (2s, 2H, benzyl-H), 3.86-3.66 (m, 5.2H, benzyl-H, CH$_{2OiBu}$, pip-H, CHO), 3.58-3.43 (m, 3.2H, benzyl-H, CHO), 3.01-2.89 (m, 2H, pip-H), 2.62 & 2.55 (2t, 2H, J=6.0, NCH$_2$CH$_2$O), 2.26-2.17 (m, 1.2H, pip-H), 2.12-1.96 (m, 1.8H, CH$_{OiBu}$, pip-H), 1.82-1.44 (m, 9.2H, pip-H, THP), 1.33-1.26 (m, 0.8H, pip-H), 1.01 (m, 6H, CH(CH$_3$)$_2$). HPLC $t_R$=7.2min.

N-(4-Fluorobenzyl)-2-(4-isobutoxyphenyl)-N-{1-[3-(2-oxo-piperidin-1-yl)propyl]piperidin-4-yl}acetamide (98AF73-64)

Sodium hydride (60% suspension in oil, 26 mg, 0.65 mmol) was added to a solution of 2-piperidone (54 mg, 0.54 mmol) in dry THF (2 mL) under argon atmosphere. After 15 minutes stirring at rt the reaction mixture was cooled to 0° C. over 15 minutes. A solution of 1-bromo-3-chloropropane (160 μL, 1.62 mmol) was added dropwise to the cold mixture and stirring was continued overnight at rt. The mixture was partitioned between water and ethyl acetate, the organic layer dried over sodium sulphate, filtered and evaporated to dryness. Purification of the residue on silica gel column chromatography, eluting with a stepwise gradient of 60-80% ethyl acetate in n-heptane, afforded 1-(3-chloropropyl)-piperidin-2-one (33 mg, 35%).

$R_f$=0.22 (ethyl acetate/n-heptane 8:2). LCMS m/z 176 [M+H]$^+$. HPLC $t_R$=1.8 min.

A solution of 1-(3-chloropropyl)-piperidin-2-one (32 mg, 0.18 mmol) in dry DMF (2 mL) was added to a suspension of potassium carbonate (52 mg, 0.38 mmol) and N-(4-fluorobenzyl)-2-(4-isobutoxyphenyl)-N-piperidin-4-yl-acetamide 103NLS56 (62 mg, 0.15 mmol) in dry DMF (2 mL). After addition of sodium iodide (25 mg, 0.17 mmol) the mixture was stirred overnight at 48° C. Afterwards it was partitioned between water and dichloromethane. The organic layer were dried over sodium sulphate, filtered and evaporated to dryness. Purification of the residue by reversed phase HPLC ($C_{18}$) afforded the desired compound (2.6 mg, 3%).

$R_f$=0.11 (MeOH/CH$_2$Cl$_2$ 5:95). LCMS m/z 538 [M+H]$^+$. HPLC $t_R$=8.2 min.

N-(4-Fluorobenzyl)-2-(4-isobutoxyphenyl)-N-{1-[3-(2-oxo-pyrrolidin-1-yl)propyl]piperidin-4-yl}acetamide, hydrochloride (98AF76-65)

The desired compound was synthesized from N-(4-fluorobenzyl)-2-(4-isobutoxyphenyl)-N-piperidin-4-yl-acetamide 103NLS56 (107 mg, 0.27 mmol), 2-pyrrolidone and 1-bromo-3-chloropropane using the same method as for synthesis of 98AF73-64. Purification of the product by silica gel column chromatography, eluting with a stepwise gradient of 4-8% methanol in dichloromethane, afforded the title compound (15 mg, 11%).

$R_f$=0.39 (MeOH/CH$_2$Cl$_2$ 1:9). LCMS m/z 524 [M+H]$^+$. $^1$H NMR (CDCl$_3$, rotamers 0.4:0.6) δ 7.20-6.80 (m, 8H), 4.65-4.53 (m, 0.6H), 4.50 & 4.44 (2s, 2H), 3.76-3.67 (m, 3.2H), 3.51 (m, 1.2H), 3.34 (t, 2H, J=7.2), 3.26 (t, 2H, J=7.2), 2.95-2.82 (m, 2H), 2.38-2.25 (m, 4H), 2.12-1.96 (m, 4.2H), 1.86-1.56 (m, 6H), 1.29 (m, 0.8H), 1.01 (m, 6H). HPLC $t_R$=7.6 min.

N-(4-Fluorobenzyl)-2-(4-isobutoxyphenyl)-N-{1-[3-((R)-4-isopropyl-2-oxo-oxazolidin-3-yl)propyl]piperidin-4-yl}acetamide, oxalate (98AF100-73)

Sodium hydride (55% suspension in oil, 144 mg, 3.31 mmol) was added to a solution of (R)-4-isopropyl-2-oxazolidinone (356 mg, 2.75 mmol) in dry tetrahydrofuran (17 mL) under argon atmosphere. The suspension was stirred for 1 hour at rt, then cooled to 0° C. and a solution of 1-bromo-3-chloropropane in dry tetrahydrofuran (3 mL) was added dropwise. After 48 h stirring at 58° C. the mixture was quenched with water. The solvent was removed by evaporation under reduced pressure and the residue partitioned between water and dichloromethane. The organic layer was evaporated to dryness. Purification of the residue by silica gel column chromatography, eluting with a mixture of ethyl acetate and n-Heptane (70:30), afforded (4R)-3-(3-chloropropyl)-4-isopropyloxazolidinon-2-one (401 mg, 71%).

A solution of (4R)-3-(3-chloropropyl)-4-isopropyloxazolidinon-2-one (160 mg, 0.78 mmol) in dry DMF (2 mL) was added to a suspension of potassium carbonate (217 mg, 1.57 mmol) and N-(4-fluorobenzyl)-2-(4-isobutoxyphenyl)-N-piperidin-4-yl-acetamide 103NLS56 (250 mg, 0.63 mmol) in dry DMF (6 mL). After addition of sodium iodide (113 mg, 0.75 mmol) the mixture was stirred overnight at 62° C. and partitioned between water and dichloromethane. The organic layer were dried over sodium sulphate, filtered and evaporated to dryness. Purification of the residue by silica gel column chromatography, eluting with 5% methanol in dichloromethane, afforded the desired compound (143 mg, 40%).

$R_f$=0.28 (MeOH/CH$_2$Cl$_2$ 6:96). LCMS m/z 568 [M+H]$^+$. $^1$H NMR (CDCl$_3$, rotamers 0.4:0.6) δ 7.20-6.78 (m, 8H, Ar—H), 4.61-4.51 (m, 0.6H, pip-H), 4.48 & 4.42 (2s, 2H, benzyl-H), 4.15 (t, 1H, J=8.8, oxa-H), 4.01 (m, 1H, oxa-H), 3.78-3.64 (m, 4.2H, pip-H, benzyl-H, oxa-H, CH$_{2OiBu}$), 3.48 (m, 2.2H, benzyl-H, CONCHCH$_2$), 2.92-2.79 (m, 3H, pip-H, CONCHCH$_2$), 2.34-2.22 (m, 2H, NCH$_2$CH$_2$CH$_2$), 2.10-1.96 (m, 3.2H, pip-H, CH$_{iPr}$, CH$_{OiBu}$), 1.76-1.50 (m, 6H, pip-H, NCH$_2$CH$_2$), 1.32-1.26 (m, 0.8H, pip-H), 0.99 (m, 6H, CH$_{3OiBu}$), 0.81-0.87 (m, 6H, CH$_{3iPr}$). HPLC $t_R$=9.1 min.

N-(4-Fluorobenzyl)-2-(4-isobutoxyphenyl)-N-{1-[3-(2-oxo-oxazolidin-3-yl)propyl]piperidin-4-yl}acetamide, oxalate (98AF94-71)

The desired compound was synthesized from N-(4-fluorobenzyl)-2-(4-isobutoxyphenyl)-N-piperidin-4-yl-acetamide 103NLS56 (298 mg, 0.75 mmol), 2-oxazolidone and 1-bromo-3-chloropropane using the same method as for synthesis of 98AF100-73. Purification of the product by silica gel column chromatography, eluting with 5% methanol in dichloromethane, afforded the title compound (157 mg, 40%).

$R_f$=0.23 (MeOH/CH$_2$Cl$_2$ 5:95). LCMS m/z 526 [M+H]$^+$. $^1$H NMR (CDCl$_3$, rotamers 0.4:0.6) δ 7.20-6.78 (m, 8H, Ar—H), 4.61-4.50 (m, 0.6H, pip-H), 4.48 & 4.42 (2s, 2H, benzyl-H), 4.29-4-24 (m, 2H, oxa-OCH$_2$), 3.78-3.65 (m, 3.2H, pip-H, benzyl-H, CH$_{2OiBu}$), 3.52-3.48 (m, 3.2H, benzyl-H, oxa-NCH$_2$), 3.25 (t, 2H, J=7.2, CONCH$_2$CH$_2$CH$_2$N), 2.89-2.80 (m, 2H, pip-H), 2.33-2.26 (m, 2H, NCH$_2$CH$_2$CH$_2$NCO), 2.09-1.76 (m, 3H, pip-H, CH$_{OiBu}$), 1.71-1.49 (m, 5.2H, pip-H, NCH$_2$CH$_2$), 1.33-1.27 (m, 0.8H, pip-H), 1.00 (m, 6H, CH$_{3OiBu}$). HPLC $t_R$=7.8 min.

(S)-4-Methyl-oxazolidin-2-one (118AF10-77)

Triethylamine (0.94 mL, 6.65 mmol) was added dropwise to a solution of L-alaninol (500 mg, 6.65 mmol) and 1,1-carbonyldiimidazole (1.29 g, 7.98 mmol) in dry THF (10 mL) at rt, under argon atmosphere. The reaction mixture was stirred overnight at 60° C. The solvent was removed by evaporation under reduced pressure. Purification of the residue by silica gel column chromatography, eluting with 6% methanol in dichloromethane, afforded the desired compound (450 mg, 67%).

$R_f$=0.39 (MeOH/CH$_2$Cl$_2$ 6:94). $^1$H NMR (CDCl$_3$) δ 6.74 (m, 1H), 4.45-4.34 (m, 1H), 4.98-4.77 (m, 2H), 1.17 (m, 3H).

N-(4-Fluorobenzyl)-2-(4-isobutoxyphenyl)-N-{1-[3-((S)-4-methyl-2-oxo-oxazolidin-3-yl)propyl]piperidin-4-yl}acetamide, tartrate (118AF18-81)

The desired compound was synthesized from N-(4-fluorobenzyl)-2-(4-isobutoxyphenyl)-N-piperidin-4-yl-acetamide 103NLS56 (205 mg, 0.52 mmol), (S)-4-methyl-oxazolidin-2-one (118AF10-77) and 1-bromo-3-chloropropane using the same method as for synthesis of 98AF100-73. Further purification by acidic ion-exchange SPE cartridge was performed. Yield: 106 mg, 38%.

$R_f$=0.22 (MeOH/CH$_2$Cl$_2$ 6:94). LCMS m/z 540 [M+H]$^+$. $^1$H NMR (CDCl$_3$, rotamers 0.4:0.6) δ 7.20-6.78 (m, 8H, Ar—H), 4.61-4.50 (m, 0.6H, pip-H), 4.48 & 4.42 (2s, 2H, benzyl-H), 4.34 (m, 1H, oxa-H), 3.84-3.66 (m, 5.2H, pip-H, benzyl-H, oxa-H, CH$_{2OiBu}$), 3.49 (s, 1.2H, benzyl-H), 3.42-3.34 (m, 1H, CONCH$_2$), 3.09-3.00 (m, 1H, CONCH$_2$), 2.92-

2.79 (m, 2H, pip-H), 2.33-2.26 (m, 2H, NCH$_2$), 2.10-1.98 (m, 2.2H, pip-H, CH$_{OiBu}$), 1.86-1.76 (m, 0.8H, pip-H), 1.72-1.48 (m, 5.2H, pip-H, NCH$_2$CH$_2$), 1.29 (m, 0.8H, pip-H), 1.22 (m, 3H, oxa-CH$_3$), 0.99 (m, 6H, CH$_{3OiBu}$). HPLC t$_R$=8.4 min.

V. (S)-4-Ethyl-oxazolidin-2-one (118AF08-76)

Triethylamine (0.80 mL, 5.74 mmol) was added dropwise to a solution of (S)-(+)-2-amino-1-butanol (515 mg, 5.77 mmol) and 1,1-carbonyldiimidazole (1.10 g, 6.78 mmol) in dry THF (10 mL) at rt under argon atmosphere. The reaction mixture was stirred overnight at rt. The solvent was removed by evaporation under reduced pressure. Purification of the residue by silica gel column chromatography, eluting with 6% methanol in dichloromethane, afforded the desired compound (485 mg, 73%). R$_f$=0.42 (MeOH/CH$_2$Cl$_2$ 6:94).

N-(4-Fluorobenzyl)-2-(4-isobutoxyphenyl)-N-{1-[3-((S)-4-ethyl-2-oxo-oxazolidin-3-yl)-propyl]piperidin-4-yl}acetamide, oxalate (118AF16-80)

The desired compound was synthesized from N-(4-fluorobenzyl)-2-(4-isobutoxyphenyl)-N-piperidin-4-yl-acetamide 103NLS56 (202 mg, 0.51 mmol), (S)-4-ethyl-oxazolidin-2-one (118AF08-76) and 1-bromo-3-chloropropane using the same method as for synthesis of 98AF100-73. Purification of the product by acidic ion-exchange SPE cartridge afforded the title compound (126 mg, 44%).

R$_f$=0.28 (MeOH/CH$_2$Cl$_2$ 6:94). LCMS m/z 554 [M+H]$^+$. $^1$H NMR (CDCl$_3$, rotamers 0.4:0.6) δ 7.20-6.78 (m, 8H, Ar—H), 4.61-4.52 (m, 0.6H, pip-H), 4.48 & 4.42 (2s, 2H, benzyl-H), 4.32-4.26 (m, 1H, oxa-H), 3.94-3.88 (m, 1H, oxa-H), 3.76-3.66 (m, 4.2H, pip-H, benzyl-H, oxa-H, CH$_{2OiBu}$), 3.49 (s, 1.2H, benzyl-H), 3.46-3.37 (m, 1H, CONCH$_2$), 3.04-2.96 (m, 1H, CONCH$_2$), 2.90-2.78 (m, 2H, pip-H), 2.33-2.24 (m, 2H, NCH$_2$), 2.11-1.96 (m, 2.2H, pip-H, CH$_{OiBu}$), 1.82-1.75 (m, 0.8H, pip-H), 1.74-1.42 (m, 7.2H, pip-H, NCH$_2$CH$_2$, CH$_2$CH$_3$), 1.29 (m, 0.8H, pip-H), 1.00 (m, 6H, CH$_{3OiBu}$), 0.85 (m, 3H, CH$_2$CH$_3$). HPLC t$_R$=8.7 min.

2-(2-Bromoethyl)-1,3-oxothiolane (121JP11)

Adapting a procedure by Yamada et al (*Tetrahedron Lett.*, 1998, 39, 7709-7712), boron trifluoride ether complex (5 mL, 40 mmol) was added dropwise to a mixture of 2-(2-bromoethyl)-1,3-dioxolane (1.45 g, 8.0 mmol) and 2-mercaptoethanol (2.81 mL, 40 mmol) in dichloromethane (15 mL) at rt under Ar atmosphere and stirred at rt overnight. Sat. aq. NaHCO$_3$ (100 mL) was added to the crude mixture, followed by extraction using Et$_2$O (3×100 mL), drying (Na$_2$SO$_4$) and evaporation in vacuo. Purification by Kugelrohr distillation (90° C., 1.0 mmHg) afforded 1.08 g of the title compound as a yellow oil. The purity of this material after distillation was 71% (determined by GC analysis) and it was used as such in the alkylation step (121JP12).

N-(4-Fluorobenzyl)-2-(4-isobutoxyphenyl)-N-{1-[2-(1,3-oxothiolan-2-yl)ethyl]piperidin-4-yl}acetamide, L-tartrate (121JP12)

The title compound was prepared by the general procedure described above for 103NLS63-F using 103NLS56 (130 mg, 0.33 mmol) and 121JP11 (85 mg, 0.43 mmol) as the alkylating agent. Workup as in 121JP11 followed by vacuum filtration chromatography over silica gel (VFC, ethyl acetate/n-heptane 0:1→ethyl acetate/n-heptane 1:0→ethyl acetate/ MeOH 4:1) gave 85 mg (51%) of 121JP12 as colourless thick oil. The L-tartrate salt was prepared as described above.

R$_f$=0.57 (MeOH/CH$_2$Cl$_2$ 1:10). LCMS m/z 515 [M+H]$^+$. $^1$H-NMR (CDCl$_3$, rotamers 0.5:0.5) δ 7.20-6.76 (m, 8H), 5.10-5.00 (m, 1H, oxothiolane-H), 4.66-4.54 (m, 0.5H, pip-H), 4.48 and 4.42 (2s, 2H, benzyl-H), 4.30-4.22 (m, 1H, oxothiolane-H), 3.78-3.64 (m, 4.5H, pip-H, benzyl-H, oxothiolane-H, OCH$_{2OiBu}$), 3.48 (s, 1H, benzyl-H), 3.01-2.82 (m, 4H, pip-H, oxothiolane-H), 2.60-2.34 (m, 2H, NCH$_2$), 2.21-1.56 (m, 8H, pip-H, NCH$_2$CH$_2$, CH$_{OiBu}$), 1.32-1.22 (m, 1H, pip-H), 1.04-0.96 (m, 6H, CH$_{3OiBu}$. HPLC t$_R$=10.1 min.

2-(4-Bromophenyl)-N-{1-[2-(1,3-dioxan-2-yl)ethyl)piperidin-4-yl}-N-(4-fluorobenzyl)-acetamide, L-tartrate (121JP13)

The title compound was prepared by the procedure described above for 117NLS87-A using 118AF52-95 (200 mg, 0.62 mmol) and 4-bromophenylacetic acid (500 mg, 2.32 mmol). Sat. aq. NaHCO$_3$ (100 mL) was added to the crude mixture, followed by extraction using CH$_2$Cl$_2$ (3×100 mL), drying (Na$_2$SO$_4$) and evaporation in vacuo. VFC over silica gel (ethyl acetate/n-heptane 1:1-→ ethyl acetate/n-heptane 1:0→ ethyl acetate/MeOH 2:1) gave 250 mg (78%) of 121JP12 as a thick oil. The L-tartrate salt was prepared as described above.

R$_f$=0.49 (MeOH/CH$_2$Cl$_2$ 1:10). LCMS m/z 521 [M+H]$^+$. $^1$H-NMR (CDCl$_3$, rotamers 0.6:0.4) δ 7.50-6.88 (m, 8H), 4.62-4.57 (m, 0.4H, pip-H), 4.50 (t, 1H, J=4.9, dioxane-H) 4.48 and 4.42 (2s, 2H, benzyl-H), 4.06-4.00 (m, 2H, dioxane-H), 3.76 and 3.50 (2s, 2H, benzyl-H), 3.75-3.60 (m, 2.6H, pip-H, dioxane-H), 3.01 and 2.90 (2d, 2H, J=10.5, pip-H), 2.52 and 2.41 (2t, 2H, J=8.0, NCH$_2$), 2.10-1.98 (m, 2.2 H, dioxane-H, pip-H), 1.97-1.58 (m, 6H, pip-H, NCH$_2$CH$_2$), 1.38-1.20 (m, 1.8H, dioxane-H, pip-H). HPLC t$_R$=8.3 min.

N-{1-[2-(1,3-Dioxan-2-yl)ethyl)piperidin-4-yl}-N-(4-fluorobenzyl)-2-(4-isobutylamino-phenyl)acetamide, L-tartrate (121JP27)

Adapting a protocol by Buchwald et al (*J. Am. Chem. Soc.*, 1996, 118, 7215-7216), 121JP13 (100 mg, 192 μmol), isobutylamine (17 mg, 230 μmol), Pd$_2$dba$_3$ (11.6 mg, 19.2 μmol), BINAP (12.0 mg, 38.4 μmol) and NaOtBu (25.8 mg, 269 μmol) were weighed into a flask, toluene (2 mL) was added and the resulting mixture was stirred at 80° C. for 18 h. Workup as in 121JP13 followed by preparative reversed-phase (C$_{18}$) HPLC afforded 25.7 mg (27.0%) of 121JP27 as a thick colourless oil. The L-tartrate salt was prepared as described above.

R$_f$=0.30 (MeOH/CH$_2$Cl$_2$ 1:10). LCMS m/z 512 [M+H]$^+$. $^1$H-NMR (CDCl$_3$, rotamers 0.5:0.5) δ 7.10-6.81 (m, 6H), 6.59-6.49 (m, 2H), 4.65-4.55 (m, 0.5H, pip-H), 4.55-4.50 (m, 1H, dioxane-H), 4.50 and 4.43 (2s, 2H, benzyl-H), 4.10-4.02 (m, 2H, dioxane-H), 3.80-3.67 (m, 3.5H, pip-H, benzyl-H, dioxane-H) 3.45 (s, 1H, benzyl-H), 2.95-2.85 (m, 4H, pip-H, NHCH$_2$CH(CH$_3$)$_2$)), 2.45-2.35 (m, 2H, NCH$_2$), 2.09-1.99 (m, 2H, dioxane-H, pip-H), 1.91-1.50 (m, 7H, NCH$_2$CH$_2$, pip-H, NHCH$_2$CH(CH$_3$)$_2$), 1.38-1.25 (m, 2H, dioxane-H, pip-H), 0.98 (m, 6H, NHCH$_2$CH(CH$_3$)$_2$). HPLC t$_R$=8.2 min.

N-{1-[2-(1,3-Dioxan-2-yl)ethyl)piperidin-4-yl}-N-(4-fluorobenzyl)-2-(4-propylamino-phenyl)acetamide, L-tartrate (121JP28)

Prepared identically as described in the protocol for the synthesis of 121JP27, using propylamine (16 mg, 230 μmol)

instead of isobutylamine to afford 24 mg (25%) of 121JP28 as a thick oil. The L-tartrate salt was prepared as described above.

$R_f$=0.33 (MeOH/CH$_2$Cl$_2$ 1:10). LCMS m/z 498 [M+H]$^+$. $^1$H-NMR (CDCl$_3$, rotamers 0.5:0.5) δ 7.11-6.82 (m, 6H), 6.53-6.43 (m, 2H), 4.58-4.49 (m, 0.5H, pip-H), 4.48-4.45 (m, 1H, dioxane-H), 4.42 and 4.35 (2s, 2H, benzyl-H), 4.05-3.95 (m, 2H, dioxane-H), 3.70-3.60 (m, 3.5H, pip-H, benzyl-H, dioxane-H), 3.40 (s, 1H, benzyl-H), 3.05-2.95 (m, 2H, pip-H), 2.85-2.70 (m, 2H, NHCH$_2$CH$_2$CH$_3$), 2.48-2.38 (m, 2H, NCH$_2$), 2.05-1.90 (m, 2H, dioxane-H, pip-H), 1.92-1.40 (m, 8H, NCH$_2$CH$_2$, pip-H, NHCH$_2$CH$_2$CH$_3$), 1.40-1.28 (m, 2H, dioxane-H, pip-H), 0.98 (m, 3H, NHCH$_2$CH$_2$CH$_3$). HPLC $t_R$=7.3 min.

N-{1-[2-(1,3-Dioxan-2-yl)ethyl)piperidin-4-yl}-N-(4-fluorobenzyl)-2-(4-(1-nitropropyl)-phenyl)acetamide, L-tartrate (121JP34)

Adapting a protocol by Vogl & Buchwald (*J. Org. Chem.*, 2002, 67, 106-111), 121JP13 (135 mg, 0.26 mmol), 1-nitropropane (47 mg, 0.52 mmol), Cs$_2$CO$_3$ (95 mg, 0.29 mmol), 2-di-tert-butylphosphinobiphenyl (15.5 mg, 52 µmol) and Pd$_2$dba$_3$ (11.9 mg, 13 µmol) were weighed into a flask, DME (2 mL) was added and the reaction was stirred at 60° C. for 20 h. Workup as in 121JP13 followed by preparative TLC (CH$_2$Cl$_2$/MeOH, 15:1, 10× eluted) afforded 22 mg (16%) of 121JP34 as a thick colourless oil. The L-tartrate salt of the title compound was prepared as described above.

$R_f$=0.58 (MeOH/CH$_2$Cl$_2$ 1:10). LCMS m/z 528 [M+H]$^+$. HPLC $t_R$=8.1 min.

N-{1-[2-(1,3-Dioxan-2-yl)ethyl)piperidin-4-yl}-N-(4-fluorobenzyl)-2-[4-(2-oxopyrrolidin-1-yl)phenyl]acetamide, L-tartrate (121JP31)

Adapting a protocol by Yin & Buchwald (*J. Am. Chem. Soc.*, 2002, 124, 6043-6048), 121JP13 (124 mg, 0.24 mmol), pyrrolidone (24.7 mg, 0.29 mmol), Cs$_2$CO$_3$ (111 mg, 0.34 mmol), Xantphos (20.8 mg, 0.036 mmol) and Pd$_2$dba$_3$ (11.0 mg, 0.012 mmol) were weighed into a flask, dioxane (2 mL) was added and the reaction was stirred at 90° C. for 70 h. Workup as in 121JP13 and purification as in 121JP27 afforded 8 mg (7%) of 121JP31 as a thick colourless oil. The L-tartrate salt was prepared as described above.

$R_f$=0.31 (MeOH/CH$_2$Cl$_2$ 1:10). LCMS m/z 524 [M+H]$^+$. $^1$H-NMR (CDCl$_3$, rotamers 0.6:0.4) δ 7.60-6.80 (m, 8H), 4.60-4.50 (m, 0.4H, pip-H), 4.47 (t, 1H, J=5.1, dioxane-H) 4.42 and 4.38 (2s, 2H, benzyl-H), 4.04-3.97 (m, 2H, dioxane-H), 3.82-3.60 (m, 5.4H, pip-H, dioxane-H, benzyl-H, pyrrol-H), 3.25 (s, 1.2H, benzyl-H), 2.90-2.72 (m, 2H, pip-H), 2.60-2.50 (m, 2H, pyrrol-H), 2.39-2.32 (m, 2H, NCH$_2$) 2.18-1.90 (m, 4.2 H, dioxane-H, pip-H, pyrrol-H), 1.81-1.40 (m, 6H, pip-H, NCH$_2$CH$_2$), 1.32-1.18 (m, 1.8H, dioxane-H, pip-H). HPLC $t_R$=4.9 min.

N-{1-[2-(1,3-Dioxan-2-yl)ethyl)piperidin-4-yl}-N-(4-fluorobenzyl)-2-(4-isobutylsulfanyl-phenyl)acetamide, L-tartrate (121JP33)

Adapting a protocol by Li (*J. Org. Chem.*, 2002, 67, 3643-3650), 121JP13 (120 mg, 0.231 mmol), 2-methyl-1-propanethiol (25 mg, 0.28 mmol), [(t-Bu)$_2$P(OH)]$_2$PdCl$_2$ (11.6 mg, 0.0231 mmol) and NaOtBu (44 mg, 0.46 mmol) were weighed into a flask, toluene (2 mL) was added and the reaction was stirred at 110° C. for 16 h. Workup as in 121JP13 and purification as in 121JP27 afforded 1.7 mg (1.4%) of 121JP33 as a thick colourless oil. The L-tartrate salt of the title compound was prepared as described above.

$R_f$=0.46 (MeOH/CH$_2$Cl$_2$ 1:10). LCMS m/z 529 [M+H]$^+$. $^1$H-NMR (CDCl$_3$, rotamers 0.6:0.4) δ 7.24-6.82 (m, 8H), 4.57-4.48 (m, 0.4H, pip-H), 4.47 (t, 1H, J=5.1, dioxane-H), 4.45 and 4.38 (2s, 2H, benzyl-H), 4.05-3.95 (m, 2H, dioxane-H), 3.72 (s, 0.8 H, benzyl-H), 3.70-3.60 (m, 2.6H, pip-H, dioxane-H) 3.44 (s, 1.2H, benzyl-H), 2.87-2.75 (m, 2H, pip-H), 2.72 (t, 2H, J=6.5, SCH$_2$CH(CH$_3$)$_2$)), 2.38-2.28 (m, 2H, NCH$_2$), 2.05-1.88 (m, 2.2H, dioxane-H, pip-H), 1.81-1.48 (m, 7H, NCH$_2$CH$_2$, pip-H, SCH$_2$CH(CH$_3$)$_2$), 1.30-1.20 (m, 1.8H, dioxane-H, pip-H), 0.98 (t, 6H, J=6.7, SCH$_2$CH(CH$_3$)$_2$). HPLC $t_R$=8.8 min.

N-{1-[2-(1,3-Dioxan-2-yl)ethyl)piperidin-4-yl}-N-(4-fluorobenzyl)-2-(4-iodophenyl)-acetamide, L-tartrate (121JP40)

The title compound was prepared by the procedure described above 117NLS87-A using 118AF52-95 (400 mg, 1.24 mmol) and 4-iodophenylacetic acid (1.22 g, 4.64 mmol). Workup as in 121JP13 and purification as in 121JP34 gave 320 mg (46%) of 121JP40 as a colourless thick oil. The L-tartrate salt was prepared as described above.

$R_f$=0.52 (MeOH/CH$_2$Cl$_2$ 1:10). LCMS m/z 567 [M+H]$^+$. $^1$H-NMR (CDCl$_3$, rotamers 0.6:0.4) δ 7.65-7.55 (m, 2H), 7.16-6.85 (m, 6H), 4.59-4.50 (m, 0.6H, pip-H), 4.51 (t, 1H, J=5.0, dioxane-H), 4.50 and 4.42 (2s, 2H, benzyl-H), 4.09-4.00 (m, 2H, dioxane-H), 3.75 and 3.49 (2s, 2H, benzyl-H), 3.74-3.54 (m, 2.4 H, pip-H, dioxane-H), 2.85 (d, 2H, J=10.6, pip-H), 2.41-2.35 (m, 2H, NCH$_2$), 2.08-1.95 (m, 2.2H, dioxane-H, pip-H), 1.88-1.50 (m, 6H, pip-H, NCH$_2$CH$_2$), 1.39-1.27 (m, 1.8H, dioxane-H, pip-H). HPLC $t_R$=8.6 min.

2-(4-Acetophenyl)-N-{1-[2-(1,3-dioxan-2-yl)ethyl)piperidin-4-yl}-N-(4-fluorobenzyl)-acetamide, L-tartrate (121JP44)

Adapting a protocol by Cacchi et al (*Org. Lett*, 2003, 5, 289-293), 121JP40 (68 mg, 0.12 mmol), acetic anhydride (61 mg, 0.6 mmol), Pd$_2$dba$_3$ (1.4 mg, 1.5 µmol), lithium chloride (26 mg, 0.6 mmol) and EtNiPr$_2$ (31 mg, 0.24 mmol) were weighed into a flask, DMF (0.9 mL) was added and the resulting mixture was stirred at 100° C. for 18 h. Workup as in 121JP13 and purification as in 121JP34 afforded 19 mg (33%) of 121JP44 as a thick colourless oil. The L-tartrate salt was prepared as described above.

$R_f$=0.50 (MeOH/CH$_2$Cl$_2$ 1:10). LCMS m/z 483 [M+H]$^+$. $^1$H-NMR (CDCl$_3$, rotamers 0.6:0.4) 7.88-7.78 (m, 2H), 7.36-6.84 (m, 6H), 4.58-4.49 (m, 0.4H, pip-H), 4.48-4.46 (m, 1H, dioxane-H), 4.45 and 4.38 (2s, 2H, benzyl-H), 4.05-3.95 (m, 2H, dioxane-H), 3.81 and 3.55 (2s, 2H, benzyl-H), 3.70-3.60 (m, 2.6H, pip-H, dioxane-H) 2.85-2.75 (m, 2H, pip-H), 2.54 and 2.52 (2s, 3H, CH$_3$), 2.38-2.27 (m, 2H, NCH$_2$), 2.05-1.92 (m, 2.2H, dioxane-H, pip-H), 1.81-1.45 (m, 6H, NCH$_2$CH$_2$, pip-H), 1.32-1.22 (m, 1.8H, dioxane-H, pip-H). HPLC $t_R$=5.5 min.

2-[4-(1-Hydroxyiminoethyl)phenyl]-N-{1-[2-(1,3-dioxan-2-yl)ethyl)piperidin-4-yl}-N-(4-fluorobenzyl)acetamide, L-tartrate (121JP48)

121JP44 (14 mg, 29 µmol), pyridine (4.6 mg, 58 µmol) and ethanol (5 mL) were placed in a flask, to which hydroxylamine hydrochloride (4.1 mg, 58 µmol) was added and the resulting mixture was stirred at rt for 5 h. Workup as in 121JP13 and purification as in 121JP34 afforded 7 mg (49%) of 121JP48 as a thick colourless oil. The L-tartrate salt was prepared as described above.

$R_f$=0.40 (MeOH/CH$_2$Cl$_2$ 1:10). LCMS m/z 498 [M+H]$^+$. $^1$H-NMR (CDCl$_3$, rotamers 0.6:0.4) 7.63-7.51 (m, 2H), 7.33-6.88 (m, 6H), 4.66-4.58 (m, 0.4H, pip-H), 4.56-4.53 (m, 1H, dioxane-H), 4.51 and 4.40 (2s, 2H, benzyl-H), 4.10-4.04 (m, 2H, dioxane-H), 3.85 and 3.58 (2s, 2H, benzyl-H), 3.78-3.67 (m, 2.6H, pip-H, dioxane-H) 2.97-2.83 (m, 2H, pip-H), 2.47-2.37 (m, 2H, NCH$_2$), 2.26 and 2.24 (2s, 3H, CH$_3$), 2.12-1.98 (m, 2.2H, dioxane-H, pip-H), 1.88-1.58 (m, 6H, NCH$_2$CH$_2$, pip-H), 1.37-1.29 (m, 1.8H, dioxane-H, pip-H). HPLC $t_R$=4.0 min.

N-{1-[2-(1,3-Dioxan-2-yl)ethyl)piperidin-4-yl}-N-(4-fluorobenzyl)-2-(4-morpholin-4-yl-phenyl)acetamide, L-tartrate (121JP49)

Adapting a protocol by Buchwald et al (*Org. Lett.*, 2002, 4, 581-584), 121JP40 (50 mg, 88 µmol), morpholine (9.2 mg, 106 µmol), CuI (1.7 mg, 8.8 µmol) and K$_3$PO$_4$ (37.6 mg, 177 µmol) were weighed into a flask in air atmosphere, ethylene glycol (2 mL) was added and the resulting mixture was stirred at 80° C. for 16 h under air atmosphere. Workup as in 121JP13 and purification as in 121JP34 afforded 4.7 mg (10%) of 121JP49 as a thick colourless oil. The L-tartrate salt was prepared as described above.

$R_f$=0.33 (MeOH/CH$_2$Cl$_2$ 1:10). LCMS m/z 526 [M+H]$^+$. $^1$H-NMR (CDCl$_3$, rotamers 0.6:0.4) δ 7.18-6.72 (m, 8H), 4.62 and 4.37 (2s, 2H, benzyl-H), 4.57-4.50 (m, 0.4H, pip-H), 4.50-4.42 (m, 1H, dioxane-H), 4.05-3.95 (m, 2H, dioxane-H), 3.82-3.75 (m, 4H, morph-H), 3.69 and 3.43 (2s, 2H, benzyl-H), 3.68-3.61 (m, 2.6H, pip-H, dioxane-H), 3.12-3.03 (m, 4H, morph-H), 2.85-2.75 (m, 2H, pip-H), 2.38-2.27 (m, 2H, NCH$_2$), 2.07-1.90 (m, 2.2H, dioxane-H, pip-H), 1.82-1.45 (m, 6H, NCH$_2$CH$_2$, pip-H), 1.30-1.22 (m, 1.8H, dioxane-H, pip-H). HPLC $t_R$=6.2 min.

N-{1-[2-(1,3-Dioxan-2-yl)ethyl)piperidin-4-yl}-N-(4-fluorobenzyl)-2-(4-pyrazol-1-yl-phenyl)acetamide, L-tartrate (121JP56)

Adapting a protocol by Buchwald et al (*J. Am. Chem. Soc.*, 2001, 123, 7727-7729), 121JP40 (48 mg, 85 µmol), pyrazole (7 mg, 102 µmol), CuI (0.4 mg, 1.7 µmol), racemic trans-1,2-cyclohexanediamine (1.0 mg, 8.5 µmol), and K$_2$CO$_3$ (25 mg, 181 µmol) were weighed into a flask, dioxane (1.5 mL) was added and the resulting mixture was stirred at 110° C. for 60 h. Workup as in 121JP13 and purification as in 121JP34 afforded 3.9 mg (9%) of 121JP56 as a thick colourless oil. The L-tartrate salt was prepared as described above.

$R_f$=0.27 (MeOH/CH$_2$Cl$_2$ 1:10). LCMS m/z 507 [M+H]$^+$. $^1$H-NMR (CDCl$_3$, rotamers 0.6:0.4) δ 7.86 and 7.82 (2d, 1H, J=2.2, pyraz-H), 7.64 (d, 1H, J=4.4, pyraz-H), 7.62-6.83 (m, 8H), 6.42-6.36 (m, 1H, pyraz-H), 4.60-4.49 (m, 0.6H, pip-H), 4.48 (t, 1H, J=5.1, dioxane-H), 4.45 and 4.38 (2s, 2H, benzyl-H), 4.05-3.95 (m, 2H, dioxane-H), 3.80 and 3.54 (2s, 2H, benzyl-H), 3.70-3.61 (m, 2.4H, pip-H, dioxane-H) 2.85-2.75 (m, 2H, pip-H), 2.38-2.28 (m, 2H, NCH$_2$), 2.07-1.90 (m, 2.2H, dioxane-H, pip-H), 1.82-1.45 (m, 6H, NCH$_2$CH$_2$, pip-H), 1.35-1.22 (m, 1.8H, dioxane-H, pip-H). HPLC $t_R$=6.4 min.

2-(2-Bromopropyl)-1,3-dioxane (121JP80)

Adapting a procedure of Büchi and Wüest (*J. Org. Chem*, 1969, 34, 1122-1123), crotonaldehyde (3 g, 43 mmol) was added dropwise to conc. aq. HBr (5.2 g, 64 mmol) over 5 min at 5° C. under air atmosphere. After 15 min of stirring at 5° C., during which time the mixture changed from colourless to brownish, 1,3-propanediol (8.1 g, 107 mmol) was added and the reaction was stirred at 5° C. for further 0.5 h before allowing it warm to rt, and finally stirring it at rt for 2 h. The crude reaction mixture was then n-heptane extracted (2×200 mL), the combined n-heptane extracts were Na$_2$SO$_4$ dried, evaporated in vacuo and 121JP80 was isolated by Kugelrohr distillation (75° C., 0.18 mmHg) to obtain 124 mg (1.4%) of the title compound as a colourless liquid.

Characterization Data: $^1$H-NMR (CDCl$_3$) δ 4.73 (dd, 1H, J=7.2, 3.4), 4.26-4.18 (m, 1H), 4.15-4.06 (m, 2H), 3.83-3.75 (m, 2H), 2.15-1.97 (m, 3H), 1.71 (d, 3H, J=6.6), 1.38-1.32 (m, 1H).

N-{1-[2-(1,3-Dioxan-2-yl)-1-methylethyl]piperidin-4-yl}-N-(4-fluorobenzyl)-2-(4-iso-butoxyphenyl)-acetamide, L-tartrate (121JP84)

The title compound was prepared by the procedure described above 103NLS63-F using 103NLS56 (202 mg, 0.51 mmol) and 121JP80 (124 mg, 0.59 mmol) as the alkylating agent. Workup as in 121JP13 and purification as in 121JP34 gave 1.9 mg (0.7%) of 121JP84 as a thick oil. The L-tartrate salt was prepared as described above.

$R_f$=0.43 (MeOH/CH$_2$Cl$_2$ 1:10). LCMS m/z 527 [M+H]$^+$. $^1$H-NMR (CDCl$_3$, rotamers 0.5:0.5) δ 7.19-6.80 (m, 8H), 4.50-4.33 (m, 3.5H, dioxane-H, benzyl-H, pip-H), 4.04-3.93 (m, 2H, dioxane-H), 3.72-3.55 (m, 5.5H, dioxane-H, benzyl-H, pip-H, OCH$_{2OiBu}$), 3.42 (s, 1H, benzyl-H), 2.78-2.59 (m, 2H, pip-H), 2.34-2.16 (m, 1H, NCH), 2.08-1.89 (m, 2H, pip-H, CH$_{OiBu}$), 1.79-0.77 (m, 177H, CH$_{3OiBu}$, NCHCH$_3$, NCHCH$_2$, pip-H, dioxane-H). HPLC $t_R$=8.5 min.

4-Iodophenylacetic acid ethyl ester (121JP58)

4-Iodophenylacetic acid (3 g), ethanol (20 mL) and conc. H$_2$SO$_4$ (5 mL) were refluxed overnight. Ca. 15 mL ethanol was then evaporated, the residue was extracted with dichloromethane (3×100 mL), the combined organic extracts were washed with sat. aq. NaHCO$_3$, dried over Na$_2$SO$_4$ and evaporated in vacuo to afford 2.97 g (90%) of 121JP58 as a yellow oil.

Characterization Data: $^1$H-NMR (CDCl$_3$) δ 7.62 (d, 2H, J=8.4), 7.02 (d, 2H, J=8.4), 4.07 (q, 2 H, J=7.0), 3.59 (s, 2H), 1.12 (t, 3H, J=7.0).

4-Pyrazol-1-ylphenylacetic acid ethyl ester (121JP64)

121JP58 (290 mg, 1.0 mmol) was treated identically as 121JP40 for the synthesis of 121JP56. After heating the reaction to 110° C. for 72 h and workup as in 121JP13, the crude mixture was purified by VFC (CH$_2$Cl$_2$/MeOH 1:0→20:1) to furnish 180 mg (78%) of 121JP64 as a yellow oil.

Characterization Data: $^1$H-NMR (CDCl$_3$) δ 7.92 (dd, 1H, J=2.3, 1.0), 7.72 (d, 1H, J=1.3), 7.62 (d, 2H, J=8.7), 7.39 (d, 2H, J=8.7), 6.42 (dd, 1H, J=2.5, 1.9), 4.18 (q, 2 H, J=7.0), 3.61 (s, 2H), 1.22 (t, 3H, J=7.1).

4-Pyrazol-1-ylphenylacetic acid (121JP68, 87)

121JP64 (180 mg, 0.78 mmol), lithium hydroxide monohydrate (164 mg, 3.9 mmol), H$_2$O (10 mL) and THF (10 mL) were stirred overnight at rt. The crude mixture was then extracted with dichloromethane (3×150 mL), the pH of the aqueous phase was adjusted to ca. pH 3 using 4M HCl and extracted with dichloromethane (3×150 mL). The combined organic layers were dried over Na$_2$SO$_4$, filtered and evaporated in vacuo to provide 128 mg (81%) of 121JP68 as a yellow solid.

Characterization Data: $^1$H-NMR (CDCl$_3$) δ 7.90 (m, 1H), 7.75 (m, 1H), 7.63 (d, 2H, J=8.6), 7.38 (d, 2H, J=8.6), 6.45 (m, 1H), 3.68 (s, 2H).

N-{1-[2-(1,3-Dioxan-4-yl)ethyl]piperidin-4-yl}-N-(4-fluorobenzyl)-2-(4-pyrazol-1-yl-phenyl)acetamide, L-tartrate (121JP91)

The title compound was prepared by the general procedure described above 117NLS87-A using 128NLS52 (87 mg, 0.27 mmol) and 121JP87 (60 mg, 0.27 mmol). Workup as in 121JP13 and purification as in 121JP34 gave 25 mg (18%) of 121JP91 as a colourless oil. The L-tartrate salt was prepared as described above.

R$_f$=0.34 (MeOH/CH$_2$Cl$_2$ 1:10). LCMS m/z 507 [M+H]$^+$. $^1$H-NMR (CDCl$_3$, rotamers 0.5:0.5) δ 7.92 and 7.88 (2d, 1H, J=2.2, pyraz-H), 7.71 (d, 1H, J=4.7, pyraz-H), 7.69-6.90 (m, 8H), 6.48-6.42 (m, 1H, pyraz-H), 5.00 (d, 1H, J=6.3, dioxane-H), 4.65 (d, 1H, J=6.4, dioxane-H), 4.63-4.55 (m, 0.5H, pip-H), 4.52 and 4.46 (2s, 2H, benzyl-H), 4.10-4.02 (m, 1H, dioxane-H), 3.86 and 3.57 (2s, 2H, benzyl-H), 3.78-3.55 (m, 2.5H, pip-H, dioxane-H) 2.93-2.82 (m, 2H, pip-H), 2.49-2.30 (m, 2H, NCH$_2$), 2.10-1.98 (m, 1H, pip-H), 1.90-1.33 (m, 9H, NCH$_2$CH$_2$, pip-H, dioxane-H). HPLC t$_R$=5.2 min.

N-[1-((R)-3,5-Dihydroxypentyl)piperidine-4-yl]-N-(4-fluorobenzyl)-2-(4-isobutoxyphenyl)acetamide, tartrate (130AF93-189)

The desired compound was synthesized from (S)-5-[(4-methylbenzenesulfonyl)oxy]pentane-1,3-diol (Moune et al, J. Org. Chem., 1997, 62, 3332-3339) and 103NLS56 using the same method as described for the preparation of 130AF65-182.

R$_f$=0.48 (MeOH/CH$_2$Cl$_2$, 10:90). LCMS m/z 501 [M+H]$^+$. HPLC t$_R$=7.4 min.

N-{1-[2-((4R)-1,3-Dioxane-4-yl)ethyl]piperidine-4-yl}-N-(4-fluorobenzyl)-2-(4-isobutoxyphenyl)acetamide, tartrate (130AF95-190)

The desired compound (7.9 mg, 55%) was synthesized from 130AF93-189 (18.6 mg, 0.028 mmol) using the same method as for the synthesis of 130AF67-183. The enantiomeric excess was determined to be 99% using chiral HPLC analysis (Chiralpak AD column, 4.6×250 mm; heptane/I—PrOH 50:50, 0.3% DEA; 0.5 mL/min; t$_R$ 22.7 min). The $^1$H NMR and LCMS data were identical with 130AF67-183.

4-(1,2,4-Triazol-4-yl)phenylacetic acid (141JP01)

Adapting a protocol by Catarzi et al (J. Med Chem., 2001, 44, 3157-3165), diformylhydrazine (352 mg, 4.0 mmol) and then dropwise trimethylsilyl chloride (2.53 mL, 20 mmol) and Et$_3$N (1.30 mL, 9.3 mmol) were added to a suspension of 4-aminophenylacetic acid (201 mg, 1.33 mmol) in anhydrous pyridine. The mixture was heated at 100° C. overnight, volatiles were removed at reduced pressure and the resulting solid was treated with water (6 mL), collected, washed with H$_2$O and dried in vacuo to provide 251 mg (93%) of 141JP01 as a light brown solid. LCMS m/z 204[M+H]$^+$. $^1$H-NMR (DMSO-d$_6$) δ 9.05 (s, 2H), 7.62 (d, 1H, J=8.6), 7.40 (d, 1H, J=8.2), 3.61 (s, 2H).

N-{1-[2-(1,3-Dioxan-2-yl)ethyl]piperidin-4-yl}-N-(4-fluorobenzyl)-2-[4(1,2,4-triazol-4-yl)phenyl]acetamide, L-tartrate (141JP13)

The acid 141JP01 (35 mg, 0.17 mmol), N-{1-[2-(1,3-dioxan-2-yl)ethyl]piperidin-4-yl}-N-(4-fluorobenzyl)amine (118AF52-95, 55 mg, 0.17 mmol) and diisopropylethylamine (52 mg, 0.51 mmol) were dissolved in DMF (5 mL). Bromo-tris-pyrrolidino-phosphonium hexafluorophosphate (PyBroP, 119 mg, 0.25 mmol) was added, and the mixture was stirred at rt for 2 h. The mixture was concentrated and passed onto an acidic ion exchange SPE cartridge. The cartridge was washed with methanol (8×4 mL) and the remaining product was eluted off the column with 10% NH$_4$OH in methanol (2×4 mL) and evaporated. The resulting oil was purified as in 121JP34 to give 47 mg (54%) of 141JP13 as a colourless oil. The L-tartrate salt was prepared as described above.

R$_f$=0.26 (MeOH/CH$_2$Cl$_2$ 1:10). LCMS m/z 508[M+H]$^+$. $^1$H-NMR (CDCl$_3$, rotamers 0.5:0.5) δ 8.47 and 8.41 (2s, 1H, -H), 7.48-6.89 (m, 8H, Ar—H), 4.62-4.56 (m, 0.6H, pip-H), 4.56-4.49 (m, 3H, dioxane-H, benzyl-H), 4.10-4.01 (m, 2H, dioxane-H), 3.79 and 3.61 (2s, 2H, benzyl-H), 3.77-3.67 (m, 2.4H, pip-H, dioxane-H), 2.94-2.84 (m, 2H, pip-H), 2.45-2.35 (m, 2H, NCH$_2$), 2.10-1.43 (m, 9H, dioxane-H, NCH$_2$CH$_2$, pip-H), 1.37-1.27 (m, 1 H, dioxane-H).

In vitro Determination of Receptor Activity

Receptor Selection and Amplification (R-SAT) Assays. The functional receptor assay, Receptor Selection and Amplification Technology (R-SAT™), was used (with minor modifications from the procedure described previously (Brann, M. R. U.S. Pat. No. 5,707,798, 1998; Chem. Abstr. 1998, 128, 111548) to screen compounds for efficacy at the 5-HT$_{2A}$ receptor. Briefly, NIH3T3 cells were grown in 96 well tissue culture plates to 70-80% confluence. Cells were transfected for 12-16 h with plasmid DNAs using superfect (Qiagen Inc.) as per manufacturer's protocols. R-SAT's were generally performed with 50 ng/well of receptor and 20 ng/well of β-galactosidase plasmid DNA. All receptor and G-protein constructs used were in the pSI mammalian expression vector (Promega Inc) as described previously. The 5-HT$_{2A}$ receptor gene was amplified by nested PCR from brain cDNA using the oligodeoxynucleotides based on the published sequence (Saltzman et. al, Biochem. Biophys. Res. Comm. 1991, 181, 1469). For large-scale transfections, cells were transfected for 12-16 h, then trypsinized and frozen in DMSO. Frozen cells were later thawed, plated at 10,000-40,000 cells per well of a 96 well plate that contained drug. With both methods, cells were then grown in a humidified atmosphere with 5% ambient CO$_2$ for five days. Media was then removed from the plates and marker gene activity was measured by the addition of the β-galactosidase substrate o-nitrophenyl β-D-galactopyranoside (ONPG, in PBS with 5% NP-40). The resulting colorimetric reaction was measured in a spectrophotometric plate reader (Titertek Inc.) at 420 nM. All data were analyzed using the computer program XLFit (IDBSm). Efficacy is the percent maximal repression compared to repression by a control compound (ritanserin in the case of 5-HT$_{2A}$). pIC$_{50}$ is the negative of the log(IC$_{50}$), where IC$_{50}$ is the calculated concentration in Molar that produces 50% maximal repression.

In vivo Determination of Behavioral Effects

Animals and Apparatus. Male NSA mice (Harlan; San Deigo, Calif.) were used as subjects. Mice weighed 20-30 g. Animals were housed 8/cage in the One Cage system (One Cage; Lab Products, Inc., Seaford, Del.) with bedding (⅛ inch Bed "O" Cob; Harlan Teklad, Madison, Wis.) in a room with controlled temperature 22±3° C. and a 12 hour light:dark cycle (lights on 6 am). Water and standard rodent chow (Harlan Teklad) were continuously available in the home cage. For testing, plastic locomotor activity cages (20×20×30 cm; AccuScan Instruments, Columbus, Ohio) were equipped with photocell beams for monitoring horizontal activity. Data were collected using Versamax computer software (AccuScan Instruments).

Procedure

For determination of spontaneous activity, test compounds were administered alone (s.c. 10 min or p.o. 30 min before the session). For hyperactivity experiments, mice were injected with 0.3 mg/kg MK-801 i.p. 15 min presession (the peak dose for producing hyperactivity in an inverted-U dose-effect curve as determined in pilot experiments) in combination with vehicle or test compound. Motor activity data were collected during a 15 min session in a lit room. Mice had no prior exposure to the motor cages. Each dose or dose combination was tested in a separate group of mice (n=8).

Data Analysis

Distance traveled (cm) was calculated and averaged across animals in a group. An analysis of variance (ANOVA) and post-hoc Dunnett's t-test comparions to vehicle control were conducted for each dose-response function. The lowest dose found to be significantly different from vehicle control was defined as the minimum effective dose (MED).

TABLE 1

|  |  | 5HT2A % INH | 5HT2A pIC50 | MED in vivo po (mg/kg) |
|---|---|---|---|---|
| 103NLS45-B | ClH | 84 | 7.6 | |

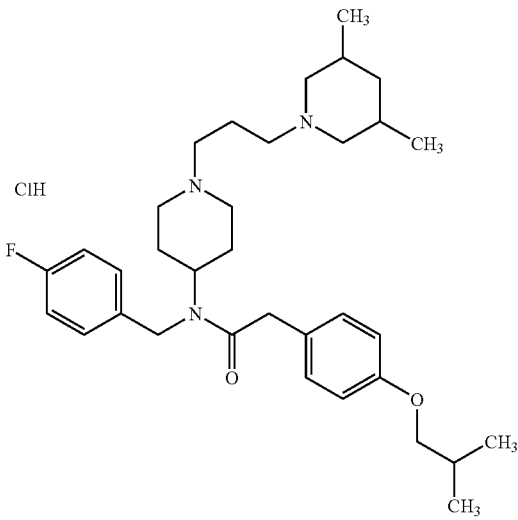

| 117NLS01 | | 104 | 9.7 | 1 |

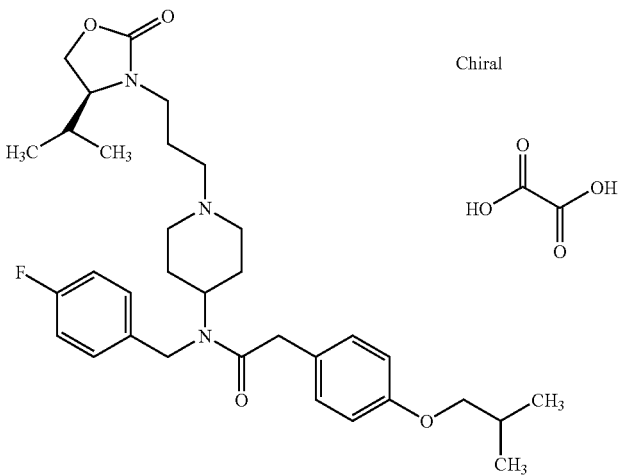

TABLE 1-continued
| | 5HT2A % INH | 5HT2A pIC50 | MED in vivo po (mg/kg) |
|---|---|---|---|
| 103NLS63-F 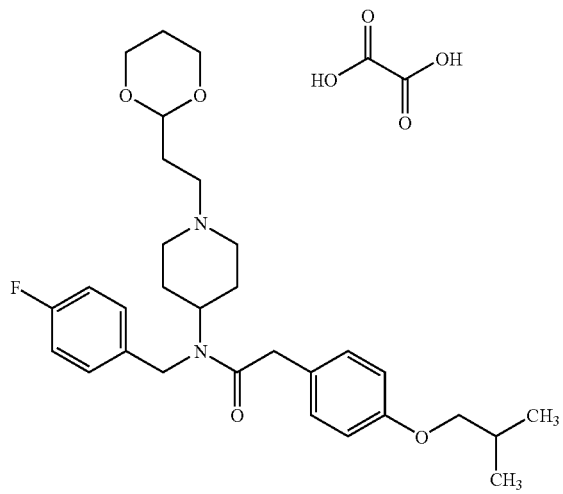 | 101 | 9.5 | |
| 103NLS69-A 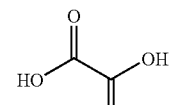 | 96 | 8.7 | |
| 117NLS03-B 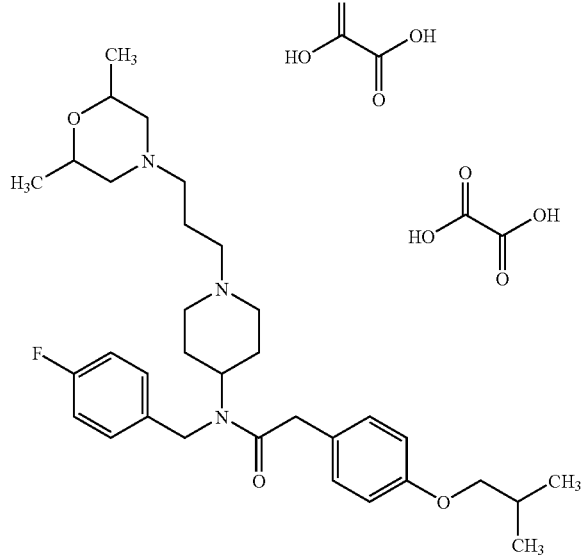 Chiral | 85 | 8.4 | |

TABLE 1-continued
| | 5HT2A % INH | 5HT2A pIC50 | MED in vivo po (mg/kg) |
|---|---|---|---|
| 117NLS25 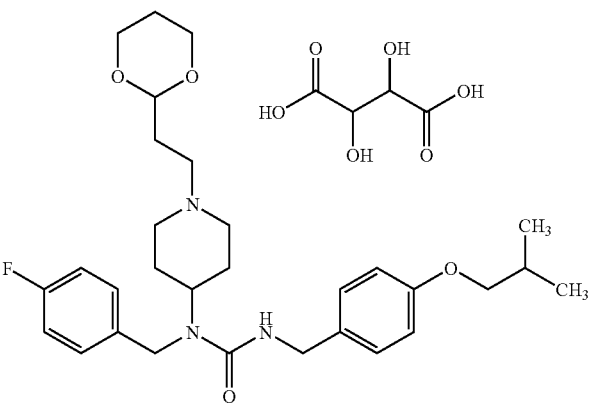 | 94 | 8.9 | |
| 128NLS22-A 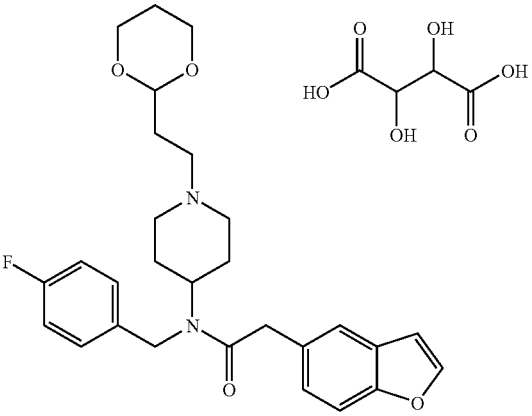 | 98 | 8.5 | |
| 118AF37-88 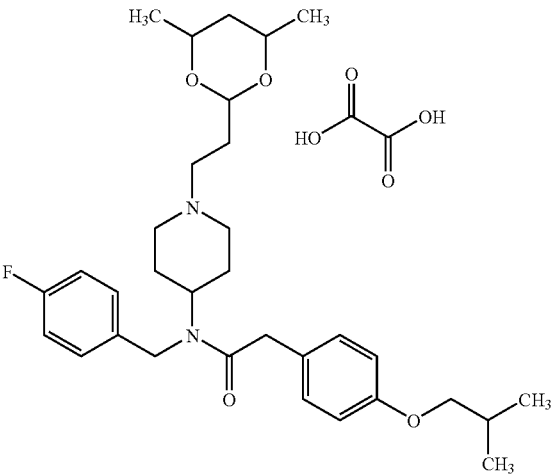 | 105 | 9.2 | |

TABLE 1-continued

| | 5HT2A % INH | 5HT2A pIC50 | MED in vivo po (mg/kg) |
|---|---|---|---|
| 098AF76-65 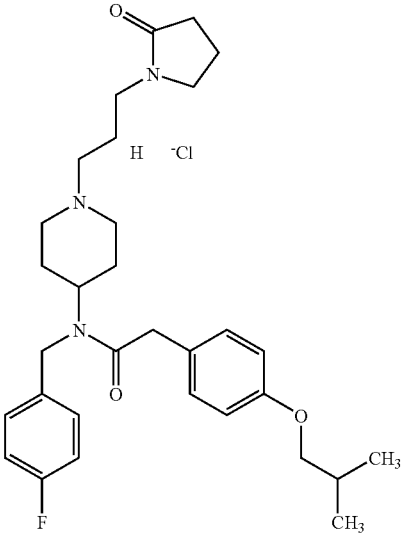 | 100 | 9.1 | |
| 118AF16-80 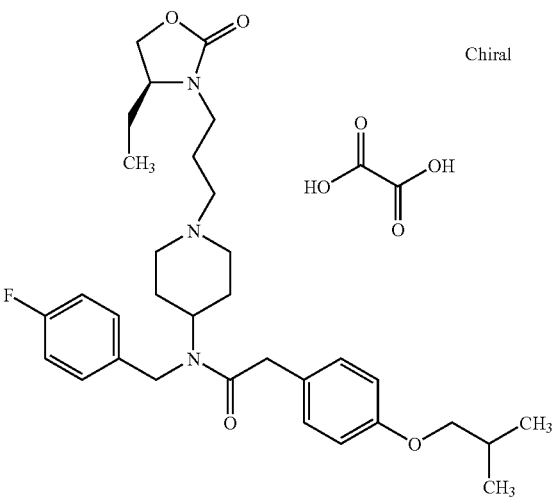 Chiral | 103 | 9.1 | |

What is claimed is:

1. A compound of Formula I

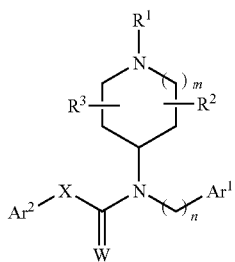

I or a pharmaceutically acceptable salt thereof, wherein
$R^1$ is an optionally substituted (heterocyclyl)$C_{1-6}$-alkyl;
$R^2$ and $R^3$ are independently selected from the group consisting of hydrogen, $C_{1-6}$-alkyl and halogen or such that $R^2$ together with $R^3$ forms a 3-, 4-, 5-, 6-, or 7-membered ring system with the atoms of the piperidine ring;
m is 1;
n is selected from the group consisting of 1, 2, and 3;
$Ar^1$ aryl or heteroaryl, optionally substituted with a substituent selected from the group consisting of $C_{1-6}$-alkyl, $C_{1-6}$-alkoxy, oxo, carboxyl, amino, hydroxy, nitro, alkylsulfonyl, alkylsulfenyl, alkylsulfinyl, $C_{1-6}$-alkoxycarbonyl, $C_{1-6}$-alkylcarbonyl, formyl, amino, mono- and di($C_{1-6}$-alkyl)amino, carbamoyl, mono- and di ($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, $C_{1-6}$-alkyl-hydroxyimino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, haloalkoxy, heterocyclyl, halo, alkylamido, $C_{1-6}$ hydroxyalkyl, $C_{1-6}$ aminoalkyl, and sulfamoyl;

W is selected from the group consisting of oxygen and sulfur;

X is selected from the group consisting of optionally substituted methylene, optionally substituted ethylene, optionally substituted propylene, optionally substituted vinylene, and CH$_2$N(R$^N$), wherein R$^N$ is selected from hydrogen and C$_{1-6}$-alkyl; and Ar$^2$ is an optionally substituted aryl or heteroaryl.

2. The compound of claim 1, wherein said (heterocyclyl) C$_{1-6}$-alkyl is optionally substituted with one or more groups selected from the group consisting of hydrogen, halogen, hydroxy, alkoxy, alkyl, and amino.

3. The compound of claim 1, wherein said heterocyclyl is selected from the group consisting of tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, benzimidazolidone, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-1,3-oxathiolane.

4. The compound of claim 1, wherein R$^1$ is selected from the group consisting of an optionally substituted (heterocyclyl)methyl, an optionally substituted (heterocyclyl)ethyl, or an optionally substituted (heterocyclyl)propyl.

5. The compound of claim 1, wherein R$^2$ and R$^3$ are hydrogen, m is 1, n is 1, and W is oxygen.

6. The compound of claim 1, wherein Ar$^1$ is an optionally substituted aryl, selected from the group consisting of alkyl-substituted phenyl, alkoxy-substituted phenyl, halogen-substituted phenyl, hydroxy-substituted phenyl and amino-substituted phenyl, wherein said alkyl is selected from the group consisting of methyl, ethyl, propyl, n-butyl, sec-butyl and tert-butyl, and said alkoxy is selected from the group consisting of methoxy, ethoxy, propxy, n-butoxy, sec-butoxy, and tert-butoxy.

7. The compound of claim 1, wherein Ar$^1$ is 4-substituted aryl.

8. The compound of claim 6, wherein Ar$^1$ is halogen-substituted phenyl.

9. The compound of claim 1, wherein X is selected from the group consisting of optionally substituted methylene and optionally substituted ethylene.

10. The compound of claim 1, wherein X is CH$_2$N(R$^N$).

11. The compound of claim 1, wherein Ar$^2$ is an aryl optionally substituted with a substituent selected from the group consisting of alkyl, alkoxy, halogen, hydroxy, amino, alkylamino, heteroaryl, and heterocyclyl.

12. The compound of claim 1, wherein Ar$^2$ is 4-substituted aryl.

13. The compound of claim 11, wherein said substituent on Ar$^2$ is selected from the group consisting of chloro, fluoro, hydroxy, methoxy, ethoxy, propoxy, isopropoxy, n-butoxy, sec-butoxy, tert-butoxy, trifluoromethoxy, N-morpholinyl, N-pyrrolidinyl, N-pyrazolyl, N-triazolyl and 2-oxopyrrolidinyl.

14. The compound of claim 1, wherein said compound is selected from the group consisting of:

N-{1-[2-(1,3-Dioxan-2-yl)ethyl]piperidin-4-yl}-N-(4-fluorobenzyl)-2-[4-(2-hydroxy-2-methylpropoxy)phenyl]acetamide;

N-{1-[3-(3,5-Dimethylpiperidin-1-yl)propyl]piperidin-4-yl}-N-(4-fluorobenzyl)-2-(4-isobutoxyphenyl)acetamide;

1-[3-(4-{(4-Fluorobenzyl)-[2-(4-isobutoxyphenyl)acetyl]amino}piperidin-1-yl)propyl]piperidine-4-carboxylic acid methyl ester;

N-(4-Fluorobenzyl)-2-(4-isobutoxyphenyl)-N-{1-[2-(1-methylpyrrolidin-2-yl)ethyl]piperidin-4-yl}acetamide;

N-{1-[3-(2,6-Dimethylmorpholin-4-yl)propyl]piperidin-4-yl}-N-(4-fluorobenzyl)-2-(4-isobutoxyphenyl)acetamide;

N-(4-Fluorobenzyl)-N-{1-[3-(3-hydroxypiperidin-1-yl)propyl]piperidin-4-yl}-2-(4-isobutoxyphenyl)acetamide,;

N-(4-Fluorobenzyl)-2-(4-isobutoxyphenyl)-N-{1-[3-(2-methylpiperidin-1-yl)propyl]piperidin-4-yl}acetamide;

N-(4-Fluorobenzyl)-2-(4-isobutoxyphenyl)-N-[1-(3-pyrrolidin-1-yl-propyl)piperidin-4-yl ]acetamide;

N-{1-[3-(2,5-Dimethylpyrrolidin-1-yl)propyl]piperidin-4-yl}-N-(4-fluorobenzyl)-2-(4-isobutoxyphenyl)acetamide;

N-(4-Fluorobenzyl)-N-{1-[3-(3-hydroxymethylpiperidin-1-yl)propyl]piperidin-4-yl}-2-(4-isobutoxyphenyl)acetamide;

N-(4-Fluorobenzyl)-2-(4-isobutoxyphenyl)-N-{1-[3-(4-(S)-isopropyl-2-oxo-oxazolidin-3-yl)propyl]piperidin-4-yl}acetamide;

N-[2-(4-Fluorophenyl)ethyl]-2-(4-isobutoxyphenyl)-N-{1-[3-(4-(S)-isopropyl-2-oxo-oxazolidin-3-yl)propyl]piperidin-4-yl}acetamide;

N-[2-(4-Fluorophenyl)ethyl]-N-{1-[3-(4-(S)-isopropyl-2-oxo-oxazolidin-3-yl)propyl]piperidin-4-yl}-2-(4-propoxyphenyl)acetamide;

N-(4-Fluorobenzyl)-N-{1-[3-(4-(S)-isopropyl-2-oxo-oxazolidin-3-yl)propyl]piperidin-4-yl}-2-(4-propoxyphenyl)acetamide;

N-{1-[2-(1,3-Dioxan-2-yl)ethyl]piperidin-4-yl}-N-(4-fluorobenzyl)-2-(4-isobutoxyphenyl)acetamide;

N-{1-[2-(1,3-Dioxan-2-yl)ethyl]piperidin-4-yl}-N-[2-(4-fluorophenyl)ethyl]-2-(4-isobutoxyphenyl)acetamide;

N-{1-[2-(1,3-Dioxan-2-yl)ethyl]piperidin-4-yl}-N-[2-(4-fluorophenyl)ethyl]-2-(4-propoxyphenyl)acetamide;

N-{1-[2-(1,3-Dioxan-2-yl)ethyl]piperidin-4-yl}-N-4-fluorobenzyl)-2-(4-propoxyphenyl)acetamide;

N-{1-[2-(1,3-Dioxan-2-yl)ethyl]piperidin-4-yl}-N-(4-fluorobenzyl)-2-(4-fluorophenyl)acetamide;

N-{1-[2-(1,3-Dioxan-2-yl)ethyl]piperidin-4-yl}-N-(4-fluorobenzyl)-2-p-tolylacetamide;

2-Benzofuran-5-yl-N-{1-[2-(1,3-dioxan-2-yl)ethyl]piperidin-4-yl}-N-(4-fluorobenzyl)acetamide;

N-{1-[2-(2,2-Dimethyl-1,3-dioxolan-4-yl)ethyl]piperidin-4-yl}-N-(4-fluorobenzyl)-2-(4-isobutoxyphenyl)acetamide;

N-{1-[2-(1,3-Dioxan-4-yl)ethyl]piperidin-4-yl}-N-(4-fluorobenzyl)-2-(4-isobutoxyphenyl)acetamide;

N-{1-[2-(1,3-Dioxan-4-yl)ethyl]piperidin-4-yl}-N-(4-fluorobenzyl)-2-(4-trifluoromethylphenyl)acetamide;

2-(4-Cyanophenyl)-N-{1-[2-(1,3-dioxan-4-yl)ethyl]piperidin-4-yl}-N-(4-fluorobenzyl)acetamide;

N-(4-Fluorobenzyl)-2-(4-isobutoxyphenyl)-N-{1-[2-(2-oxo-imidazolidin-1-yl)ethyl]piperidin-4-yl}acetamide;

N-(4-Fluorobenzyl)-2-(4-isopropoxyphenyl)-N-{1-[2-(2-oxo-imidazolidin-1-yl)ethyl]piperidin-4-yl}acetamide;

N-(4-Fluorobenzyl)-2-(4-isopropoxyphenyl)-N-{1-[3-(3-methyl-2-oxo-2,3-dihydro-benzoimidazol-1-yl)propyl]piperidin-4-yl}acetamide;

N-(4-Fluorobenzyl)-2-(4-isopropoxyphenyl)-N-{1-[4-(2-oxo-2,3-dihydrobenzoimidazol-1-yl)butyl]piperidin-4-yl}acetamide;
N-{1-[2-(2,4-Dioxo-1,4-dihydro-2H-quinazolin-3-yl)ethyl]piperidin-4-yl}-N-(4-fluorobenzyl)-2-(4-isopropoxyphenyl)acetamide;
N-{1-[2-(1,3-Dioxolan-2-yl)ethyl]piperidin-4-yl}-N-(4-fluorobenzyl)-2-(4-isobutoxyphenyl)acetamide;
N-{1-[2-(1,3-Dioxolan-2-yl)ethyl]piperidin-4-yl}-2-(4-isopropoxyphenyl)-N-(4-methylbenzyl)acetamide;
N-{1-[2-(1,3-Dioxolan-2-yl)ethyl]piperidin-4-yl}-N-(4-fluorobenzyl)-2-(4-propoxyphenyl)acetamide;
2-(4-Methoxyphenyl)-N-(4-methylbenzyl)-N-[1-(2-morpholin-4-ylethyl)piperidin-4-yl]acetamide;
2-(4-Methoxyphenyl)-N-(4-methylbenzyl)-N-[1-(3-morpholin-4-ylpropyl)piperidin-4-yl]acetamide;
N-(4-Fluorobenzyl)-2-(4-isobutoxyphenyl)-N-[1-(3-morpholin-4-ylpropyl)piperidin-4-yl]acetamide;
N-(4-Fluorobenzyl)-2-(4-isopropoxyphenyl)-N-[1-(3-morpholin-4-yl-propyl)piperidin-4-yl]acetamide;
N-{1-[2-(1,3-Dioxan-4-yl)ethyl]piperidin-4-yl}-N-(4-fluorobenzyl)-2-(4-fluorophenyl)acetamide;
N-{1-[2-(1,3-Dioxan-4-yl)ethyl]piperidin-4-yl}-N-(4-fluorobenzyl)-2-(4-trifluoromethoxyphenyl)acetamide;
N-{1-[2-(1,3-Dioxan-4-yl)ethyl]piperidin-4-yl}-N-(4-fluorobenzyl)-2-(4-propoxyphenyl)acetamide;
N-(4-Fluorobenzyl)-2-(4-isobutoxyphenyl)-N-[1-(tetrahydropyran-4-ylmethyl)piperidin-4-yl]acetamide;
N-(4-Fluorobenzyl)-2-(4-isobutoxyphenyl)-N-{1-[2-(tetrahydropyran-4-yl)ethyl]piperidin-4-yl]acetamide;
N-{1-[2-((4S)-1,3-Dioxane-4-yl)ethyl]piperidine-4-yl}-N-(4-fluorobenzyl)-2-(4-isobutoxyphenyl)acetamide;
N-{1-[2-(1,3-Dioxan-2-yl)ethyl]piperidin-4-yl}-N-(4-fluorobenzyl)-2-(4-hydroxyphenyl)-acetamide;
N-{1-[2-(1,3-Dioxan-2-yl)ethyl]piperidin-4-yl}-N-(4-fluorobenzyl)-2-(4-methoxyphenyl)-acetamide;
N-{1-[2-(1,3-Dioxan-2-yl)ethyl]piperidin-4-yl}-N-(4-fluorobenzyl)-2-(4-isopropylphenyl))-acetamide;
N-{1-[2-(1,3-Dioxan-2-yl)ethyl]piperidin-4-yl}-N-(4-fluorobenzyl)-2-(4-trifluoromethoxy-phenyl)acetamide;
N-{1-[2-(1,3-Dioxan-2-yl)ethyl]piperidin-4-yl}-N-(4-fluorobenzyl)-2-(4-isopropoxyphenyl)-acetamide;
N-{1-[2-(1,3-Dioxan-2-yl)ethyl]piperidin-4-yl}-N-(4-fluorobenzyl)-2-phenylacetamide;
N-{1-[2-(1,3-Dioxan-2-yl)ethyl]piperidin-4-yl}-N-(4-fluorobenzyl)-2-[4-(2-fluoroethoxy)-phenyl]acetamide;
N-{1-[2-(5,5-Dimethyl-1,3-dioxan-2-yl)ethyl]piperidin-4-yl}-N-(4-fluorobenzyl)-2-(4-isobutoxyphenyl)acetamide;
N-(4-Fluorobenzyl)-2-(4-isobutoxyphenyl)-N-{1-[2-((R)-4-methyl-1,3-dioxan-2-yl)ethyl]-piperidin-4-yl}acetamide;
N-(4-Fluorobenzyl)-2-(4-isobutoxyphenyl)-N-{1-[2-((S)-4-methyl-1,3-dioxolan-2-yl)ethyl]piperidin-4-yl}acetamide;
N-{1-[2-(4,6-Dimethyl-1,3-dioxan-2-yl)ethyl]piperidin-4-yl}-N-(4-fluorobenzyl)-2-(4-isobutoxyphenyl)acetamide;
N-(4-Fluorobenzyl)-N-{1-[2-((S)-4-methyl-1,3-dioxolan-2-yl)ethyl]piperidin-4-yl}-2-(4-trifluoromethoxyphenyl)acetamide;
N-(4-Fluorobenzyl)-2-(4-isopropylphenyl)-N-{1-[2-((S)-4-methyl-1,3-dioxolan-2-yl)ethyl]-piperidin-4-yl}acetamide;
N-(4-Fluorobenzyl)-N-{1-[2-((R)-4-methyl-1,3-dioxan-2-yl)ethyl]piperidin-4-yl}-2-(4-trifluoromethoxyphenyl)acetamide;
N-(4-Fluorobenzyl)-2-(4-isobutoxyphenyl)-N-{1-[2-(2,5,5-trimethyl-1,3-dioxan-2-yl)ethyl]piperidin-4-yl}acetamide;
N-(4-Fluorobenzyl)-2-(4-isobutoxyphenyl)-N-{1-[2-(2-methyl-1,3-dioxolan-2-yl)ethyl]-piperidin-4-yl}acetamide;
N-(4-Fluorobenzyl)-2-(4-isobutoxyphenyl)-N-{1-[3-(1,3-dioxolan-2-yl)propyl]piperidin-4-yl}acetamide;
N-(4-Fluorobenzyl)-2-(4-isobutoxyphenyl)-N-{1-(3-piperidin-1-yl-propyl)piperidin-4-yl)}-acetamide;
N-(4-Fluorobenzyl)-2-(4-isobutoxyphenyl)-N-{1-[3-(2-oxo-piperidin-1-yl)propyl]piperidin-4-yl}acetamide;
N-(4-Fluorobenzyl)-2-(4-isobutoxyphenyl)-N-{1-[3-(2-oxo-pyrrolidin-1-yl)propyl]piperidin-4-yl}acetamide;
N-(4-Fluorobenzyl)-2-(4-isobutoxyphenyl)-N-{1-[3-((R)-4-isopropyl-2-oxo-oxazolidin-3-yl)propyl]piperidin-4-yl}acetamide;
N-(4-Fluorobenzyl)-2-(4-isobutoxyphenyl)-N-{1-[3-(2-oxo-oxazolidin-3-yl)propyl]piperidin-4-yl}acetamide;
N-(4-Fluorobenzyl)-2-(4-isobutoxyphenyl)-N-{1-[3-((S)-4-methyl-2-oxo-oxazolidin-3-yl)propyl]piperidin-4-yl}acetamide;
N-(4-Fluorobenzyl)-2-(4-isobutoxyphenyl)-N-{1-[3-((S)-4-ethyl-2-oxo-oxazolidin-3-yl)-propyl]piperidin-4-yl}acetamide;
N-(4-Fluorobenzyl)-2-(4-isobutoxyphenyl)-N-{1-[2-(1,3-oxothiolan-2-yl)ethyl]piperidin-4-yl}acetamide;
2-(4-Bromophenyl)-N-{1-[2-(1,3-dioxan-2-yl)ethyl)piperidin-4-yl}-N-(4-fluorobenzyl)-acetamide;
N-{1-[2-(1,3-Dioxan-2-yl)ethyl)piperidin-4-yl}-N-(4-fluorobenzyl)-2-(4-isobutylamino-phenyl)acetamide;
N-{1-[2-(1,3-Dioxan-2-yl)ethyl)piperidin-4-yl}-N-(4-fluorobenzyl)-2-(4-propylamino-phenyl)acetamide;
N-{1-[2-(1,3-Dioxan-2-yl)ethyl)piperidin-4-yl}-N-(4-fluorobenzyl)-2-(4-(1-nitropropyl)-phenyl)acetamide;
N-{1-[2-(1,3-Dioxan-2-yl)ethyl)piperidin-4-yl}-N-(4-fluorobenzyl)-2-[4-(2-oxopyrrolidin-1-yl)phenyl]acetamide;
N-{1-[2-(1,3-Dioxan-2-yl)ethyl)piperidin-4-yl}-N-(4-fluorobenzyl)-2-(4-isobutylsulfanyl-phenyl)acetamide;
N-{1-[2-(1,3-Dioxan-2-yl)ethyl)piperidin-4-yl}-N-(4-fluorobenzyl)-2-(4-iodophenyl)-acetamide;
2-(4-Acetophenyl)-N-{1-[2-(1,3-dioxan-2-yl)ethyl)piperidin-4-yl}-N-(4-fluorobenzyl)acetamide;
2-[4-(1-Hydroxyiminoethyl)phenyl]-N-{1-[2-(1,3-dioxan-2-yl)ethyl)piperidin-4-yl}-N-(4-fluorobenzyl)acetamide;
N-{1-[2-(1,3-Dioxan-2-yl)ethyl)piperidin-4-yl}-N-(4-fluorobenzyl)-2-(4-morpholin-4-yl-phenyl)acetamide;
N-{1-[2-(1,3-Dioxan-2-yl)ethyl)piperidin-4-yl}-N-(4-fluorobenzyl)-2-(4-(pyrazol-1-y)phenyl)acetamide;
N-{1-[2-(1,3-Dioxan-2-yl)-1-methylethyl]piperidin-4-yl}-N-(4-fluorobenzyl)-2-(4-isobutoxyphenyl)-acetamide;
N-{1-[2-(1,3-Dioxan-4-yl)ethyl)piperidin-4-yl}-N-(4-fluorobenzyl)-2-(4-pyrazol-1-ylphenyl)acetamide;
N-{1-[2-((4R)-1,3-Dioxane-4-yl)ethyl]piperidine-4-yl}-N-(4-fluorobenzyl)-2-(4-isobutoxyphenyl)acetamide; and
N-{1-[2-(1,3-Dioxan-2-yl)ethyl)piperidin-4-yl}-N-(4-fluorobenzyl)-2-[4-(1,2,4-triazol-4-yl)phenyl]acetamide.

15. The compound of claim 1, wherein the (heterocyclyl) $C_{1-6}$-alkyl is optionally substituted with one or more substituents selected from the group consisting of $C_{1-6}$-alkyl, $C_{1-6}$-alkoxy, oxo, carboxyl, amino, hydroxy, nitro, alkylsulfonyl, alkylsulfenyl, alkylsulfinyl, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, $C_{1-6}$-alkylhydroxyimino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, heterocyclyl, heteroaryl, halo, alkylamido, $C_{1-6}$ hydroxyalkyl, $C_{1-6}$ aminoalkyl, and sulfamoyl.

16. The compound of claim 1, wherein said heterocyclyl is selected from the group consisting of tetrahydrothiopyran, 4H-pyran, 1,3-dioxin, 1,3-dioxane, 1,4-dioxin, 1,4-dioxane, 1,3-oxathiane, 1,4-oxathin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, tetrahydrothiophene, imidazolidine, 1,3-dioxole, 1,3-dioxolane, 1,3-dithiole, 1,3-dithiolane, isoxazolidine, oxazolidinone and 1,3-oxathiolane.

17. The compound of claim 1, wherein said heterocyclyl is selected from the group consisting of tetrahydropyran, piperidine, piperazine, morpholine, tetrahydrofuran, pyrroline, pyrrolidone, pyrrolidone, pyrazoline, pyrazolidine, imidazoline, isoxazoline, oxazoline, oxazolidine, thiazoline and thiazolidine.

18. The compound of claim 1, wherein said compound is selected from the group consisting of:
- 2-(4-Methoxyphenyl)-N-(4-methylbenzyl)-N-{1-[3-(2-oxo-2,3-dihydrobenzoimidazol-1-yl)propyl]piperidin-4-yl}-acetamide;
- 2-(4-Methoxyphenyl)-N-(4-methylbenzyl)-N-{1-[2-(2-oxo-imidazolidin-1-yl)ethyl]piperidin-4-yl}acetamide;
- N-{1-[2-(2,4-Dioxo-1,4-dihydro-2H-quinazolin-3-yl)ethyl]piperidin-4-yl}-2-(4-methoxyphenyl)-N-(4-methylbenzyl)acetamide; and
- N-{1-[2-(1,3-Dioxolan-2-yl)ethyl]piperidin-4-yl]-2-(4-methoxyphenyl)-N-(4-methylbenzyl)acetamide.

19. The compound of claim 1, wherein $Ar^1$ is an aryl, optionally substituted with a substituent selected from the group consisting of $C_{1-6}$-alkyl, $C_{1-6}$-alkoxy, oxo, carboxyl, hydroxy, nitro, alkylsulfonyl, alkylsulfenyl, alkylsulfinyl, $C_{1-6}$-alkoxycarbonyl, $C_{1-6}$-alkylcarbonyl, formyl, amino, mono-($C_{1-6}$-alkyl)amino, di($C_{1-6}$-alkyl)amino, carbamoyl, mono-($C_{1-6}$alkyl)aminocarbonyl, di($C_{1-6}$-alkyl)aminocarbonyl, amino-$C_{1-6}$-alkyl-aminocarbonyl, mono-($C_{1-6}$-alkyl)amino-$C_{1-6}$-alkyl-aminocarbonyl, di($C_{1-6}$-alkyl)amino-$C_{1-6}$-alkyl-aminocarbonyl, $C_{1-6}$alkylcarbonylamino, $C_{1-6}$-alkylhydroxyimino, cyano, guanidino, carbamido, $C_{1-6}$-alkanoyloxy, $C_{1-6}$alkylsulphonyloxy, dihalogen-$C_{1-6}$-alkyl, trihalogen-$C_{1-6}$-alkyl, trifluoromethoxy, heterocyclyl, halo, alkylamido, hydroxy-$C_{1-6}$-alkyl, amino-$C_{1-6}$-alkyl, and sulfamoyl.

20. The compound of claim 1 selected from the group consisting of:
- N-{1-[2-(1,3-Dioxolan-2-yl)ethyl]piperidin-4-yl}-N-(4-fluorobenzyl)-N'-(4-isobutoxybenzyl)carbamide;
- N-{1-[2-(1,3-Dioxan-2-yl)ethyl]piperidin-4-yl}-N-(4-fluorobenzyl)-N'-(4-isobutoxybenzyl)carbamide;
- N-{1-[2-(1,3-Dioxolan-2-yl)ethyl]piperidin-4-yl}-N-(4-fluorobenzyl)-N'-(4-isopropoxy-benzyl)carbamide;
- N-(4-Fluorobenzyl)-N'-(4-isopropoxybenzyl)-N-{1-[2-((S)-4-methyl-1,3-dioxolane-2-yl)ethyl]piperidin-4-yl}carbamide;
- N-(4-Fluorobenzyl)-N'-(4-isopropoxybenzyl)-N-[1-(3-morpholin-4-yl-propyl)piperidin-4-yl]carbamide;
- N-(4-Fluorobenzyl)-N'-(4-isopropoxybenzyl)-N-[1-(3-piperidin-1-yl-propyl)piperidin-4-yl]carbamide;
- N-(4-Fluorobenzyl)-N'-(4-isopropoxybenzyl)-N-[1-(3-((S)-4-isopropyl-2-oxazolidinon-1-yl-propyl)piperidin-4-yl]carbamide;
- N-(4-Fluorobenzyl)-N'-(4-isopropoxybenzyl)-N-{1-[2-(2,5,5-trimethyl-1,3-dioxan-2-yl)ethyl]}piperidin-4-yl]carbamide;
- N-{1-[3-(1,3-Dioxolan-2-yl)propyl]piperidin-4-yl}-N-(4-fluorobenzyl)-N'-(4-isopropoxybenzyl)carbamide; and
- N-(4-Fluorobenzyl)-N'-(4-isopropoxybenzyl)-N-{[2-(1-methyl pyrrolidin-2-yl)ethyl]-piperidin-4-yl}carbamide.

21. The compound of claim 1, wherein: $R^2$ and $R^3$ are hydrogen; n is 1; $Ar^1$ is an aryl optionally substituted with a substituent selected from the group consisting of $C_{1-6}$-alkyl, $C_{1-6}$-alkoxy, oxo, carboxyl, amino, hydroxy, nitro, alkylsulfonyl, alkylsulfenyl, alkylsulfinyl, $C_{1-6}$-alkoxycarbonyl, $C_{1-6}$-alkylcarbonyl, formyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, $C_{1-6}$-alkylhydroxyimino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, haloalkoxy, heterocyclyl, halo, alkylamido, $C_{1-6}$ hydroxyalkyl, $C_{1-6}$ aminoalkyl, and sulfamoyl; W is selected from the group consisting of oxygen and sulfur; X is selected from the group consisting of optionally substituted methylene, optionally substituted ethylene, optionally substituted propylene, optionally substituted vinylene, and $CH_2N(R^N)$, wherein $R^N$ is selected from hydrogen and $C_{1-6}$-alkyl; and $Ar^2$ is an optionally substituted aryl.

22. The compound of claim 1, wherein $Ar^1$ is an aryl, optionally substituted with a substituent selected from the group consisting of $C_{16}$-alkyl, $C_{16}$-alkoxy, oxo, carboxyl, hydroxy, nitro, $C_{1-6}$-alkylsulfonyl, $C_{1-6}$-alkylsulfenyl, $C_{1-6}$-alkylsulfinyl, $C_{1-6}$-alkoxycarbonyl, $C_{1-6}$-alkylcarbonyl, formyl, amino, mono-($C_{1-6}$-alkyl)amino, di($C_{1-6}$-alkyl)amino, carbamoyl, mono-($C_{1-6}$-alkyl)aminocarbonyl, di($C_{1-6}$-alkyl)aminocarbonyl, amino-$C_{1-6}$-alkyl-aminocarbonyl, mono-($C_{1-6}$-alkyl)amino-$C_{1-6}$-alkyl-aminocarbonyl, di($C_{1-6}$-alkyl)amino-$C_{1-6}$-alkyl-aminocarbonyl, $C_{1-6}$-alkylcarbonylamino, $C_{1-6}$-alkylhydroxyimino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, trifluoromethoxy, heterocyclyl, halo, alkylamido, hydroxy-$C_{1-6}$-alkyl, amino-$C_{1-6}$-alkyl, and sulfamoyl.

23. The compound of claim 1, wherein $Ar^2$ is an aryl, optionally substituted with a substituent selected from the group consisting of $C_{1-6}$-alkyl, $C_{1-6}$-alkoxy, oxo, carboxyl, hydroxy, nitro, $C_{1-6}$-alkylsulfonyl, $C_{1-6}$-alkylsulfenyl, $C_{1-6}$-alkylsulfinyl, $C_{1-6}$-alkoxycarbonyl, $C_{1-6}$-alkylcarbonyl, formyl, amino, mono-($C_{1-6}$-alkyl)amino, di($C_{1-6}$-alkyl)amino, carbamoyl, mono-($C_{1-6}$-alkyl)aminocarbonyl, di($C_{1-6}$-alkyl)aminocarbonyl, amino($C_{1-6}$-alkyl-aminocarbonyl, mono-$C_{1-6}$-alkyl)amino-$C_{1-6}$-alkyl-aminocarbonyl, di($C_{1-6}$-alkyl)amino-$C_{1-6}$-alkyl-aminocarbonyl, $C_{1-6}$-alkylcarbonylamino, $C_{1-6}$-alkylhydroxyimino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, trifluoromethoxy, heterocyclyl, halo, alkylamido, hydroxy-$C_{1-6}$-alkyl, amino-$C_{1-6}$-alkyl, and sulfamoyl.

24. The compound of claim 1, wherein said heterocyclyl is 1,3-dioxane or 1,3-dioxolane.

* * * * *